US012697167B2

(12) United States Patent
Weber

(10) Patent No.: US 12,697,167 B2
(45) Date of Patent: Aug. 4, 2026

(54) APPARATUS AND METHODS FOR MINIMALLY INVASIVE DISSECTION AND MODIFICATION OF TISSUES

(71) Applicant: Paul Joseph Weber, Nendaz (CH)

(72) Inventor: Paul Joseph Weber, Nendaz (CH)

( * ) Notice: Subject to any disclaimer, the term of this patent is extended or adjusted under 35 U.S.C. 154(b) by 859 days.

(21) Appl. No.: 17/370,812

(22) Filed: Jul. 8, 2021

(65) Prior Publication Data

US 2021/0330377 A1 Oct. 28, 2021

Related U.S. Application Data

(63) Continuation of application No. 16/688,827, filed on Nov. 19, 2019, now Pat. No. 11,510,730, which is a continuation-in-part of application No. 16/141,893, filed on Sep. 25, 2018, now Pat. No. 10,893,899, which is a continuation-in-part of application No. 15/464,199, filed on Mar. 20, 2017, now Pat. No. 10,603,101.

(60) Provisional application No. 62/821,985, filed on Mar. 21, 2019, provisional application No. 62/563,005, filed on Sep. 25, 2017, provisional application No. 62/409,575, filed on Oct. 18, 2016, provisional application No. 62/313,707, filed on Mar. 26, 2016.

(51) Int. Cl.
*A61B 18/14* (2006.01)
*A61B 18/00* (2006.01)
*A61B 18/12* (2006.01)

(52) U.S. Cl.
CPC ................................ *A61B 18/1482* (2013.01); *A61B 2018/00601* (2013.01); *A61B 2018/126* (2013.01); *A61B 2018/1417* (2013.01)

(58) Field of Classification Search
CPC .... A61B 2018/00601; A61B 2018/126; A61B 2018/1417; A61B 18/1482
See application file for complete search history.

(56) References Cited

U.S. PATENT DOCUMENTS

| | | | |
|---|---|---|---|
| 2,519,125 | A | 8/1950 | Erickson |
| 4,473,077 | A | 9/1984 | Noiles |
| 4,537,791 | A | 8/1985 | Tarjan |
| 4,582,057 | A | 4/1986 | Auth |

(Continued)

OTHER PUBLICATIONS

Mar. 31, 2020 PCT/US18/052760, International Preliminary Report on Patentability (6 pgs).

(Continued)

*Primary Examiner* — Michael F Peffley
*Assistant Examiner* — Bo Ouyang
(74) *Attorney, Agent, or Firm* — Matthew D. Thayne; Thayne and Davis LLC

(57) ABSTRACT

Tissue modification instruments. In some embodiments, the instrument may comprise a shaft extending along an axis. A tissue treatment tip may be positioned at a distal end of the shaft. The tissue treatment tip may comprise one or more energy delivery elements configured to deliver tissue-modification energy. The tissue treatment tip may comprise a non-branching tip that extends away from the axis to define a tissue treatment region that is wider than a width of the shaft. The tissue treatment tip may comprise a terminal end, which may be positioned at the distal end of the instrument in some embodiments or may be positioned proximal of the distal end of the instrument.

18 Claims, 41 Drawing Sheets

(56) References Cited

U.S. PATENT DOCUMENTS

| | | | |
|---|---|---|---|
| 5,015,217 A | 5/1991 | Broadwin | |
| 5,104,394 A | 4/1992 | Knoepfler | |
| 5,139,509 A | 8/1992 | Fischer | |
| 5,170,925 A | 12/1992 | Madden | |
| 5,222,961 A | 6/1993 | Nakao | |
| 5,246,436 A | 9/1993 | Rowe | |
| 5,282,807 A | 2/1994 | Knoepfler | |
| 5,308,358 A | 5/1994 | Bond et al. | |
| 5,314,424 A | 5/1994 | Nicholas | |
| 5,368,606 A | 11/1994 | Marlow et al. | |
| 5,391,166 A | 2/1995 | Eggers | |
| 5,425,355 A | 6/1995 | Kulick | |
| 5,500,012 A | 3/1996 | Brucker | |
| 5,514,131 A | 5/1996 | Edwards | |
| 5,630,539 A | 5/1997 | Plyley | |
| 5,631,056 A | 5/1997 | Kawanishi | |
| 5,655,547 A | 8/1997 | Karni | |
| 5,693,043 A | 12/1997 | Kittrell | |
| 5,707,368 A | 1/1998 | Cozean | |
| 5,728,090 A | 3/1998 | Martin | |
| 5,733,319 A | 3/1998 | Neilson | |
| 5,755,714 A | 5/1998 | Murphy-Chutorian | |
| 5,759,182 A | 6/1998 | Varney | |
| 5,776,092 A | 7/1998 | Farin | |
| 5,788,688 A | 8/1998 | Bauer | |
| 5,810,805 A | 9/1998 | Sutcu | |
| 5,827,267 A | 10/1998 | Savage | |
| 5,980,520 A | 11/1999 | Vancaillie | |
| 6,033,398 A | 3/2000 | Farley | |
| 6,135,999 A | 10/2000 | Fanton | |
| 6,174,309 B1 | 1/2001 | Wrublewski | |
| 6,176,857 B1 | 1/2001 | Ashley | |
| 6,203,540 B1 | 3/2001 | Weber | |
| 6,210,405 B1 | 4/2001 | Goble | |
| 6,391,023 B1 | 5/2002 | Weber | |
| 6,419,674 B1 | 7/2002 | Bowser | |
| 6,428,503 B1 * | 8/2002 | Kierce | A61B 18/1482 |
| | | | 606/41 |
| 6,432,101 B1 | 8/2002 | Weber | |
| 6,440,121 B1 | 8/2002 | Weber | |
| 6,461,357 B1 | 10/2002 | Sharkey | |
| 6,494,881 B1 | 12/2002 | Bales et al. | |
| 6,500,176 B1 | 12/2002 | Truckai et al. | |
| 6,602,252 B2 | 8/2003 | Mollenauer | |
| 6,623,481 B1 | 9/2003 | Garbagnati | |
| 6,723,094 B1 * | 4/2004 | Desinger | A61B 18/1492 |
| | | | 606/41 |
| 6,808,525 B2 | 10/2004 | Laterell | |
| 6,974,450 B2 | 12/2005 | Weber | |
| 6,978,921 B2 | 12/2005 | Shelton | |
| 7,300,397 B2 | 11/2007 | Adler et al. | |
| 7,390,317 B2 | 6/2008 | Taylor et al. | |
| 7,438,702 B2 | 10/2008 | Hart et al. | |
| 7,494,460 B2 | 2/2009 | Haarstad et al. | |
| 7,494,488 B2 | 2/2009 | Weber | |
| 7,559,887 B2 | 7/2009 | Dannan | |
| 7,563,250 B2 | 7/2009 | Wenchell | |
| 7,670,338 B2 | 3/2010 | Albrecht et al. | |
| 7,690,547 B2 | 4/2010 | Racenet | |
| 7,736,361 B2 * | 6/2010 | Palanker | A61B 18/1402 |
| | | | 606/45 |
| 7,828,775 B2 | 11/2010 | Okoniewski | |
| 7,828,808 B2 | 11/2010 | Hinman et al. | |
| 7,833,275 B2 | 11/2010 | Mears et al. | |
| 7,845,534 B2 | 12/2010 | Viola | |
| 7,857,754 B2 | 12/2010 | Spivey et al. | |
| 8,029,475 B2 | 10/2011 | Franer et al. | |
| 8,033,995 B2 | 10/2011 | Cropper et al. | |
| 8,056,788 B2 | 11/2011 | Mastri | |
| 8,070,676 B2 | 12/2011 | Ewers et al. | |
| 8,075,477 B2 | 12/2011 | Nakamura et al. | |
| 8,075,530 B2 | 12/2011 | Taylor et al. | |
| 8,147,457 B2 | 4/2012 | Michael et al. | |
| 8,152,773 B2 | 4/2012 | Albrecht et al. | |
| 8,152,774 B2 | 4/2012 | Pasqualucci | |
| 8,172,806 B2 | 5/2012 | Smith | |
| 8,192,405 B2 | 6/2012 | Racenet et al. | |
| 8,225,798 B2 | 7/2012 | Baldwin et al. | |
| 8,240,538 B1 | 8/2012 | Manoux | |
| 8,303,584 B2 * | 11/2012 | Burdio Pinilla | A61B 18/148 |
| | | | 606/49 |
| 8,409,172 B2 | 4/2013 | Moll et al. | |
| 8,423,182 B2 | 4/2013 | Robinson et al. | |
| 8,424,739 B2 | 4/2013 | Racenet | |
| 8,425,406 B2 | 4/2013 | Smith et al. | |
| 8,430,851 B2 | 4/2013 | McGinley et al. | |
| 8,444,631 B2 | 5/2013 | Yeung et al. | |
| 8,458,896 B2 | 6/2013 | Chandrasekaran et al. | |
| 8,475,359 B2 | 7/2013 | Asada et al. | |
| 8,506,555 B2 | 8/2013 | Ruiz Morales | |
| 8,523,043 B2 | 9/2013 | Ulrich | |
| 8,535,312 B2 | 9/2013 | Homer | |
| 9,028,491 B2 | 5/2015 | Ellman | |
| 9,039,736 B2 | 5/2015 | Scirica | |
| 9,138,207 B2 | 9/2015 | Igov | |
| 9,155,536 B1 | 10/2015 | Hausen | |
| 9,333,029 B2 | 5/2016 | Baldwin et al. | |
| 2002/0095152 A1 * | 7/2002 | Ciarrocca | A61B 18/1492 |
| | | | 606/50 |
| 2002/0128648 A1 | 9/2002 | Weber et al. | |
| 2003/0216725 A1 | 11/2003 | Woloszko et al. | |
| 2004/0243157 A1 | 12/2004 | Connor et al. | |
| 2004/0267254 A1 * | 12/2004 | Manzo | A61B 18/14 |
| | | | 606/49 |
| 2005/0113824 A1 | 5/2005 | Sarlor | |
| 2005/0113829 A1 | 5/2005 | Dumbauld | |
| 2006/0079934 A1 | 4/2006 | Ogawa et al. | |
| 2006/0095031 A1 | 5/2006 | Ormsby | |
| 2007/0016187 A1 | 1/2007 | Weinberg | |
| 2007/0043352 A1 | 2/2007 | Garrison et al. | |
| 2009/0076504 A1 | 3/2009 | Schnitzler | |
| 2009/0118730 A1 | 5/2009 | Mollenauer | |
| 2009/0143773 A1 | 6/2009 | Goose | |
| 2009/0171352 A1 * | 7/2009 | Sutter | A61B 18/1402 |
| | | | 606/49 |
| 2009/0236398 A1 | 9/2009 | Cole | |
| 2010/0049178 A1 | 2/2010 | Deem | |
| 2010/0217253 A1 | 8/2010 | Mehta | |
| 2011/0112524 A1 | 5/2011 | Alan | |
| 2011/0184410 A1 * | 7/2011 | Greep | A61B 18/1402 |
| | | | 606/41 |
| 2012/0265186 A1 | 10/2012 | Burger | |
| 2013/0006239 A1 | 1/2013 | Pikramenos | |
| 2014/0018795 A1 | 1/2014 | Shiley | |
| 2014/0187870 A1 | 7/2014 | Weber | |
| 2014/0276757 A1 | 9/2014 | Ellman | |
| 2015/0320437 A1 | 11/2015 | Worrell | |
| 2015/0320438 A1 | 11/2015 | Weisenburgh | |
| 2015/0359585 A1 | 12/2015 | Weber | |
| 2016/0242846 A1 | 8/2016 | Brown et al. | |
| 2017/0100190 A1 | 4/2017 | Gupta | |

OTHER PUBLICATIONS

U.S. Appl. No. 15/464,199, Final Office Action dated Oct. 30, 2019.

Weber, U.S. Appl. No. 15/464,199, Final Office Action dated Oct. 30, 2019 (13 pages).

Weber, U.S. Appl. No. 15/464,199, Non-Final Office Action dated Jul. 8, 2019 (10 pages).

Weber, PCT/NZ2017/050029, International Preliminary Report on Patentability (4 pages).

Weber, EPO Application 17775960.2, Examiner Report issued Nov. 20, 2019 (6 pages).

Weber, U.S. Appl. No. 16/827,677, Non-Final Office Action dated Jul. 8, 2019 (8 pages).

Weber, Mar. 31, 2020 PCT/US2018/052760, International Preliminary Report on Patentability (6 pages).

Weber, EPO Application 18 859 414.7 dated Jul. 26, 2021, Partial European Search Report (12 pages).

Weber, May 21, 2020, PCT/NZ2020/050055, Written Opinion of the Int'l Searching Authority & International Search Report (7 pages).

(56)  References Cited

OTHER PUBLICATIONS

Weber, EPO Application 21 174 856.1 dated Oct. 6, 2021, Partial
European Search Report (6 pages).

\* cited by examiner

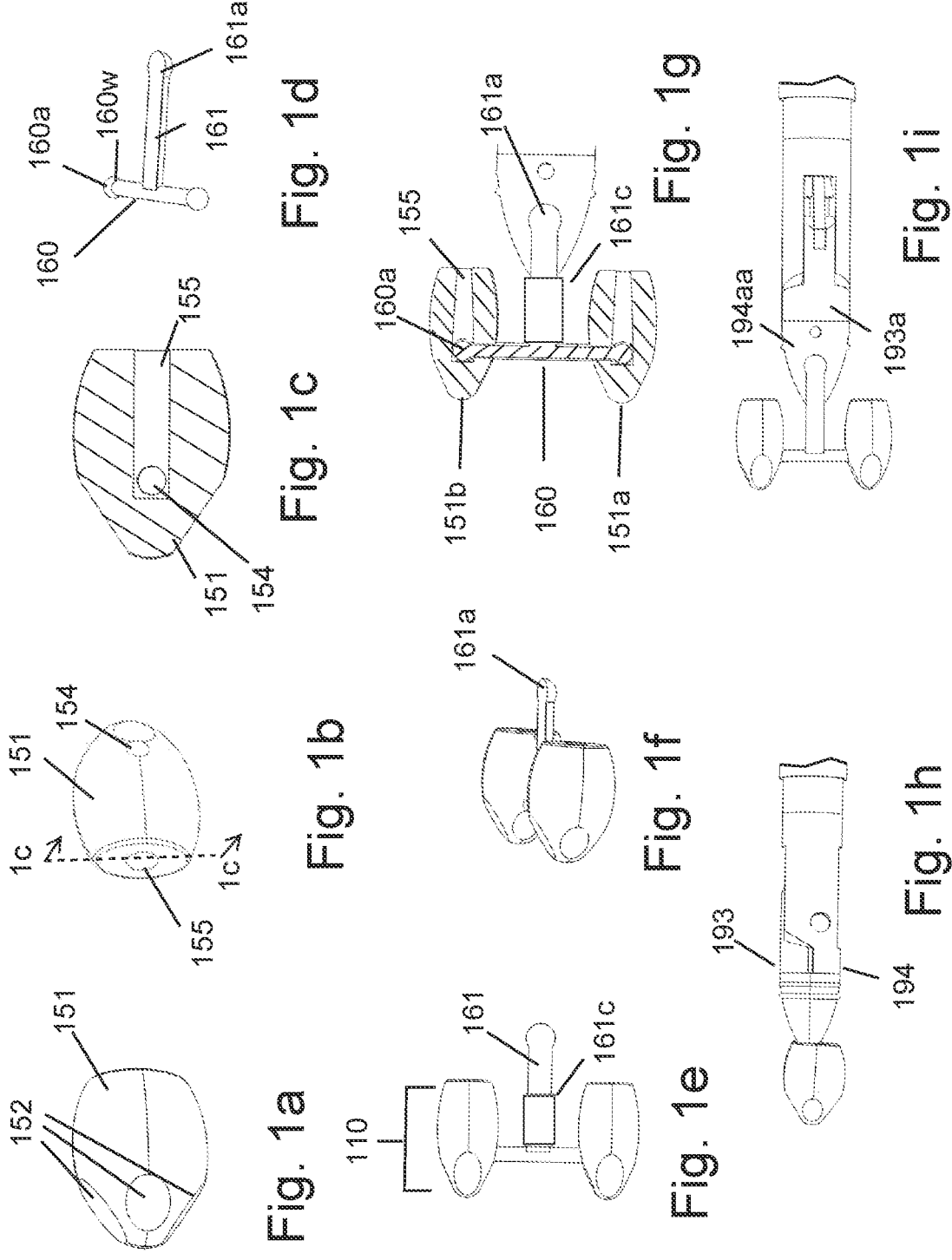

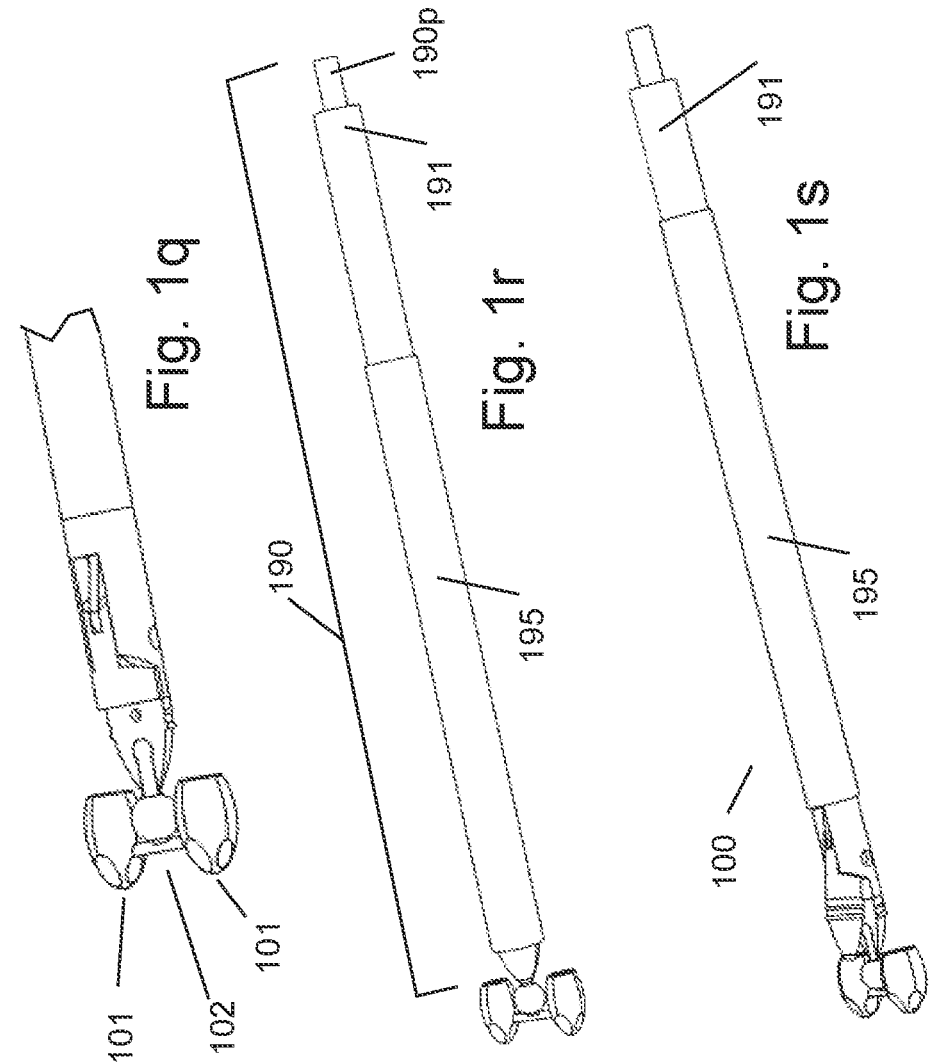

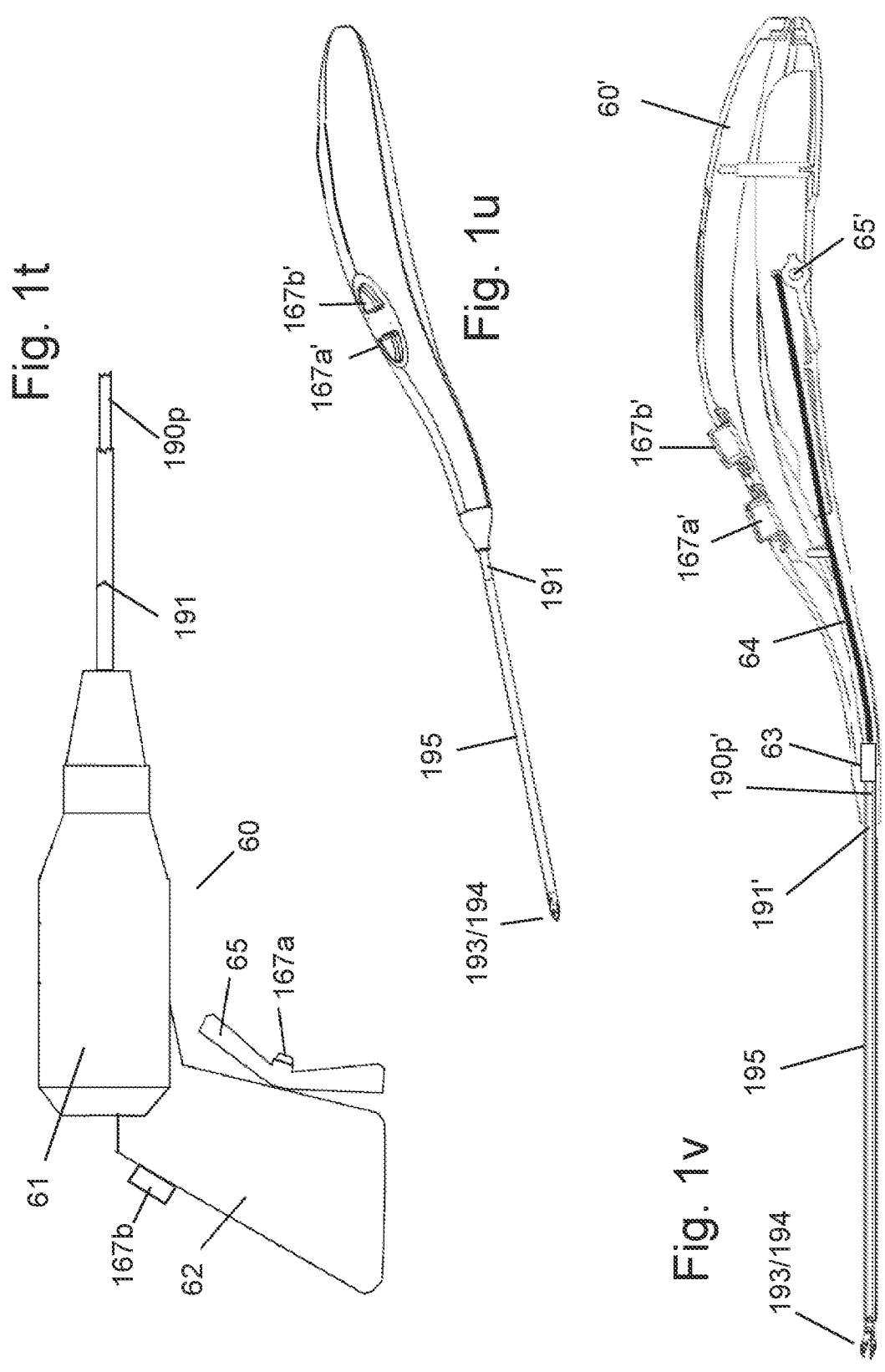

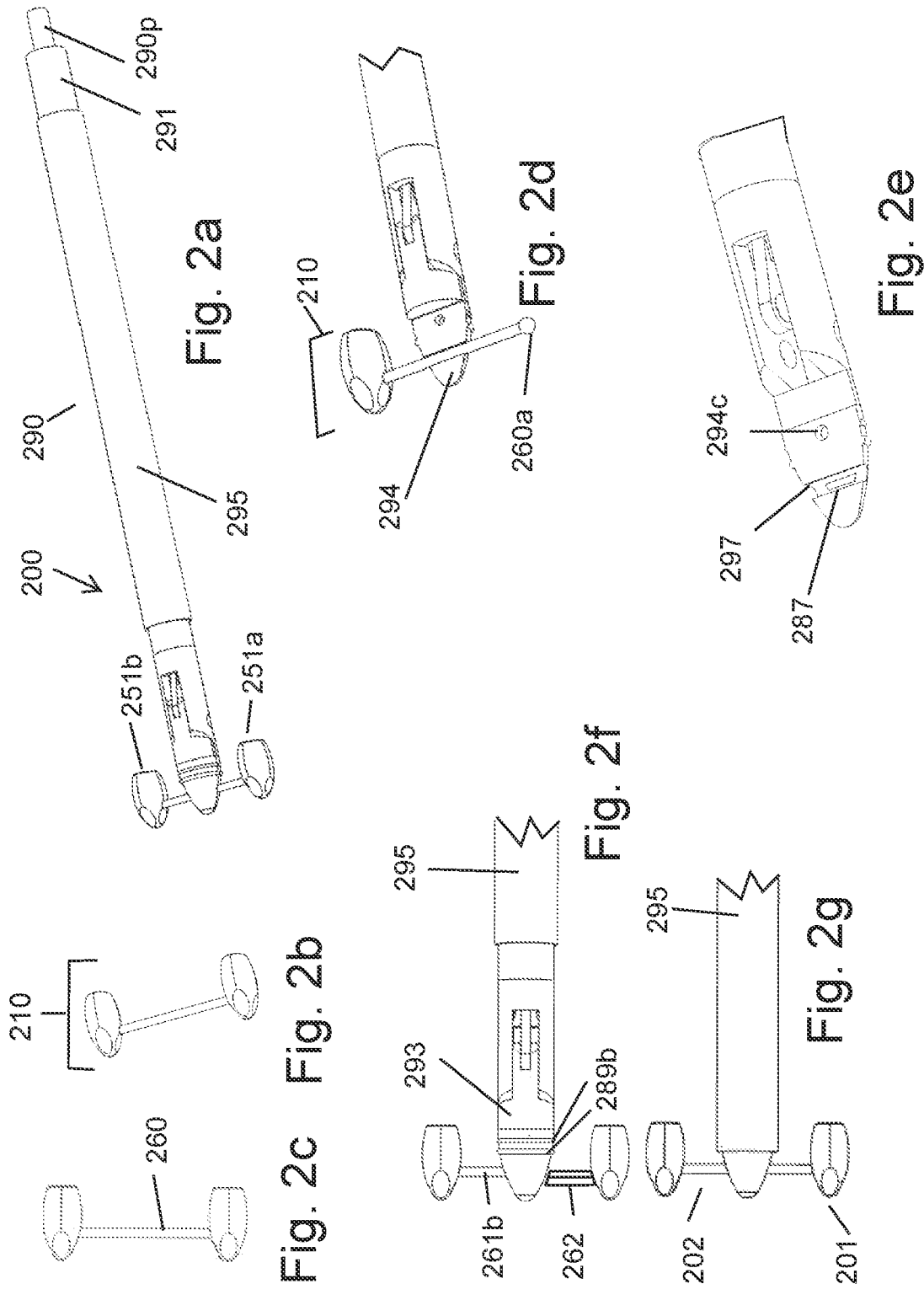

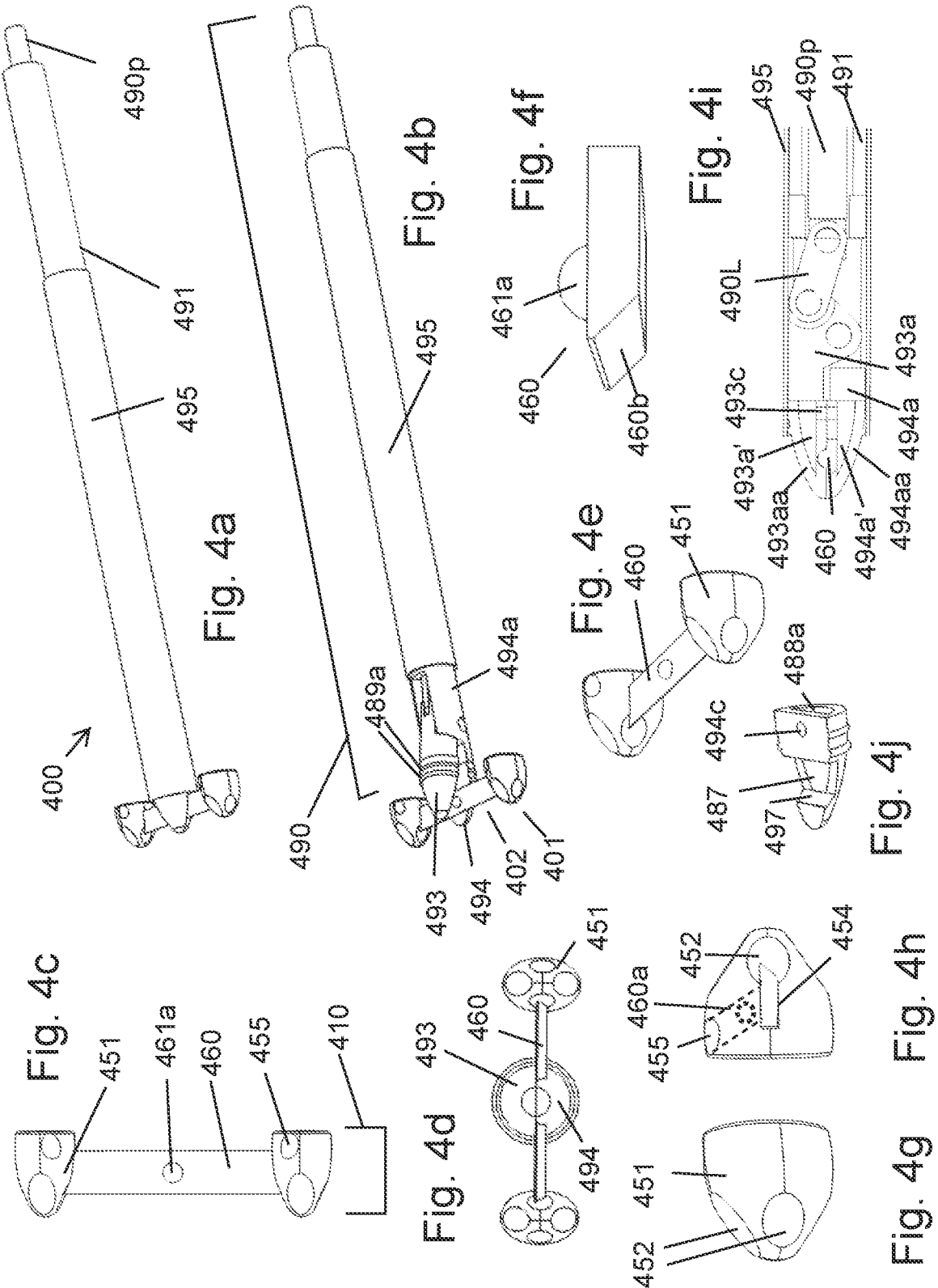

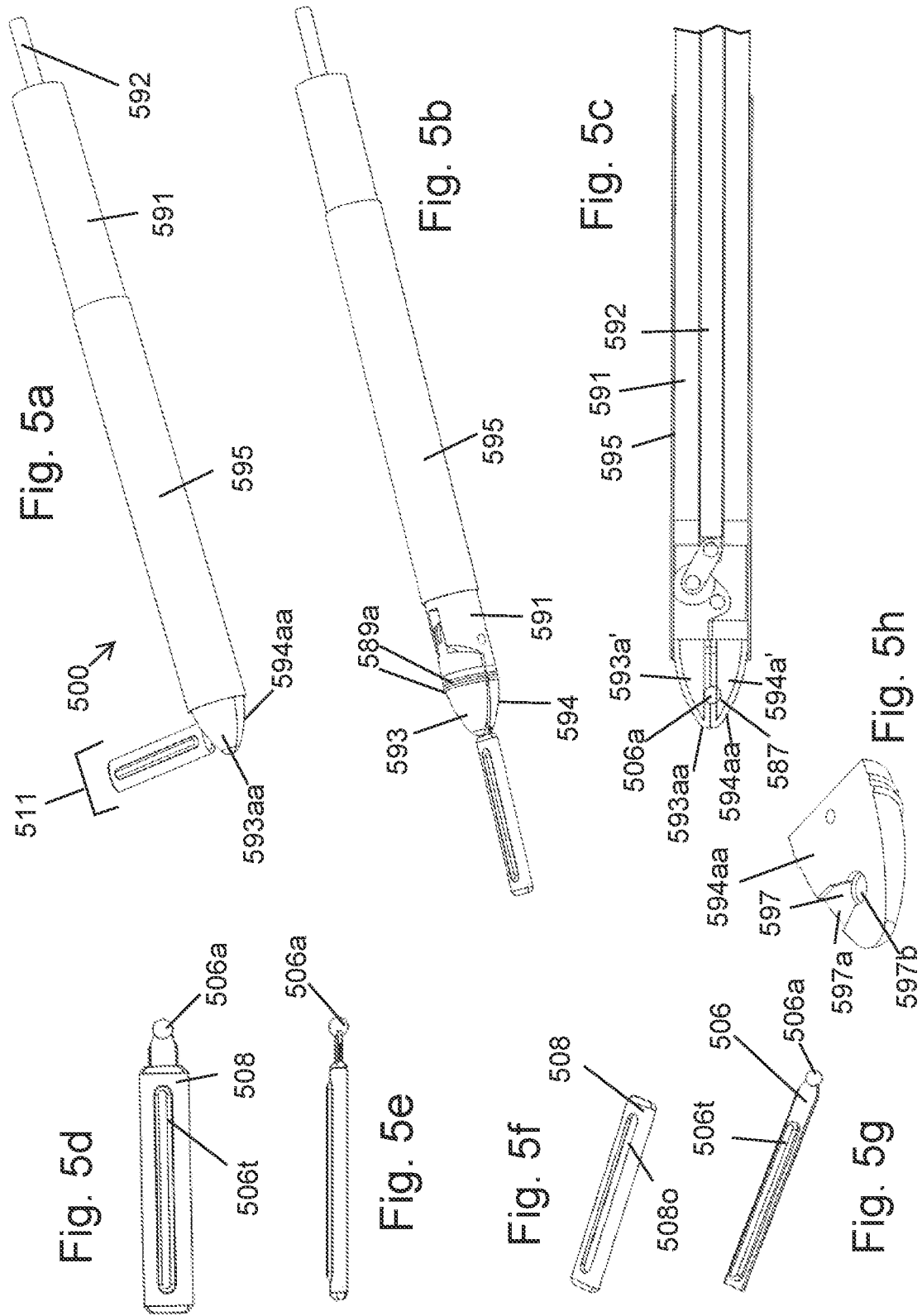

755

753

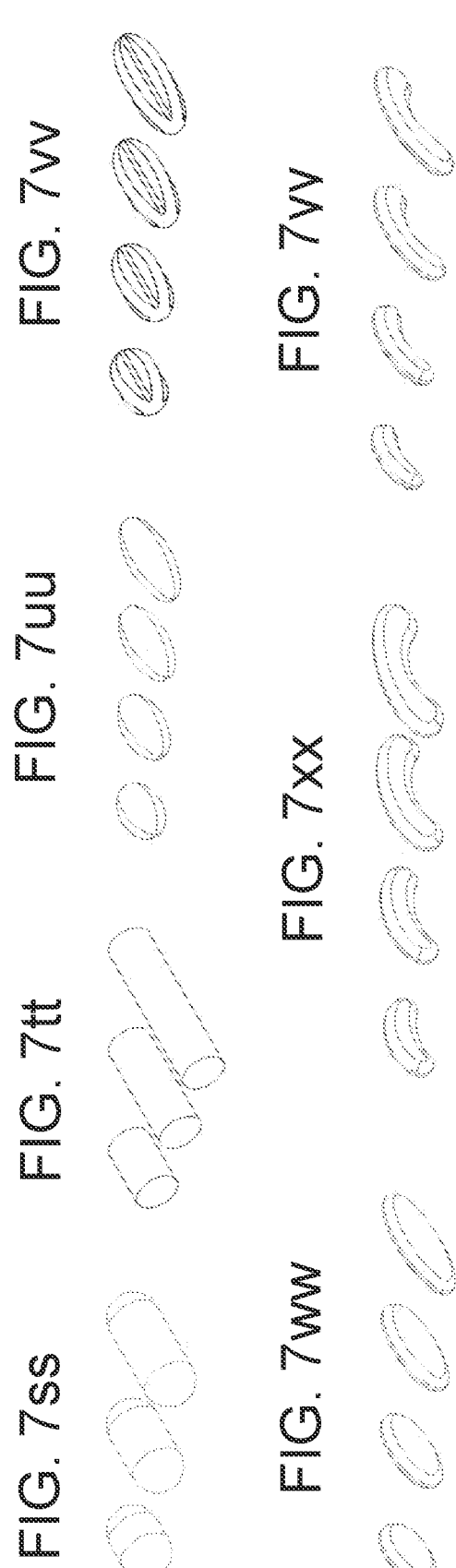
FIG. 7ss
FIG. 7tt
FIG. 7uu
FIG. 7vv
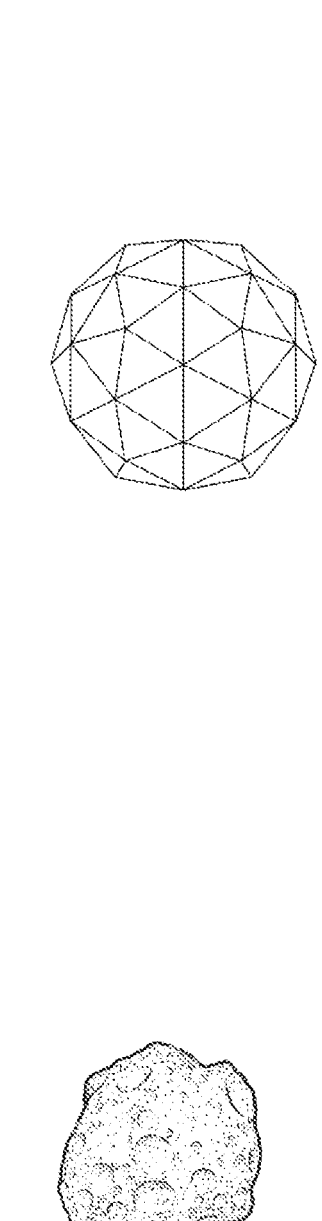
FIG. 7ww
FIG. 7xx
FIG. 7yy
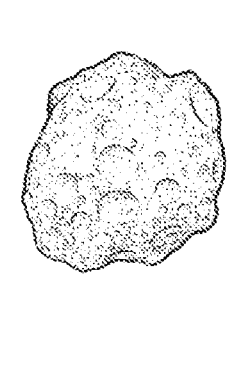
FIG. 7zz
FIG. 7zzz

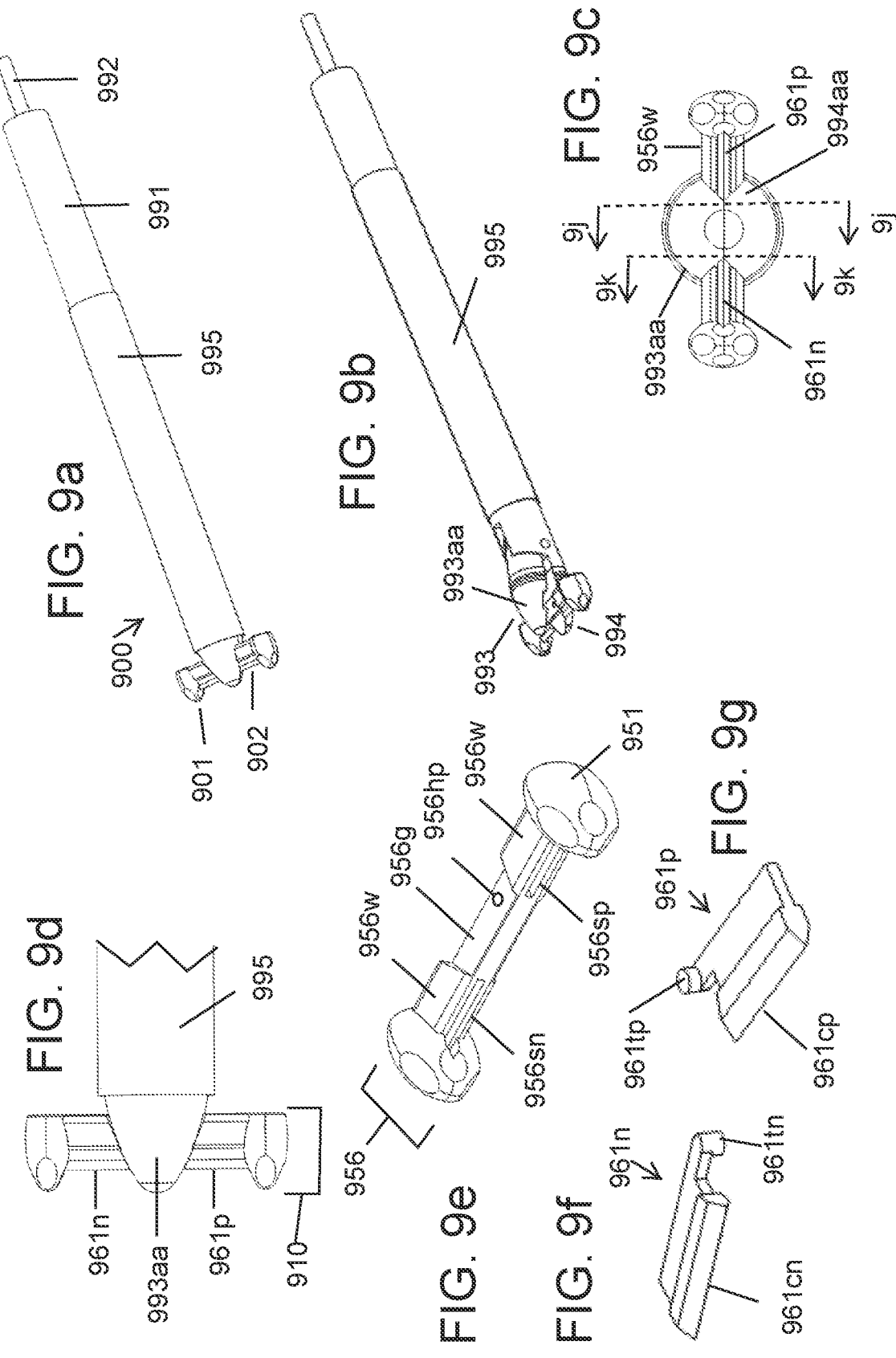

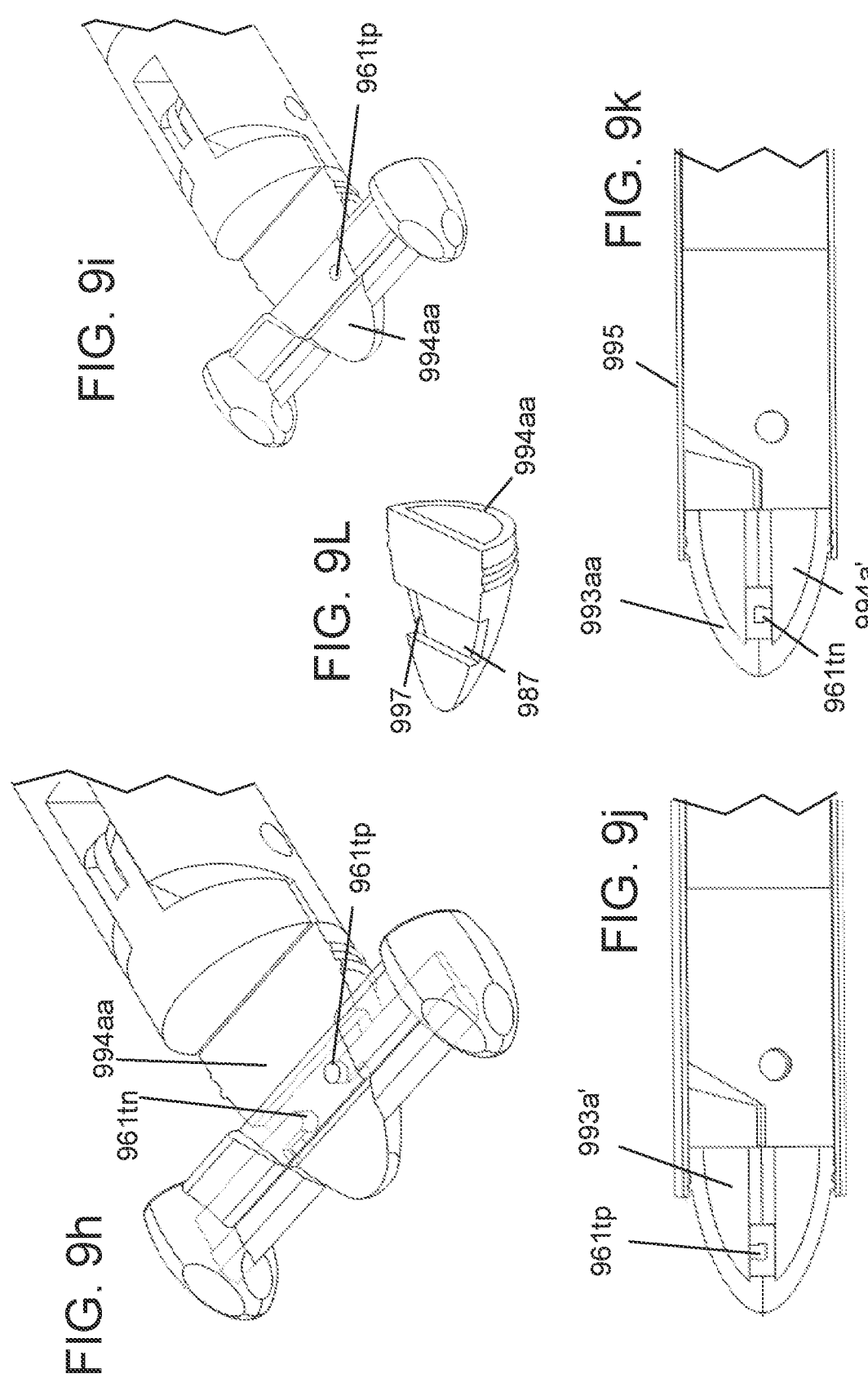

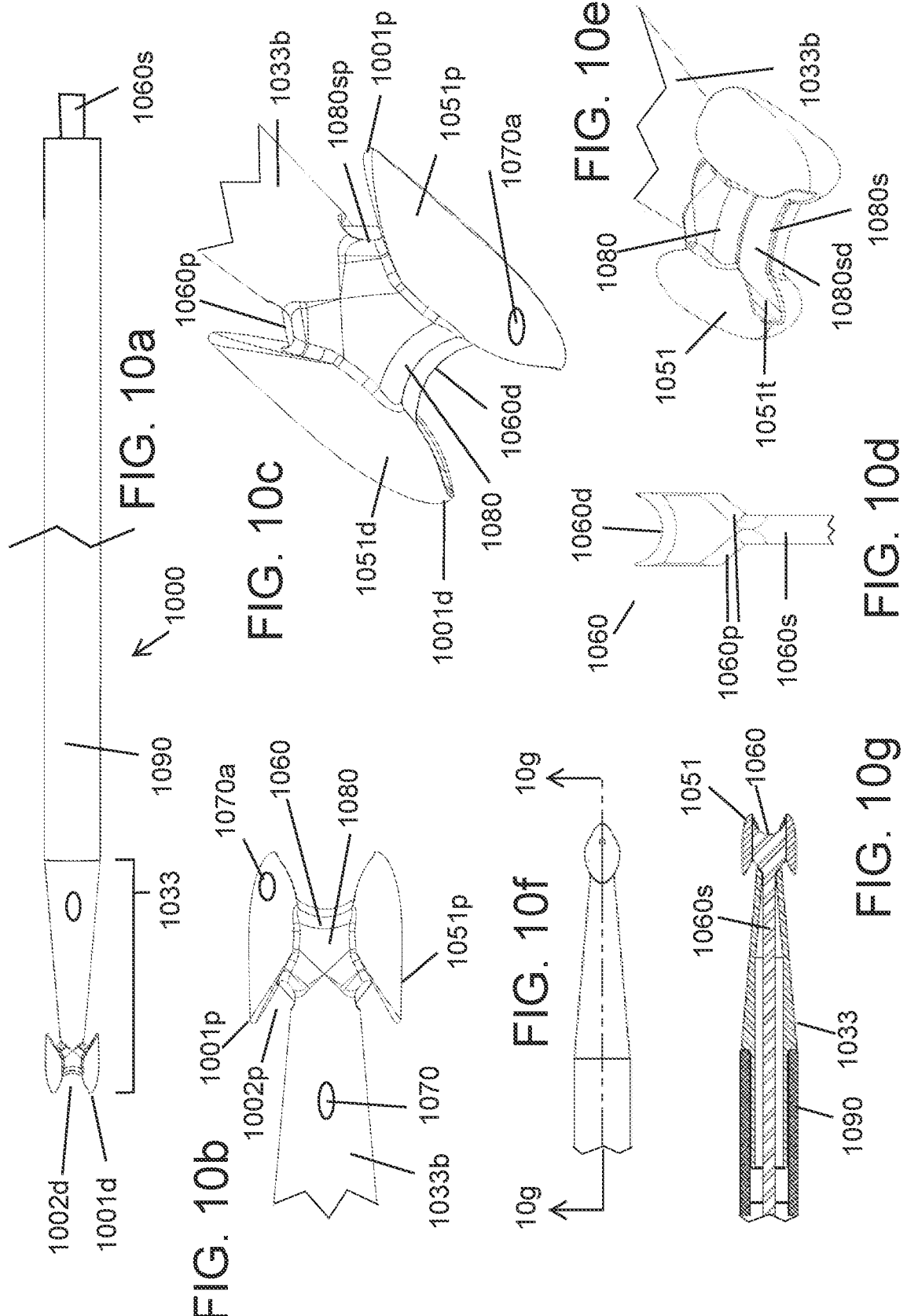

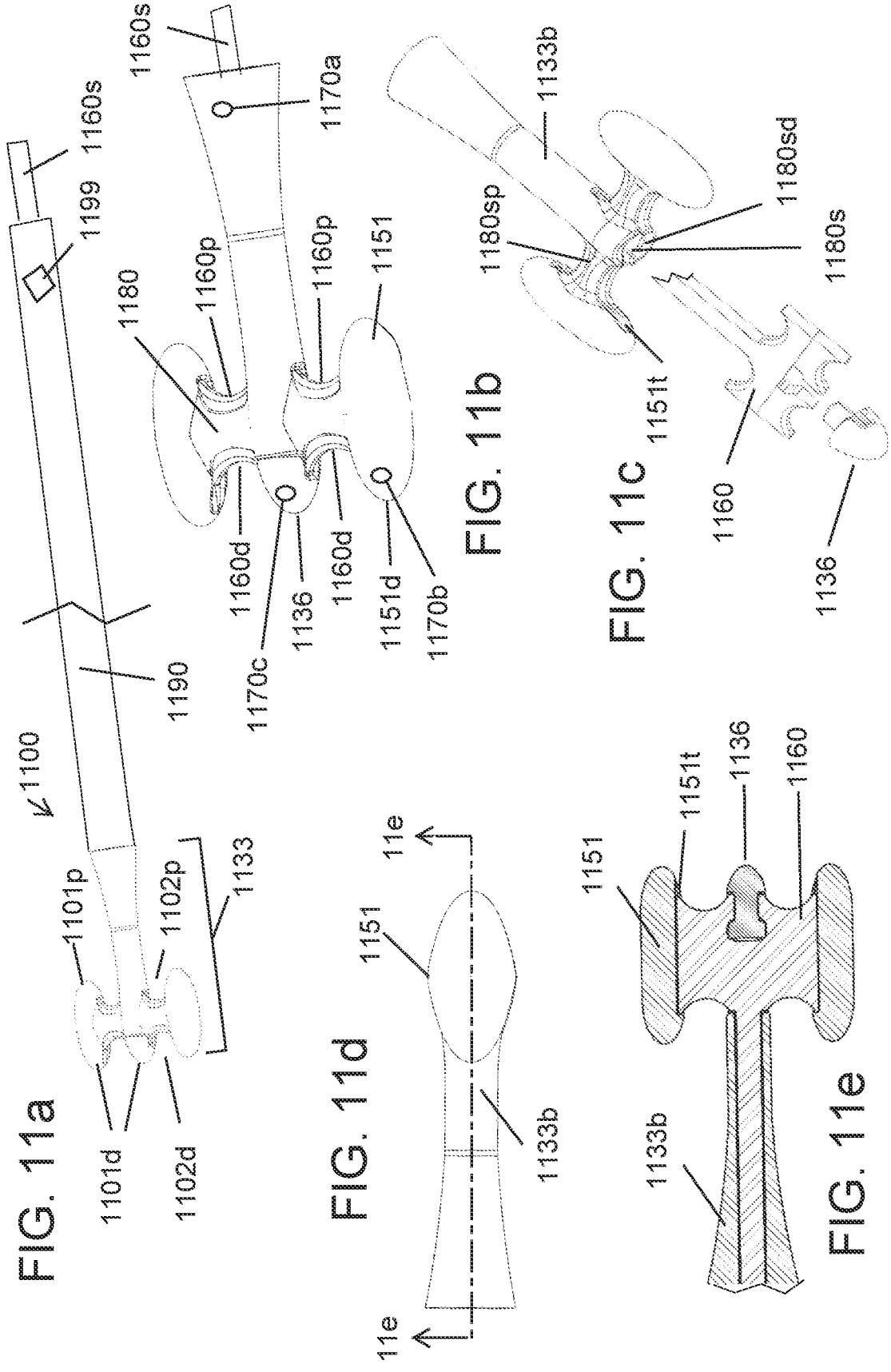

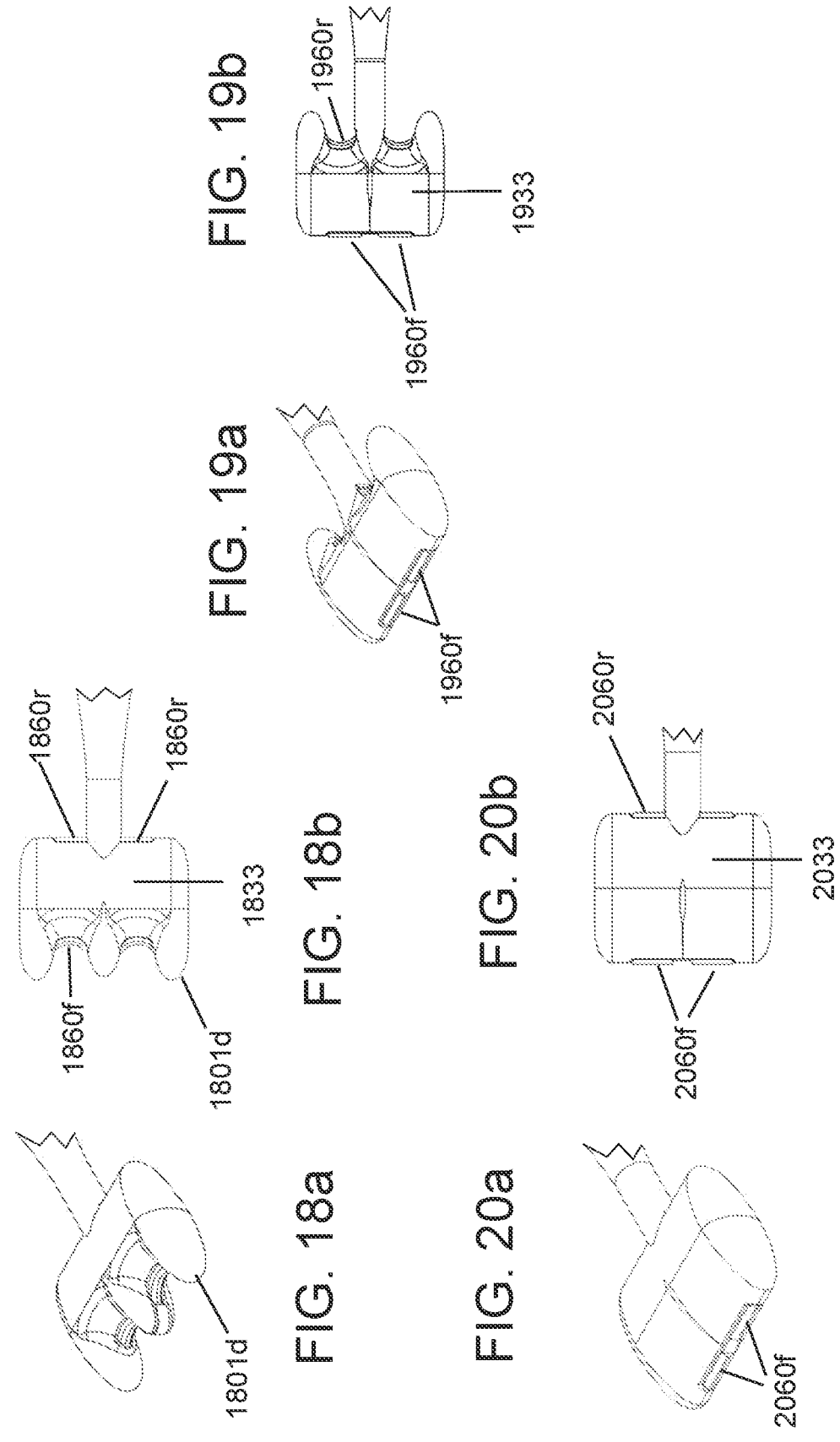

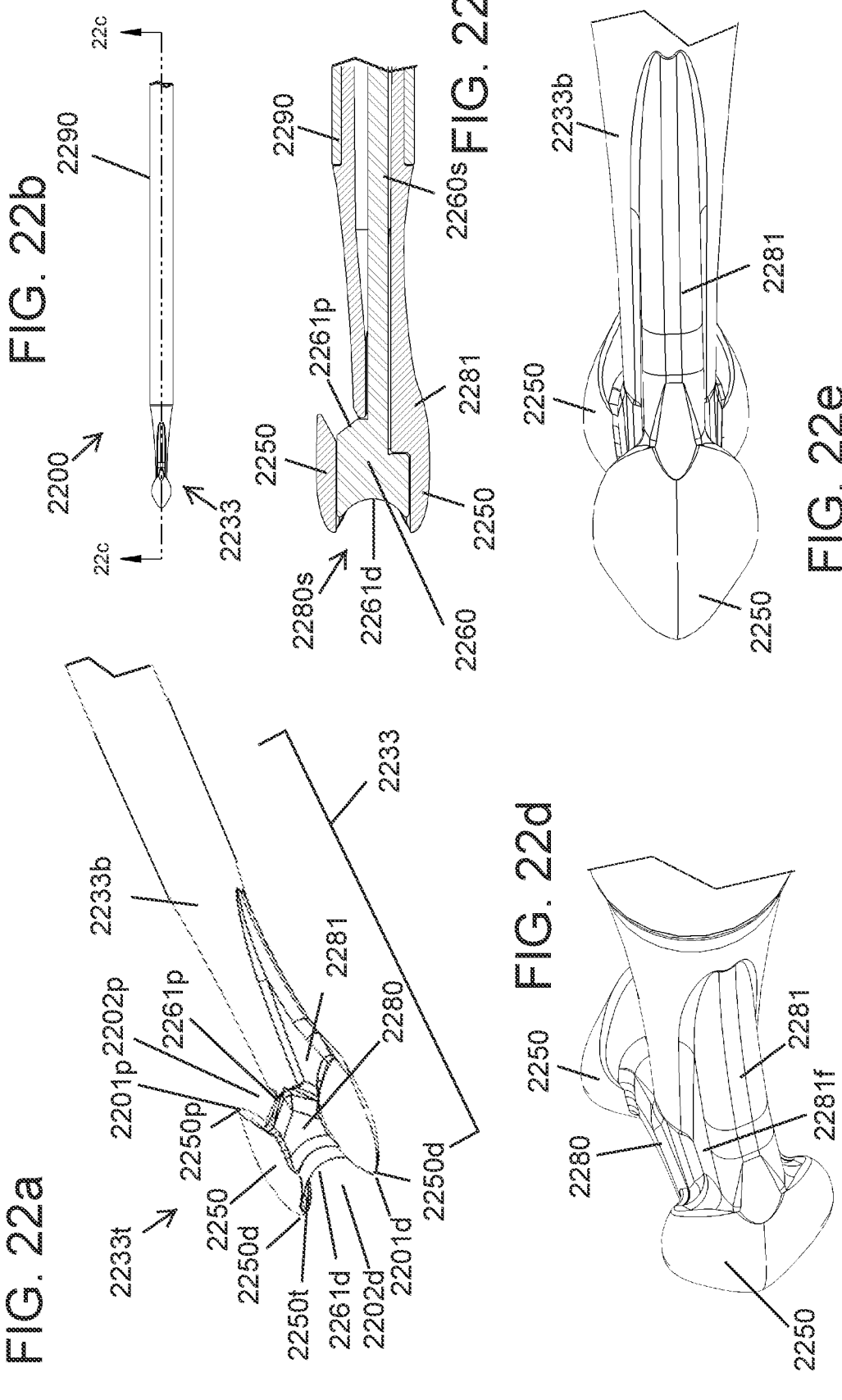

APPARATUS AND METHODS FOR MINIMALLY INVASIVE DISSECTION AND MODIFICATION OF TISSUES

RELATED APPLICATIONS

This application is a continuation of U.S. patent application Ser. No. 16/688,827 filed on Nov. 19, 2019 and titled "APPARATUS AND METHODS FOR MINIMALLY INVASIVE DISSECTION AND MODIFICATION OF TISSUES," which claims the benefit under 35 U.S.C. § 119(e) of U.S. Provisional Patent Application No. 62/821,985 filed on Mar. 21, 2019 and also titled "APPARATUS AND METHODS FOR MINIMALLY INVASIVE DISSECTION AND MODIFICATION OF TISSUES" and is also a continuation-in-part of U.S. patent application Ser. No. 16/141,893 filed on Mar. 20, 2017 and titled "APPARATUS AND SYSTEMS FOR MINIMALLY INVASIVE DISSECTION OF TISSUES," which claims the benefit under 35 U.S.C. § 119(e) of U.S. Provisional Patent Application No. 62/563,005 filed Sep. 25, 2017 and titled "APPARATUS AND SYSTEMS FOR MINIMALLY INVASIVE DISSECTION OF TISSUES" and is a continuation-in-part of U.S. patent application Ser. No. 15/464,199 filed on Mar. 20, 2017 and titled "APPARATUS, SYSTEMS AND METHODS FOR MINIMALLY INVASIVE DISSECTION OF TISSUES," which claims priority to U.S. Provisional Patent Application No. 62/313,707, which was filed on Mar. 26, 2016, along with U.S. Provisional Patent Application No. 62/409,575, which was filed on Oct. 18, 2016. Each of the aforementioned applications is hereby incorporated herein by reference.

SUMMARY

The term 'dissection' may indicate the separation of tissues or of one tissue plane from another (ref: Free Online Medical Dictionary). Some also consider dissection to comprise separation of a single tissue into portions. Much of the bodies of animals and humans are formed from embryonic fusion planes. Many of the organs of the human or animal body may be categorized from the embryonic fusion planes from whence they came. The interfaces between organs may often be referred to as 'tissue planes.' Such planes may be considered substantially planar depending upon the size of a comparative planar living or inanimate object (such as a surgical instrument). The embodiments disclosed herein may perform the functions of sharp dissection, blunt dissection, electrosurgical cutting and/or coagulation simultaneously without a surgeon having to switch instruments. Tissue modification may also be carried out, in some of the preferred embodiments and implementations disclosed herein using a separate tissue modification instrument that may be deployed through a path to a target region created using a tissue dissection instrument, as described in detail below. In some cases, tissue planes at the target region may also be formed and/or treated using the tissue dissection instrument to facilitate subsequent tissue treatment using the tissue treatment/modification instrument.

Sharp dissection has been referred to by some as separation of tissues by means of the sharp edge of a knife or scalpel or with the inner sharp edge of scissors. Blunt dissection has been defined by Webster as surgical separation of tissue layers by means of an instrument without a cutting edge or by the fingers.

The term 'lysing' implies dissection, may also imply cutting through especially fibrous elements, and may also imply the separation of discreet structures that are somehow adhered to each other.

Some embodiments disclosed herein may comprise cannula-delivered tissue dissectors (CDTD). Other embodiments disclosed herein may be used without a cannula and may therefore be considered non-cannula-delivered tissue dissectors (non-CDTD). Some embodiments may be used either with or without cannulas and therefore, depending upon the systems/procedure, may be considered CDTD or non-CDTD. Both the CDTD and non-CDTD embodiments disclosed herein may perform the functions of sharp dissection, blunt dissection, electrosurgical cutting and/or coagulation simultaneously without a surgeon having to switch instruments. Tissue modification may also be carried out.

The term 'minimally invasive surgery' has been used to describe a procedure (surgical or otherwise) that is less invasive than open surgery used for the same purpose. Some minimally invasive procedures typically involve use of laparoscopic and/or endoscopic devices and manual and/or remote/computerized manipulation of instruments with indirect observation of the surgical field through an endoscope or similar device and are carried out through the skin or through a body cavity or anatomical opening. This may result in shorter hospital stays or allow outpatient treatment (reference: Wikipedia).

Sometimes minimally invasive surgery is known as "keyhole" surgery and may be performed using one or more trocars and one or more laparoscopes and/or endoscopes and/or cannulae to access tissues within the body.

The term 'open surgery' is used to indicate cutting skin and tissues to 'open the body' so that the surgeon has direct access to the structures or organs involved. An incision may of the size that permits a surgeon's hands to enter the patient's body. The structures and tissues involved may be seen and touched and may be directly exposed to the air of the operating room.

The term "cannula," as used herein, is intended to encompass any tube or tubular structure that is configured to be inserted into the body of a human or animal during a surgical procedure and facilitate selective movement of a surgical device and/or related components for performing delivery of the surgical device and/or surgical procedures with the surgical device. Tubular structures that contain fixed structures/elements therein, such as needle drivers or grasping instruments, are not considered cannulas as that term is used herein. Although often "trocars" are used in connection with cannulas, the term cannula, as used herein, is intended to encompass a trocar alone if such a trocar is capable of being used to insert a medical device into a body.

It may be advantageous to have a spot coagulator extend from an embodiment of the CDTD at such a distance and/or location that allows complete viewing and/or contact of a bleeding area with a portion of the spot coagulator (for example the distal end point of a tip of the coagulator). Such a probe may be deployable and may obtain electrical energy off of a conductive element located between the lysing elements of the tip and the plug.

Various examples of instruments and devices according to some embodiments of the inventions disclosed herein are as follows:

1. An electrosurgical lysing device, comprising:
   a lysing tip comprising at least one bead;
   at least one lysing member configured to deliver electrosurgical energy from the lysing tip, the at least one lysing member defining at least one lysing segment extending within a recess at least partially defined by the at least one bead; and a tunnel extending at least partially through the at least one bead, wherein the at least one lysing member extends at least partially through the tunnel.

2. The electrosurgical lysing device of example 1, further comprising a nonconductive strut coupled with the at least one bead.

3. The electrosurgical lysing device of example 2, further comprising a tissue-deflecting strut positioned between a proximal portion of the nonconductive strut and a proximal portion of the at least one bead.

4. The electrosurgical lysing device of example 2, wherein the at least one lysing member is at least partially positioned within the nonconductive strut.

5. The electrosurgical lysing device of example 4, wherein the at least one lysing member is fully positioned within the nonconductive strut such that no portion of the at least one lysing member protrudes from the nonconductive strut.

6. The electrosurgical lysing device of example 4, wherein the at least one lysing member partially protrudes from the nonconductive strut to allow for direct contact with tissue during a tissue lysing procedure.

7. The electrosurgical lysing device of example 1, further comprising a shaft, wherein the lysing tip is positioned at a distal end of the shaft.

8. The electrosurgical lysing device of example 1, wherein the at least one lysing member is configured to allow for either anterograde or retrograde lysing.

9. The electrosurgical lysing device of example 1, wherein a single bead of the at least one bead is configured to at least partially define both proximal and distal facing lysing segments.

10. A tissue modification instrument for delivery of tissue-modification energy during a surgical procedure, comprising:

a shaft extending along an axis;

a tissue treatment tip at a distal end of the shaft, the tissue treatment tip comprising one or more energy delivery elements configured to deliver tissue-modification energy, wherein the tissue treatment tip comprises a non-branching tip that extends away from the axis to define a tissue treatment region that is wider than a width of the shaft.

11. The tissue modification instrument of example 10, wherein the tissue treatment tip comprises an anfractuous tip.

12. The tissue modification instrument of example 10, wherein a cross-sectional size of the tissue treatment tip is at least substantially identical to a cross-sectional size of at least a portion of the shaft extending along the axis adjacent to the tissue treatment tip.

13. The tissue modification instrument of example 12, wherein a cross-sectional size of the tissue treatment tip is at least substantially identical to a cross-sectional size of the shaft along an entire length of the shaft.

14. The tissue modification instrument of example 10, wherein the one or more energy delivery elements comprises a plurality of discrete energy delivery termini.

15. The tissue modification instrument of example 10, wherein the one or more energy delivery elements is configured to deliver at least one of electrosurgical, LASER, intense pulse light, resistive heat, radiant heat, thermochromic, ultrasound, and microwave.

16. The tissue modification instrument of example 10, wherein the tissue treatment tip comprises an upper surface, a lower surface, and opposing side surfaces, wherein the opposing side surfaces comprise one or bends, and wherein each of the one or more bends are smooth and lack any sharp points or edges.

17. The tissue modification instrument of example 16, wherein the tissue treatment tip defines an at least substantially circular shape extending from the shaft.

18. The tissue modification instrument of example 16, wherein the tissue treatment tip defines an at least substantially rectangular shape having three sides.

19. The tissue modification instrument of example 18, wherein a corner between two adjacent sides of the three sides forms a distal tip of the tissue modification instrument.

20. The tissue modification instrument of example 10, wherein the tissue treatment tip comprises a first set of energy delivery elements of a first polarity and a second set of energy delivery elements of a second polarity.

21. The tissue modification instrument of example 20, wherein the tissue treatment tip comprises a first arm and a second arm positioned opposite from the first arm, wherein the first set of energy delivery elements is positioned on the first arm, and wherein the second set of energy delivery elements is positioned on the second arm.

22. The tissue modification instrument of example 10, wherein the tissue treatment tip comprises a first portion spaced apart from a second portion, wherein the first portion comprises a first set of energy delivery elements, and wherein the second portion comprises a temperature sensor configured to sense a temperature of tissue treated using the first set of energy delivery elements.

23. The tissue modification instrument of example 22, wherein the first portion is positioned on a first arm of the tissue treatment tip, wherein the second portion is positioned on a second arm of the tissue treatment tip, and wherein the first arm is spaced apart from the second arm.

24. A tissue dissection and/or modification instrument, comprising:

a treatment tip comprising one or more projecting electrode termini, each of the one or more projecting electrode termini comprising:

a nonconductive base;

a nonconductive shell projecting from the nonconductive base; and a conductive core positioned within the nonconductive shell and terminating in an apex adjacent to a tip of the nonconductive shell, wherein the apex is configured to deliver electrosurgical energy therethrough to adjacent tissue during a surgical procedure.

25. The tissue dissection and/or modification instrument of example 24, wherein the conductive core comprises a hollow chamber.

26. The tissue dissection and/or modification instrument of example 25, wherein the hollow chamber tapers from a narrow portion at an upper end of the hollow chamber to a widened portion at a lower end of the hollow chamber.

27. The tissue dissection and/or modification instrument of example 24, wherein the apex comprises a depression.

28. The tissue dissection and/or modification instrument of example 24, wherein the apex comprises a projection.

29. The tissue dissection and/or modification instrument of example 28, wherein the projection extends from a depression formed at the apex.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1a is a side view of a bead of the embodiment shown in FIG. 1r.

FIG. 1b is a back perspective view of a bead of the embodiment shown in FIG. 1r.

FIG. 1c is a cross sectional side view of the embodiment previously depicted in FIG. 1b at the location shown in FIG. 1b.

FIG. 1d is a perspective view of the lysing rod assembly.

FIG. 1e is an upper view of lysing tip of the embodiment shown in FIG. 1r.

FIG. 1f is side perspective view of the lysing tip of the embodiment shown in FIG. 1r.

FIG. 1g is upper cross sectional view of the lysing tip coupled to the lower jaw assembly of the embodiment shown in FIG. 1r.

FIG. 1h is a side view of the lysing tip and distal portion of the grasping/control instrument of the embodiment shown in FIG. 1r.

FIG. 1i is an upper view of the lysing tip and distal portion of the grasping/control instrument with the upper jaw removed of the embodiment shown in FIG. 1r.

FIG. 1q is a perspective view of the distal end of the embodiment shown in FIG. 1r with part of upper jaw assembly removed to expose seating of lysing tip.

FIG. 1r is a perspective view of an embodiment of a system for delivery of a lysing tip in a treatment configuration with jaws closed.

FIG. 1s is a perspective view of an embodiment of a system for delivery of a lysing tip in a treatment configuration with jaws open.

FIG. 1t is a side view of a handle assembly.

FIG. 1u is a perspective view of another style of handle assembly with shaft and jaws.

FIG. 1v is a cross sectional side view of the embodiment shown in FIG. 1u.

FIG. 2a is a perspective view of an embodiment of a system for delivery of a lysing tip in a treatment configuration.

FIG. 2b is a perspective view of the lysing tip of the embodiment shown in FIG. 2a.

FIG. 2c is an upper view of the lysing tip of the embodiment shown in FIG. 2a.

FIG. 2d is a perspective view of the distal tip of the grasping/control instrument with upper jaw components removed and lysing tip with one bead removed of the embodiment shown in FIG. 2a.

FIG. 2e is a perspective view of the lower jaw assembly of the embodiment shown in FIG. 2a.

FIG. 2f is an upper view of the distal end of the embodiment shown in FIG. 2a with sleeve retracted exposing armature.

FIG. 2g is an upper view of the distal end of the embodiment shown in FIG. 2a with sleeve covering armature.

FIG. 2h is a cross sectional side view of the grasping/control instrument and lysing tip of the embodiment shown in FIG. 2a.

FIG. 2i is a perspective view of a lower jaw covering of the embodiment shown in FIG. 2a.

FIG. 2j is a perspective view of the lower jaw and tongue of the embodiment shown in FIG. 2a.

FIG. 2k is a perspective view of the distal end of the embodiment shown in FIG. 2a with jaws open.

FIG. 2L is a perspective view of the lower jaw covering exposing the electrosurgical energy transfer opening of the embodiment shown in FIG. 2a.

FIG. 2m is an upper view of a lysing tip with a loop.

FIG. 4a is a perspective view of an embodiment of a system for delivery of a lysing tip in a treatment configuration with sleeve positioned distally.

FIG. 4b is a perspective view of the embodiment previously depicted in FIG. 4a with sleeve positioned proximally exposing armature and with jaw open.

FIG. 4c is an upper view of the lysing tip of the embodiment depicted in FIG. 4a.

FIG. 4d is a front view of the embodiment depicted in FIG. 4a.

FIG. 4e is a perspective view of the lysing tip of the embodiment previously depicted in FIG. 4a.

FIG. 4f is a lower perspective view of the lysing member of the embodiment previously depicted in FIG. 4a.

FIG. 4g is a side view of the bead of the embodiment previously depicted in FIG. 4a.

FIG. 4h is a view of the other side of the bead depicted in FIG. 4g.

FIG. 4i is a cross sectional view of the distal end of the grasping/control instrument of the embodiment depicted in FIG. 4a.

FIG. 4j is a perspective view of a lower jaw covering of the embodiment depicted in FIG. 4a.

FIG. 5a is a perspective view of an embodiment of a system for delivery of an energy window in the treatment configuration with sleeve positioned distally.

FIG. 5b is a perspective view of the embodiment depicted in FIG. 5a in the delivery configuration.

FIG. 5c is a side cross sectional view of the grasping/control instrument of the embodiment depicted in FIG. 5a.

FIG. 5d is an upper view of the TMT of the embodiment depicted in FIG. 5a.

FIG. 5e is a front view of the TMT of the embodiment depicted in FIG. 5a.

FIG. 5f is a perspective view of the cover of the embodiment depicted in FIG. 5a.

FIG. 5g is a perspective view of the energy window of the embodiment depicted in FIG. 5a.

FIG. 5h is a perspective view of the lower jaw covering of the embodiment depicted in FIG. 5a.

FIG. 6a is perspective view of a sleeve with inflatable segments.

FIG. 6b is a front view of the sleeve depicted in FIG. 6a.

FIG. 7dx comprises a perspective view of a lysing member/lysing rod having a pentagonal cross section that is twisted along its length.

FIG. 7px comprises a perspective view of a spacer to a lysing tip with a hole through its length having a pentagonal cross section that is twisted along its length.

FIG. 7aa is a perspective view of a bead having a spherical shape.

FIG. 7bb is a perspective view of a bead having a wheel shape.

FIG. 7cc is a perspective view of a bead having a dodecahedron shape.

FIG. 7dd is a perspective view of a bead having a substantially ellipsoidal shape.

FIG. 7ee is a perspective view of a bead having a substantially ellipsoidal shape with facets.

FIG. 7ff is a perspective view of a bead having a substantially ellipsoidal shape able to accept a sleeve.

FIG. 7gg is a perspective view of a bead having a partially ellipsoidal shape with a flat proximal end and facets.

FIG. 7hh is a perspective view of a bead having a partially ellipsoidal shape with two flat surfaces on its proximal end.

FIG. 7ii is an upper view of a bead having a partially ellipsoidal shape with convex proximal end.

FIG. 7jj is an upper view of a bead having a partially ellipsoidal shape with an asymmetric proximal end with facets.

FIG. 7kk is an upper view of a bead having a partially ellipsoidal shape with an angular cut-out on its proximal end.

FIG. 7LL is an upper view of a bead having a partially ellipsoidal shape with a concave proximal end.

FIG. 7mm is a side view, from the outside, of an outer bead having a substantially annular shape.

FIG. 7nn is a side view, from the inside, of bead depicted in FIG. 7mm.

FIG. 7oo is a side view of a deformable bead having a substantially annular shape.

FIG. 7pp is a side view of a middle bead having a substantially annular shape and knobs on its proximal end.

FIG. 7qq is a side view of a middle bead having a substantially annular shape and a cross-member at its proximal end.

9
10

Figures 7A, 7B, 7C, 7D, 7E, 7F, 7G:
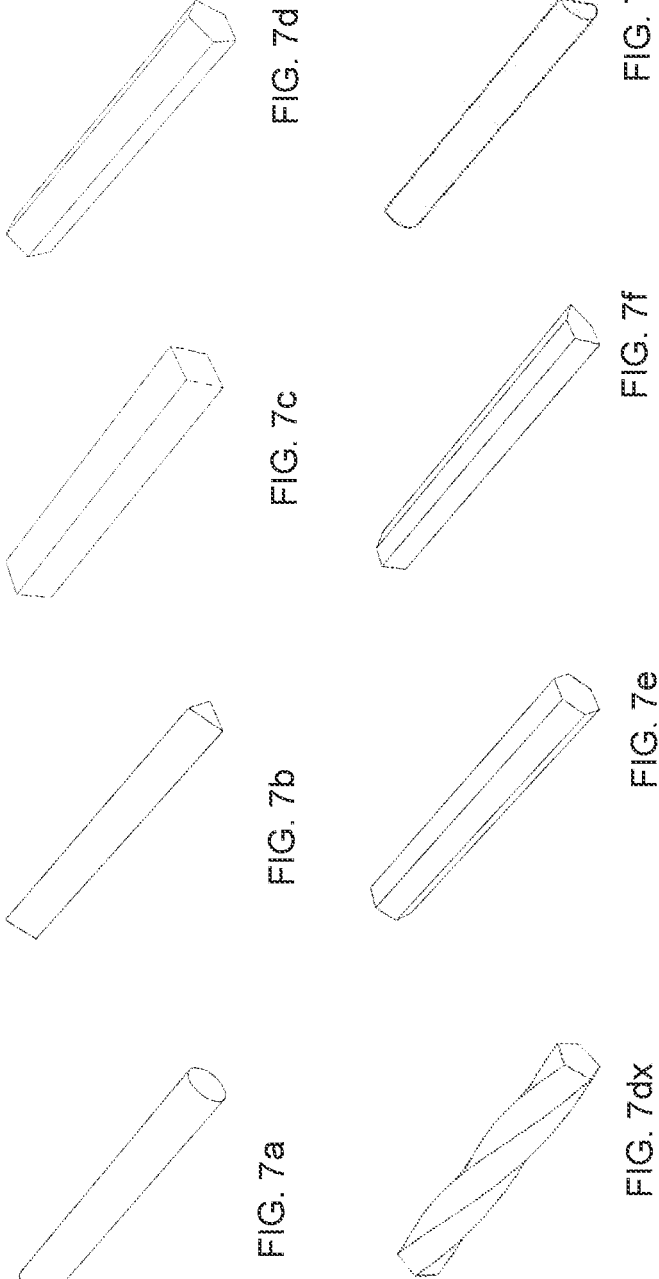
FIG. 7a comprises a perspective view of a lysing member/lysing rod with a circular cross-section.
FIG. 7b comprises a perspective view of a lysing member/lysing rod with a triangular cross-section.
FIG. 7c comprises a perspective view of a lysing member/lysing rod with a rectangular cross-section.
FIG. 7d comprises a perspective view of a lysing member/lysing rod with a pentagonal cross-section.
FIG. 7e comprises a perspective view of a lysing member/lysing rod with a hexagonal cross-section.
FIG. 7f comprises a perspective view of a lysing member/lysing rod with a wedge cross-section.
FIG. 7g comprises a perspective view of a lysing member/lysing rod with a half-circle cross-section.
Figures 7H, 7I, 7J, 7K, 7L, 7M, 7N, 7O, 7P, 7Q, 7R, 7S, 7T:
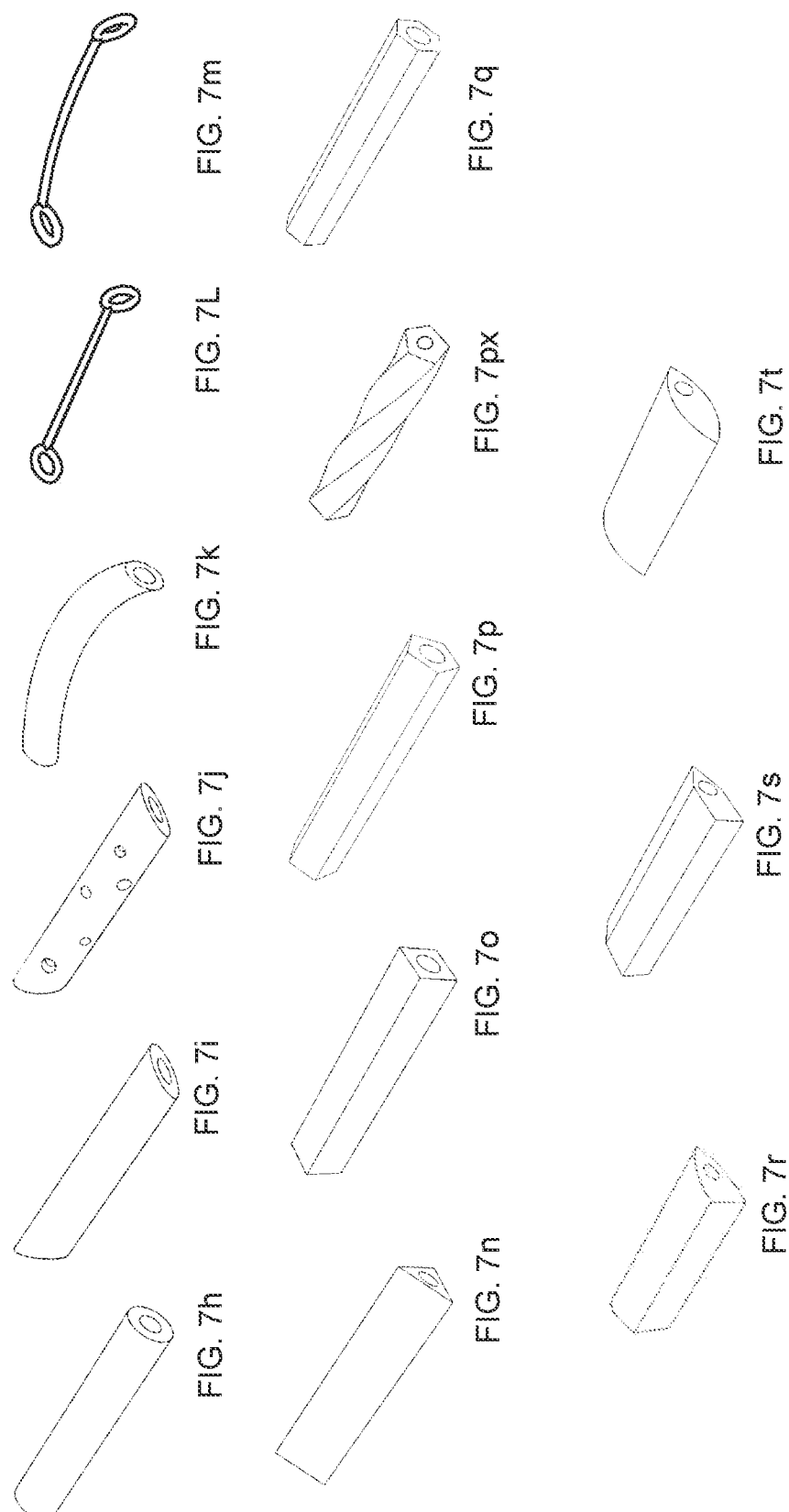
FIG. 7h comprises a perspective view of a spacer to a lysing tip with a hole through its length having a circular cross-section with non-beveled ends.
FIG. 7i comprises a perspective view of a spacer to a lysing tip with a hole through its length having a circular cross-section with beveled ends.
FIG. 7j comprises a perspective view of a spacer to a lysing tip with a hole through its length having a circular cross-section with beveled ends and holes.
FIG. 7k comprises a perspective view of a spacer to a lysing tip with a hole through its length having a circular cross-section arced along its length.
FIG. 7L comprises a perspective view of a spacer to a lysing tip with opposing loops connected by a rod in a relaxed state.
FIG. 7m comprises a perspective view of a spacer to a lysing tip with opposing loops connected by a rod in a stressed state.
FIG. 7n comprises a perspective view of a spacer to a lysing tip with a hole through its length having a triangular cross-section.
FIG. 7o comprises a perspective view of a spacer to a lysing tip with a hole through its length having a rectangular cross-section.
FIG. 7p comprises a perspective view of a spacer to a lysing tip with a hole through its length having a pentagonal cross-section.
FIG. 7q comprises a perspective view of a spacer to a lysing tip with a hole through its length having a hexagonal cross-section.
FIG. 7r comprises a perspective view of a spacer to a lysing tip with a hole through its length having a blade-shaped cross-section with rounded edges.
FIG. 7s comprises a perspective view of a spacer to a lysing tip with a hole through its length having a blade-shaped cross-section with flat edges.
FIG. 7t comprises a perspective view of a spacer to a lysing tip with a hole through its length having a spindle cross-section.
Figures 7A, 7B, 7C, 7D, 7E, 7F, 7G, 7H, 7I, 7J, 7K, 7L, 7M, 7N, 7O, 7P, 7Q, 7R:
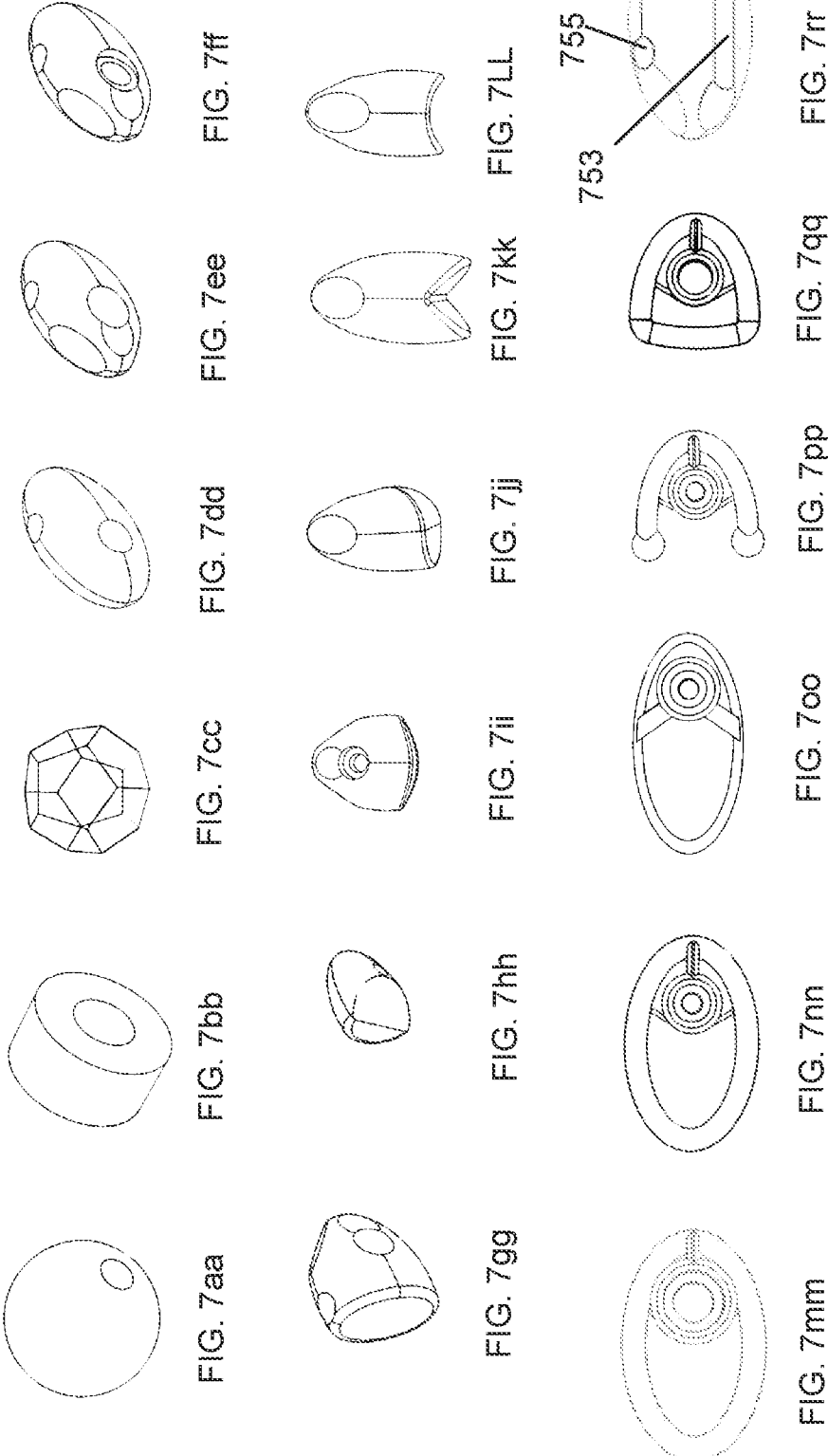

FIG. 7rr is a side perspective view of a bead comprising a slot configured to engage a lysing member.

FIG. 7ss is a perspective view of 3 beads of differing lengths having an elongated shaped with curved ends.

FIG. 7tt is a perspective view of 3 beads of differing lengths having an elongated shaped with flattened ends.

FIG. 7uu is a perspective view of 4 beads of differing lengths having an alternative shape.

FIG. 7vv is a perspective view of 4 beads of differing lengths having a shape that is hollowed out along an axis.

FIG. 7ww is a perspective view of 4 elongated beads having an alternative shape.

FIG. 7xx is a perspective view of 4 beads of differing lengths having an alternative shape that is curved ends.

FIG. 7yy is a perspective view of 4 beads of differing lengths having a curved, elongated shape with flattened sides.

FIG. 7zz is a perspective view of a bead comprising surface irregularities.

FIG. 7zzz is a perspective view of a bead comprising surface regularities.

Figures 8A, 8B:
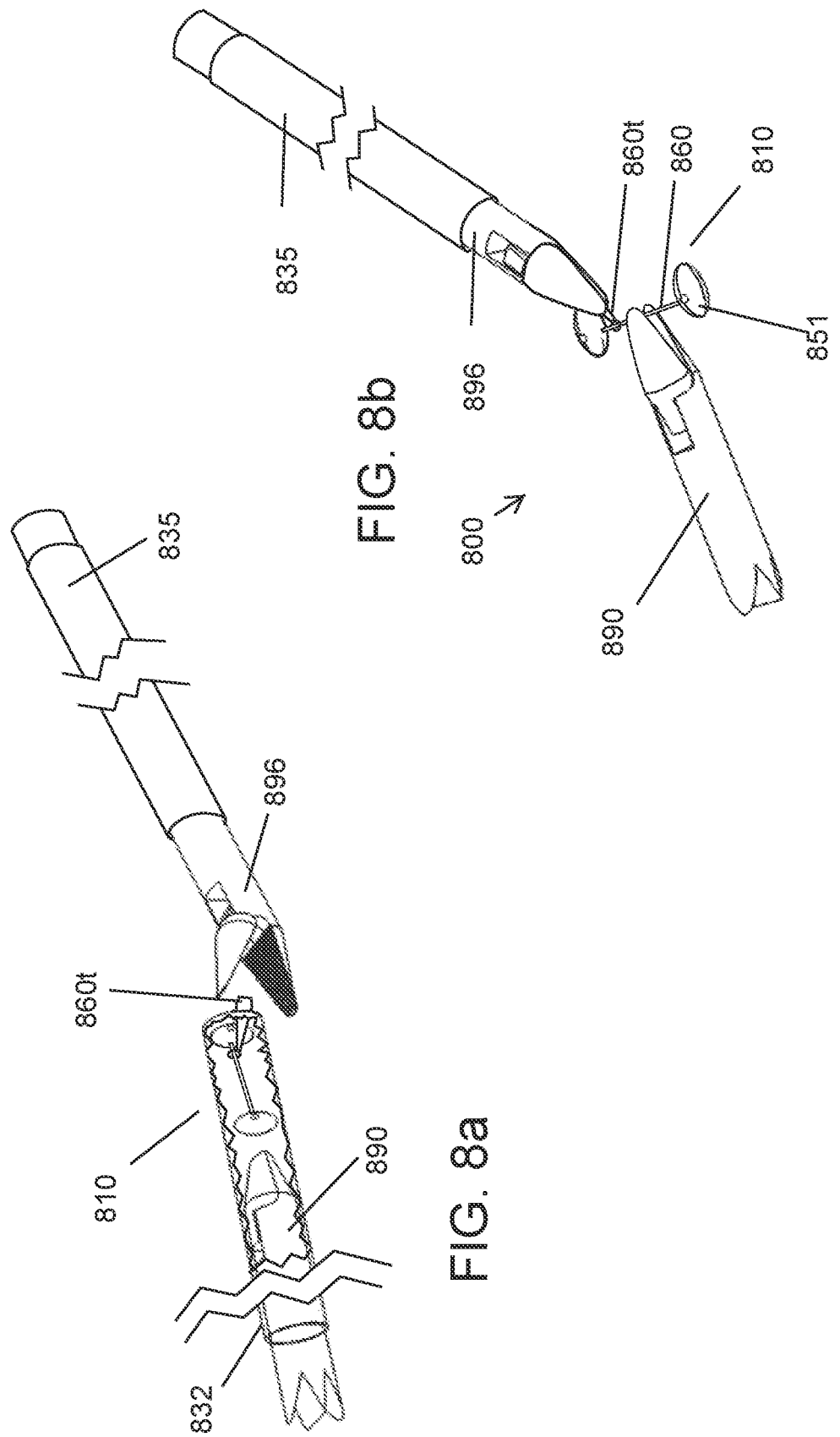

FIG. 8a is a partial breakaway view of the delivery of lysing tip and grasping/control instrument inside a body, said lysing tip to be received and held by a second instrument until the grasping/control instrument grasps and controls lysing tip for the surgical procedure.

FIG. 8b is a perspective view of the interaction between a lysing tip, its grasping/control instrument, and a temporary holding/grasping instrument.

Figures 8C, 8D:
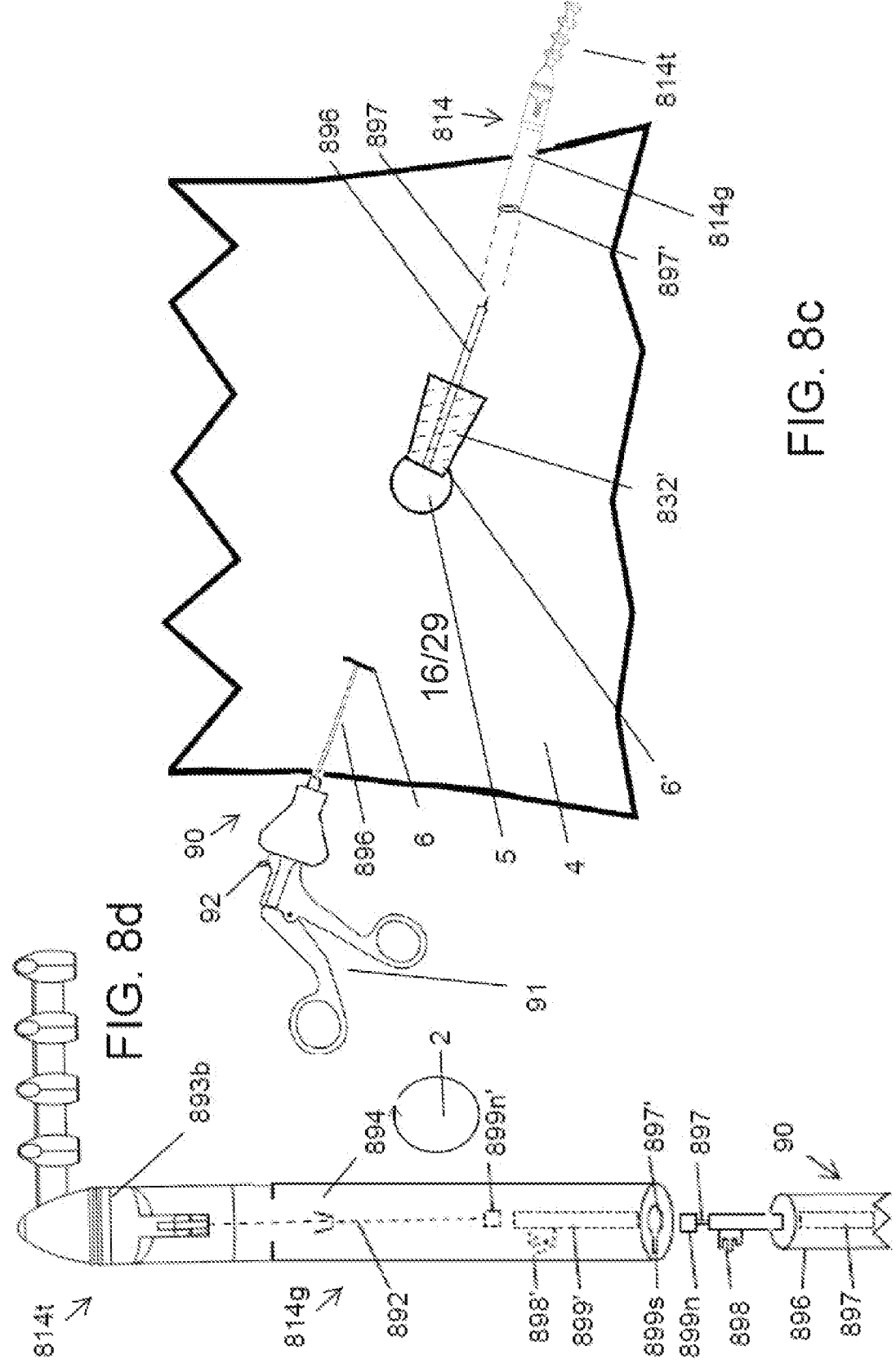

FIG. 8c is a view of the abdomen depicting the construction of a surgical device to be used therein.

FIG. 8d is a top plan view of a modular lysing tip depicting internal components of a locking mechanism.

FIG. 9a is a perspective view of an embodiment of a system for delivery of a bipolar lysing tip in the treatment configuration with sleeve positioned distally.

FIG. 9b is a perspective view of the embodiment depicted in FIG. 9a with jaw open and sleeve positioned proximally.

FIG. 9c is a front view of the embodiment depicted in FIG. 9a.

FIG. 9d is an upper view of the lysing tip coupled with jaws of the embodiment depicted in FIG. 9a.

FIG. 9e is a perspective view of the bipolar lysing tip of the embodiment depicted in FIG. 9a.

FIG. 9f is a perspective view of an electrode of the lysing tip of the embodiment depicted in FIG. 9a.

FIG. 9g is a perspective view of the opposing electrode to that depicted in FIG. 9f.

FIG. 9h is a perspective view of the bipolar lysing tip of the embodiment depicted in FIG. 9a with cross member being transparent exposing lysing segments and seated in lower jaw with upper jaw removed.

FIG. 9i is a perspective view of the bipolar lysing tip of the embodiment depicted in FIG. 9a with upper jaw removed and cross member seated in lower jaw showing exposure of lysing segment post.

FIG. 9j is a cross sectional view of the distal end of the embodiment depicted in FIG. 9a at the location shown in FIG. 9c.

FIG. 9k is a cross sectional view of the distal end of the embodiment depicted in FIG. 9a at the location shown in FIG. 9c.

FIG. 9L is a perspective view of the lower jaw cover of the embodiment depicted in FIGS. 9j and 9k.

FIG. 10a is a top plan view of a 2-bead lysing instrument.

FIG. 10b is a top plan view of the embodiment depicted in FIG. 10a.

FIG. 10c is a perspective view of the embodiment depicted in FIG. 10a.

FIG. 10d is a top view of the electrode of the embodiment depicted in FIG. 10a.

FIG. 10e is a perspective view of the nonconductive body of the embodiment depicted in FIG. 10a.

FIG. 10f is a side elevation view of the lysing tip of the embodiment depicted in FIG. 10a.

FIG. 10g is a cross-sectional view of bottom half of the embodiment depicted in FIG. 10a taken along line 10g-10g of FIG. 10f.

Figures 10H, 10I, 10J, 10K, 10L:
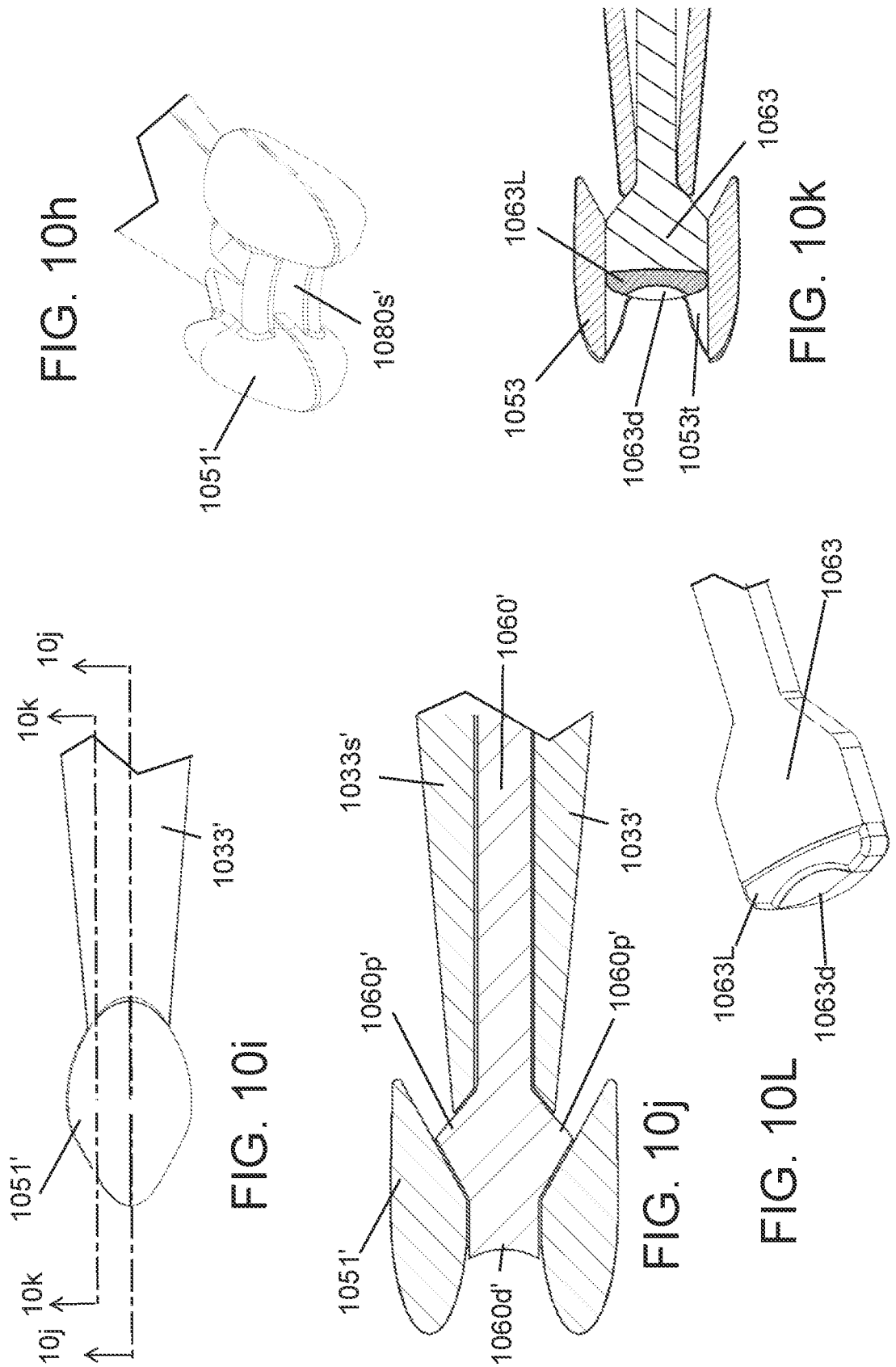

FIG. 10h is a perspective view of the nonconductive body of an alternative embodiment.

FIG. 10i is a side elevation view of the lysing tip of the alternative embodiment depicted in FIG. 10h.

FIG. 10j is a cross-sectional view of the bottom half of the embodiment depicted in FIG. 10h taken along line 10j-10j in FIG. 10i with an electrode inserted within the nonconductive body.

FIG. 10k is a cross-sectional view taken along line 10k-10k of FIG. 10i of the bottom half of an alternative embodiment with a modified electrode tip.

FIG. 10L is a perspective view of the modified electrode of the alternative embodiment depicted in FIG. 10k.

FIG. 11a is a perspective view of a 3-bead lysing instrument according to some embodiments.

FIG. 11b is a perspective view of the lysing tip of the embodiment depicted in FIG. 11a.

FIG. 11c is an exploded view of the lysing tip of the embodiment depicted in FIG. 11a.

FIG. 11d is a side elevation view of the lysing tip of the embodiment depicted in FIG. 11a.

FIG. 11e is a cross-sectional view of the lysing tip of the embodiment depicted in FIG. 11a taken along line 11e-11e in FIG. 11d.

Figures 11F, 11G, 11H, 11I:
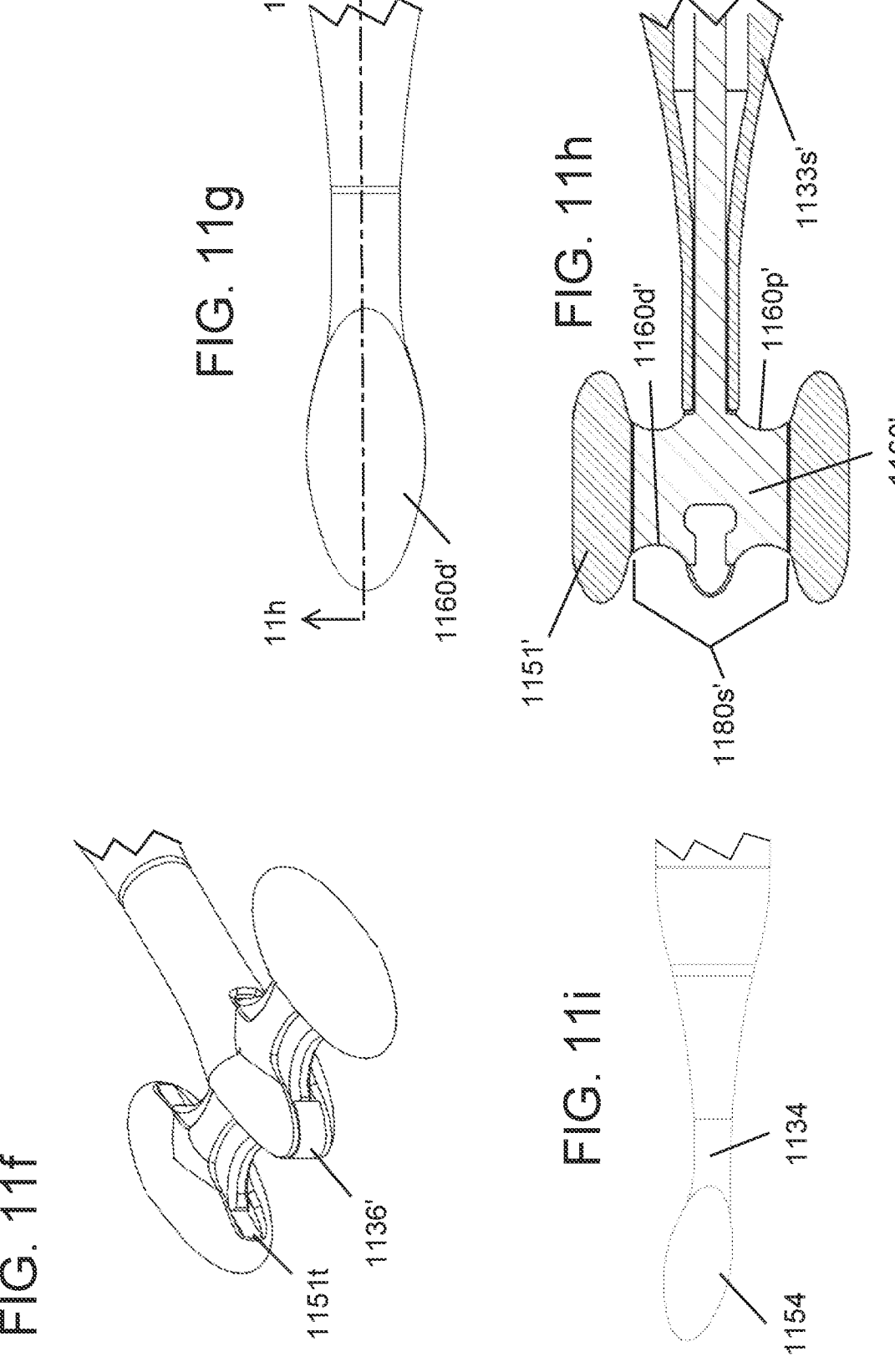

FIG. 11f is a perspective view of an alternative embodiment of a lysing tip.

FIG. 11g is a side elevation view of an additional alternative embodiment of a lysing tip comprising beads lacking a tunnel.

FIG. 11h is a cross-sectional view of the embodiment of FIG. 11g taken along line 11h-11h in FIG. 11g.

FIG. 11i is a side elevation view of an additional alternative embodiment of a lysing tip wherein the beads of the lysing tip are tilted relative to the axis of the instrument shaft.

Figures 12, 13A, 13B, 13C:
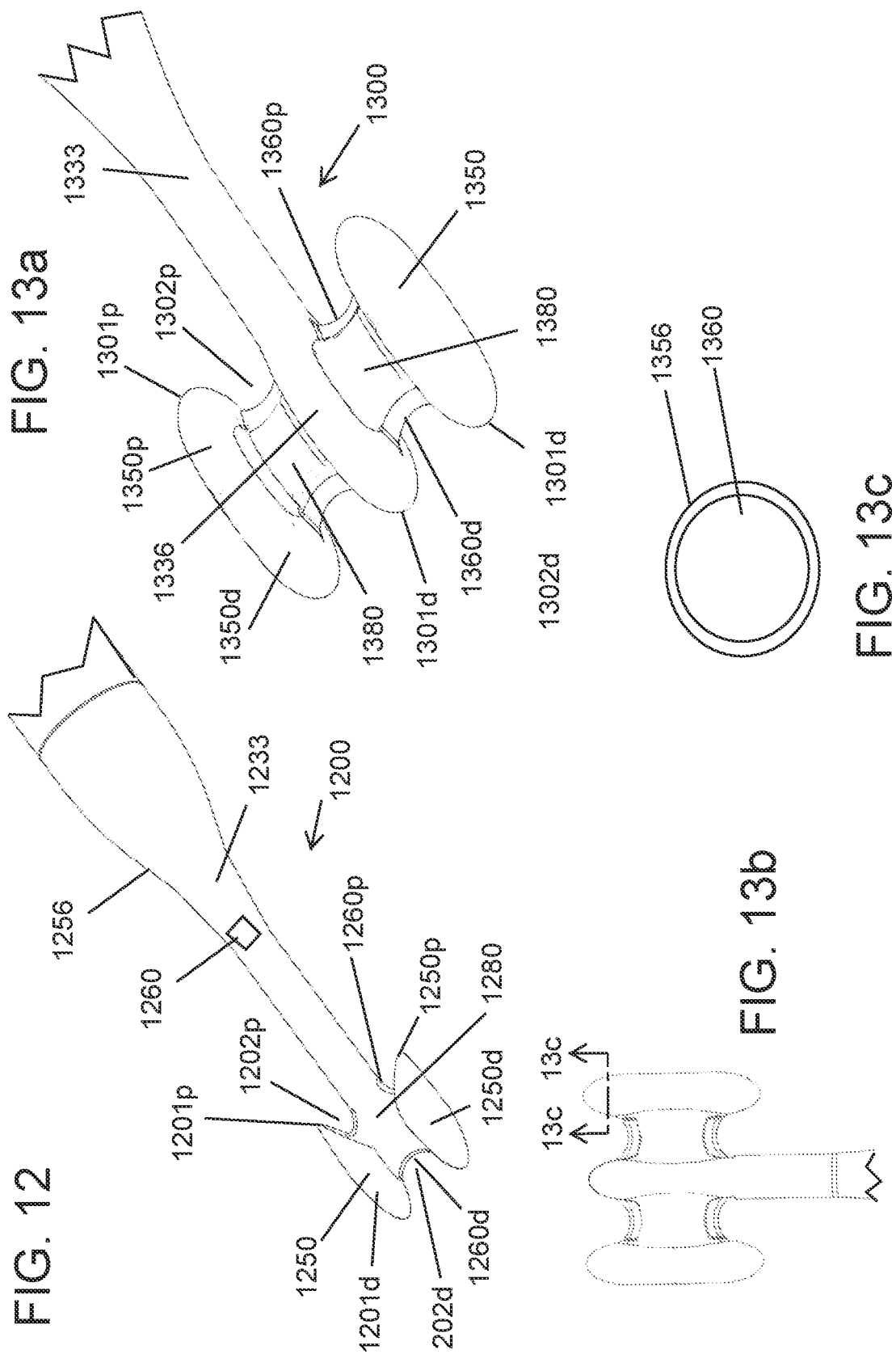

FIG. 12 is a perspective view of a 2-bead lysing tip comprising a coated, unibody conductor according to other embodiments.

FIG. 13a is a perspective view of a 3-bead lysing tip comprising a coated, unibody conductor according to other embodiments.

FIG. 13b is a top plan view of the embodiment depicted in FIG. 13a.

FIG. 13c is a cross-sectional view taken along line 13c-13c in FIG. 13b.

Figures 14A, 14B, 14C, 14D:
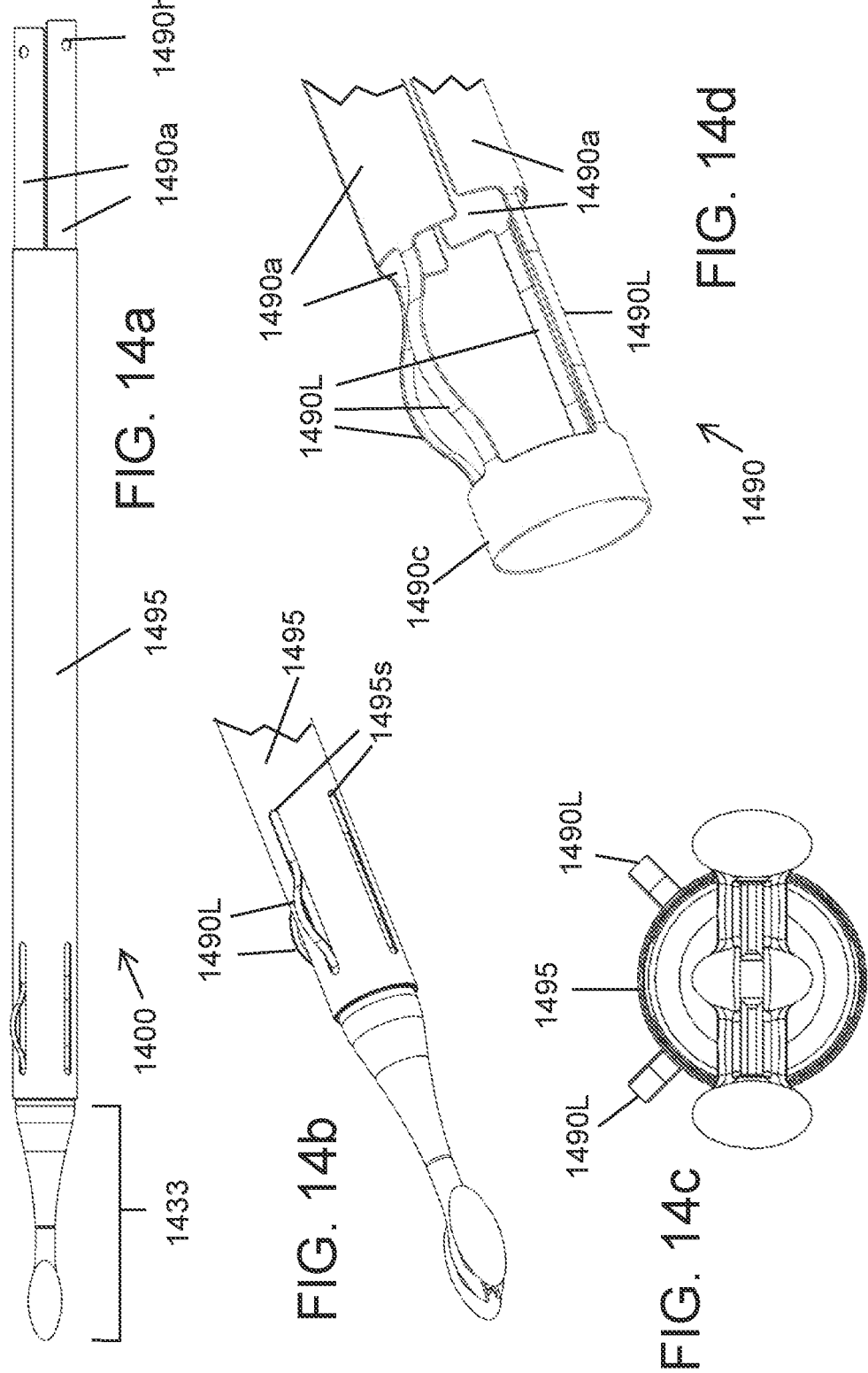

FIG. 14a is a side elevation view of an embodiment of a lysing instrument comprising a deflection system.

FIG. 14b is a perspective view of the distal end of the lysing instrument depicted in FIG. 14a.

FIG. 14c is a front elevation view of the embodiment depicted in FIG. 14a.

FIG. 14d is a perspective view of the deflector sleeve of the embodiment depicted in FIG. 14a.

Figures 15A, 15B, 15C, 15D:
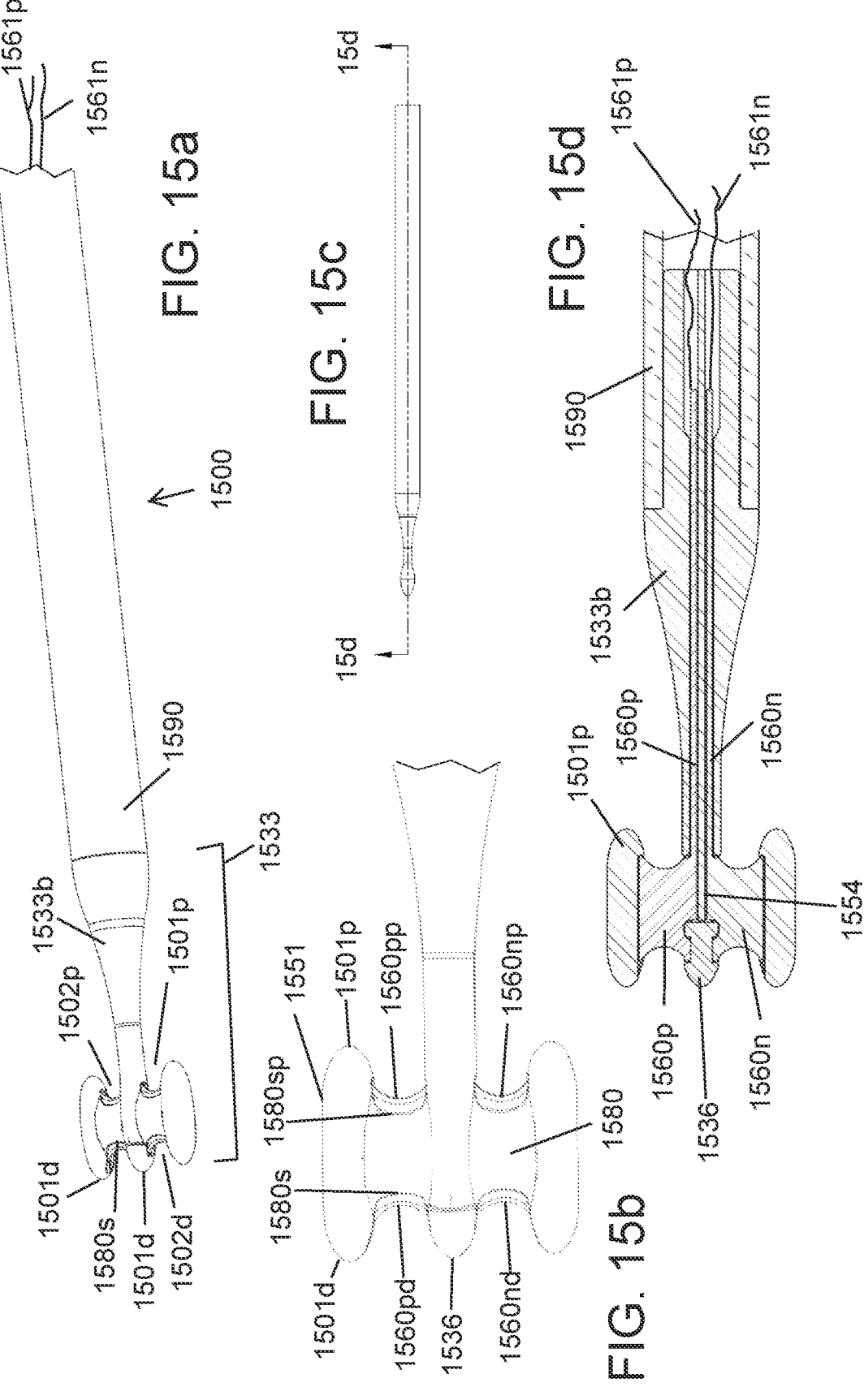

FIG. 15a is a perspective view of an embodiment of a bipolar lysing instrument.

FIG. 15b is a top plan view of the lysing tip of the embodiment of FIG. 15a.

FIG. 15c is a side elevation view of the embodiment of FIG. 15a.

FIG. 15d is a cross-sectional view taken along line 15d-15d in FIG. 15c.

Figures 16A, 16B, 16C, 16D, 16E, 16F:
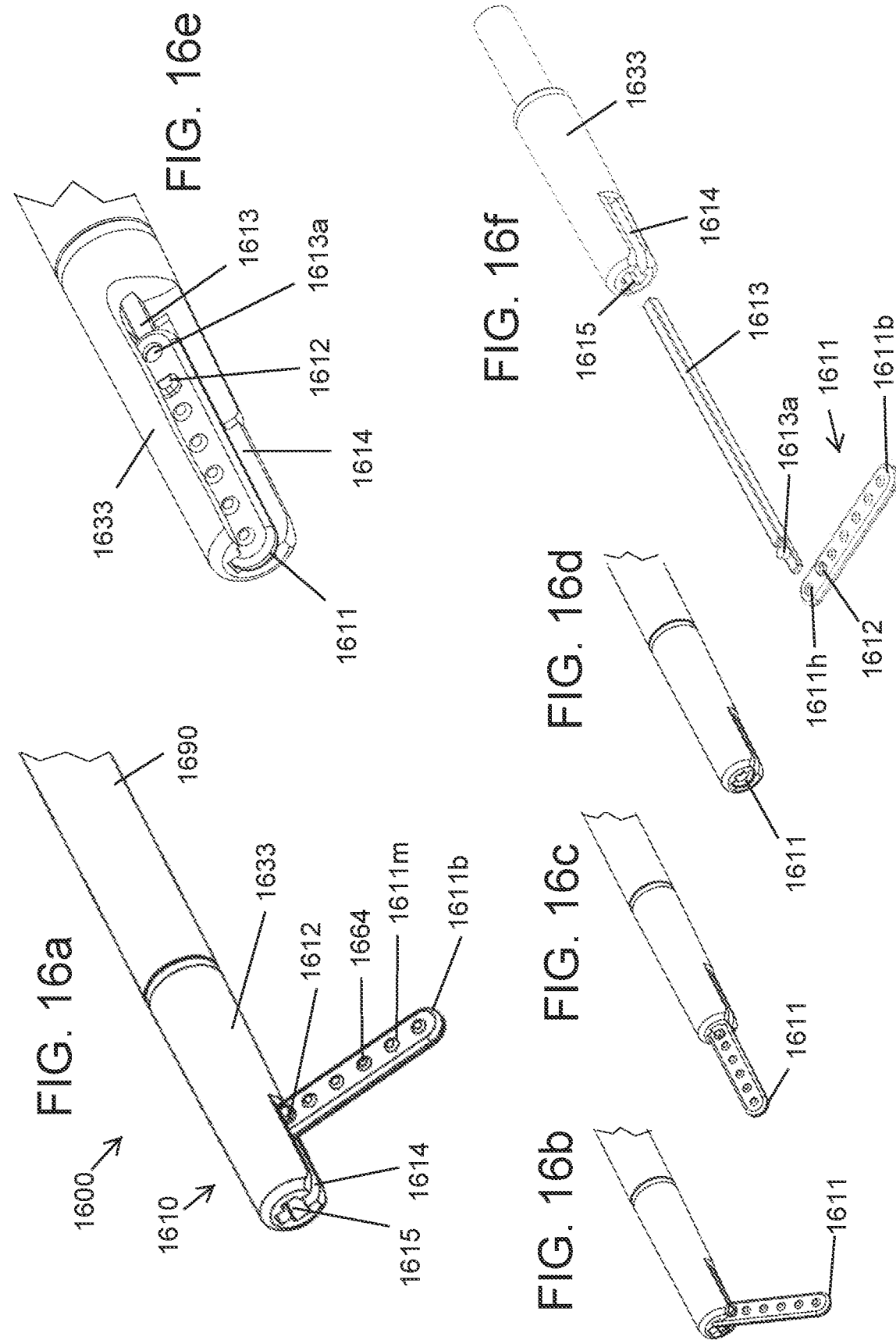

FIG. 16a is a perspective view of a tissue modification instrument in its treatment configuration.

FIG. 16b is a perspective view of the embodiment depicted in FIG. 16a in an intermediate configuration.

FIG. 16c is a perspective view of the embodiment depicted in FIG. 16a in an additional intermediate configuration.

FIG. 16d is a is a perspective view of the embodiment depicted in FIG. 16a in its fully retracted configuration.

FIG. 16e is a cut away view of the distal end of the embodiment in FIG. 16a in its fully retracted configuration.

FIG. 16f is an exploded view of the embodiment depicted in FIG. 16a.

Figures 17A, 17B, 17C, 17D, 17E:
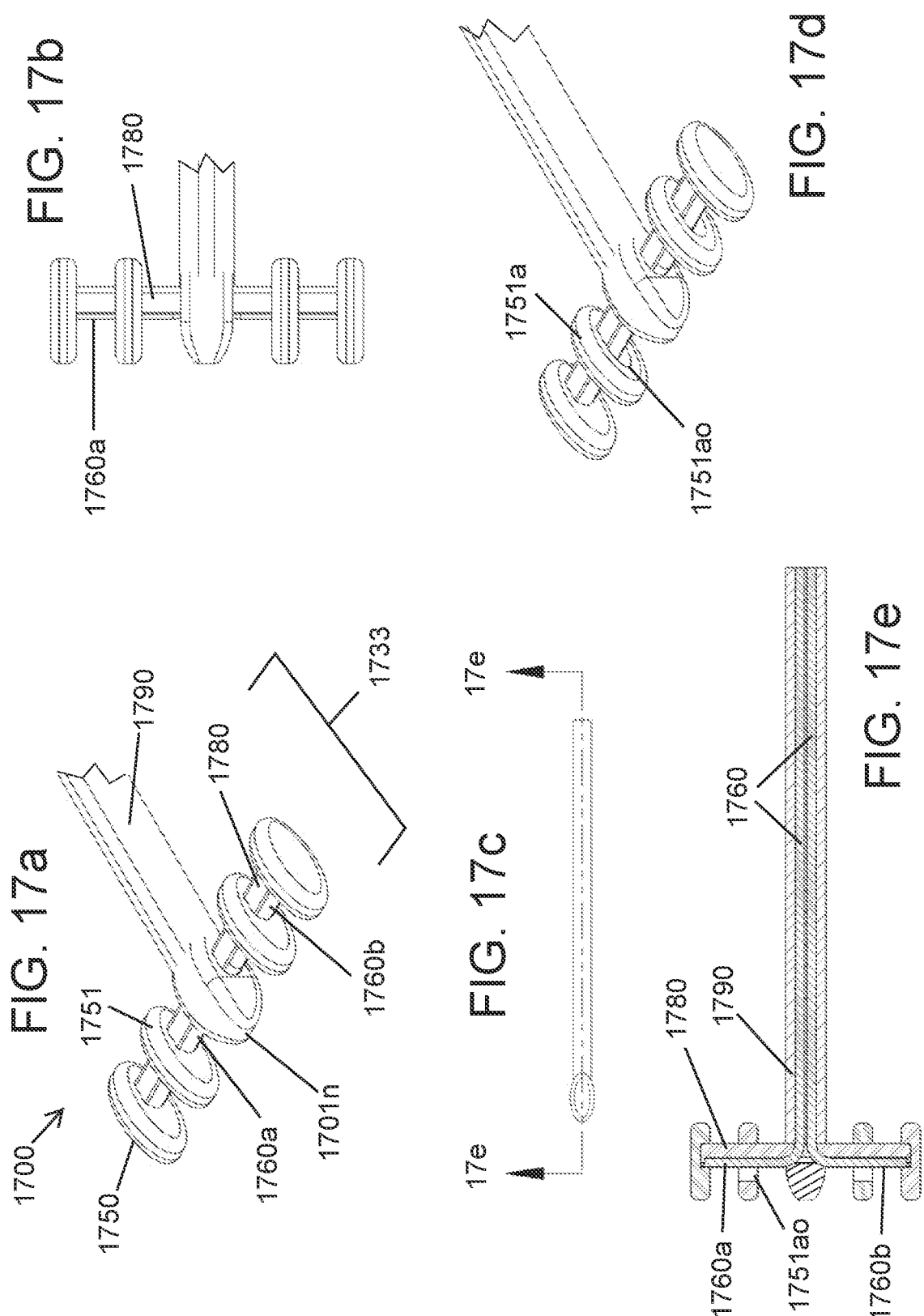

FIG. 17a is a perspective view of alternative embodiment of a lysing tip.

FIG. 17b is a top plan view of the embodiment depicted in FIG. 17a.

FIG. 17c is a side elevation view of an alternative embodiment of a lysing tip wherein the beads adjacent to the nose of the lysing instrument comprise openings adjacent the lysing segment/electrode.

FIG. 17d is a perspective view of the embodiment depicted in FIG. 17c.

FIG. 17e is a cross-sectional view taken along line 17e-17e in FIG. 17c.

FIG. 18a is a perspective view of an alternative embodiment of a lysing tip.

FIG. 18b is a top plan view of the embodiment depicted in FIG. 18a.

FIG. 19a is a perspective view of an alternative embodiment of a lysing tip.

FIG. 19b is a top plan view of the embodiment depicted in FIG. 19a.

FIG. 20a is a perspective view of an alternative embodiment of a lysing tip.

FIG. 20b is a top plan view of the embodiment depicted in FIG. 20a.

Figures 21A, 21B, 21C:
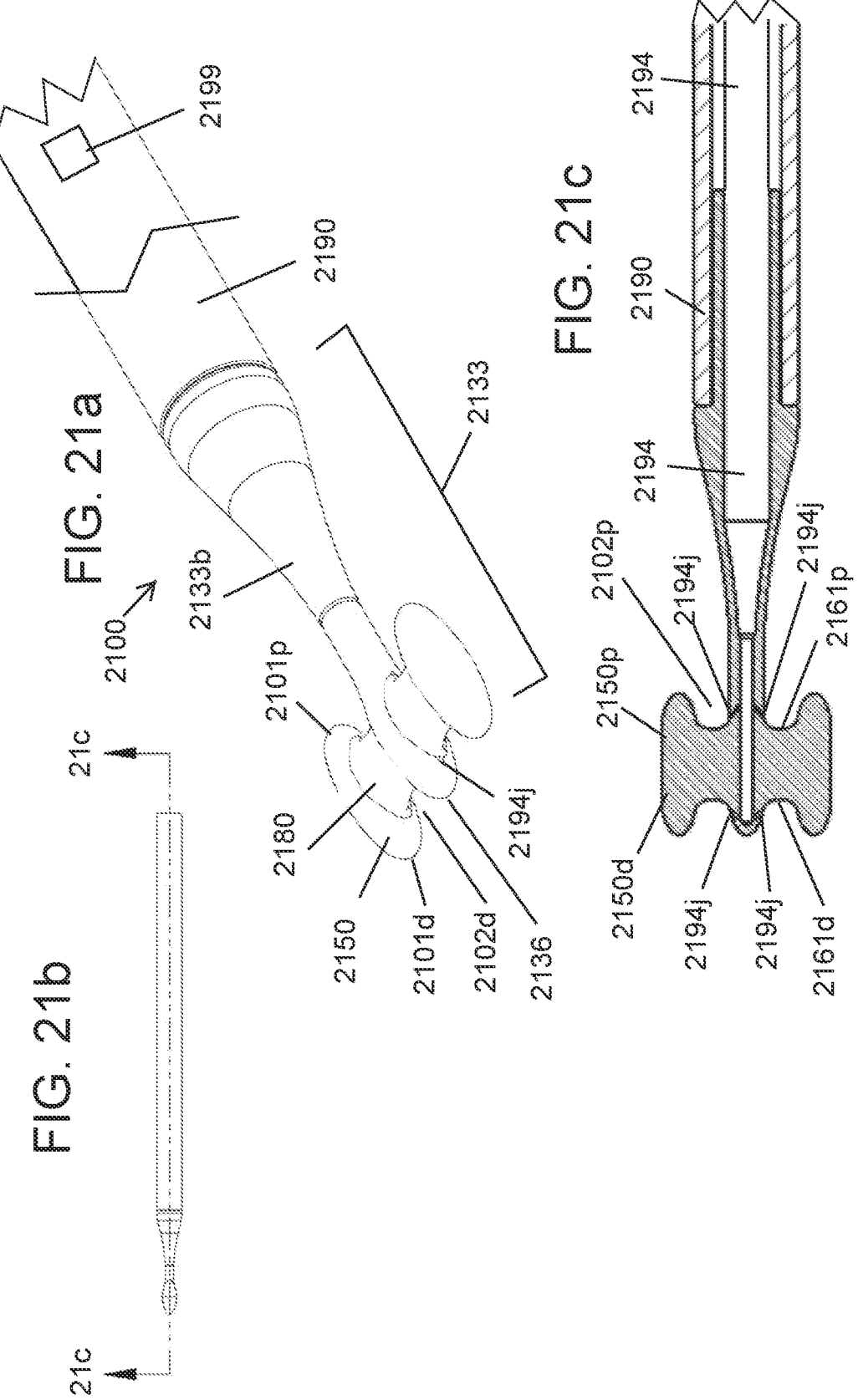

FIG. 21a is a perspective view another alternative embodiment of a lysing tip.

FIG. 21b is a side elevation view of the embodiment depicted in FIG. 21a.

FIG. 21c is a cross-sectional view taken along line 21c-21c in FIG. 21b.

FIG. 22a is a perspective view of an embodiment of a 2-bead lysing tip with a tissue deflecting strut.

FIG. 22b is a side elevation view of the lysing tip of the embodiment depicted in FIG. 22a.

FIG. 22c is a cross-sectional view of the top half of the embodiment depicted in FIG. 22a taken along line 22c-22c—in FIG. 22b.

FIG. 22d is a closeup rear perspective view of the tissue deflecting strut of the embodiment depicted in FIG. 22a.

FIG. 22e is a closeup, side, rear perspective view of the tissue deflecting strut of the embodiment depicted in FIG. 22a.

Figures 23A, 23B, 23C, 23D, 23E:
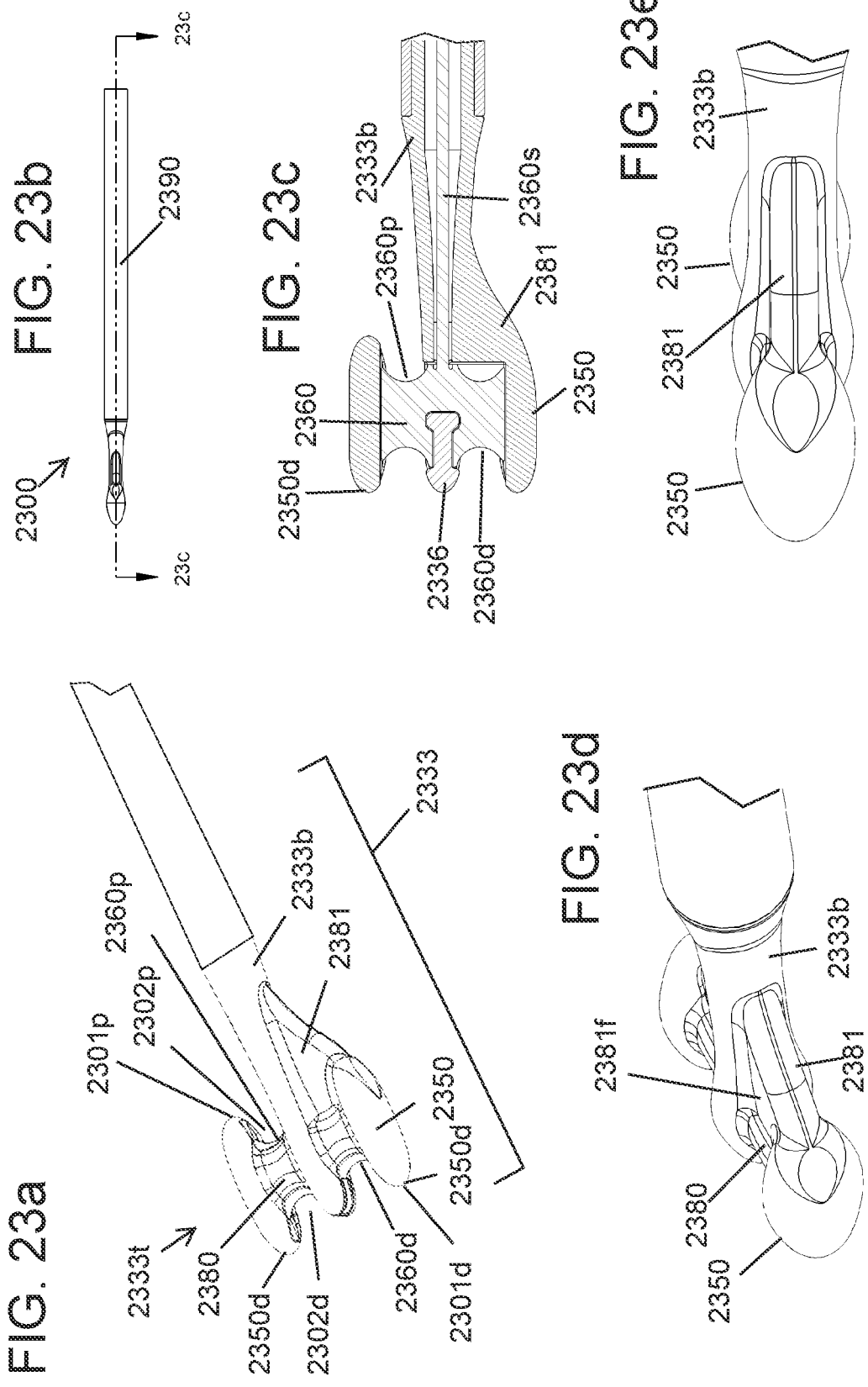

FIG. 23a is a perspective view of an embodiment of a 3-bead lysing tip with a tissue deflecting strut.

FIG. 23b is a side elevation view of the lysing tip of the embodiment depicted in FIG. 23a.

FIG. 23c is a cross-sectional view of the bottom half of the embodiment depicted in FIG. 23a taken along line 23c-23c—in FIG. 23b.

FIG. 23d is closeup rear perspective view of the tissue deflecting strut of the embodiment depicted in FIG. 23a.

FIG. 23e is a closeup side, rear perspective view of the tissue deflecting strut of the embodiment depicted in FIG. 23a.

Figures 24, 25A, 25B, 25C:
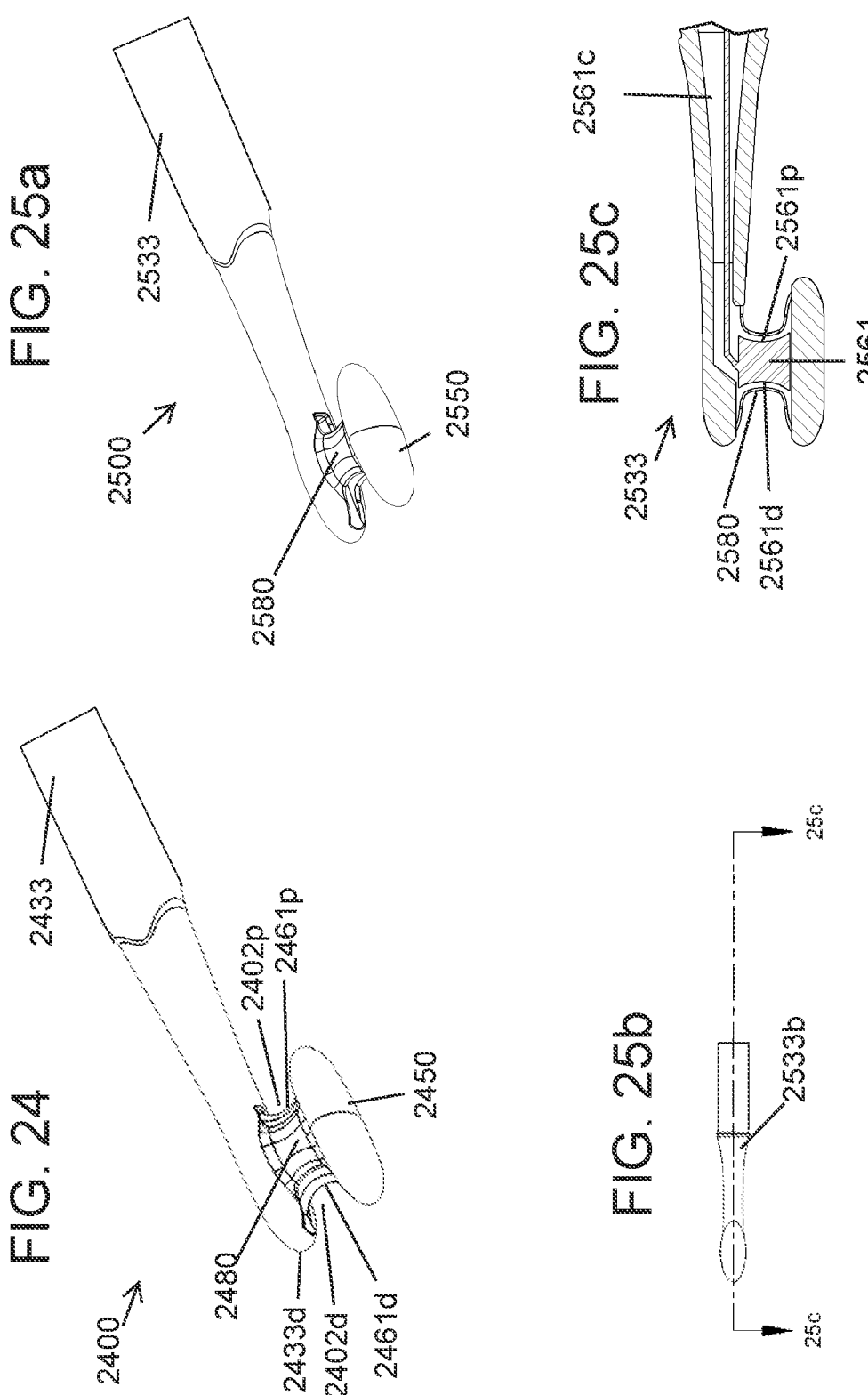

FIG. 24 is a perspective view of an embodiment of a single-bead lysing tip.

FIG. 25a is a perspective view of an alternative embodiment of a single-bead lysing tip with an electrode recessed completely within a strut from the shaft to the bead.

FIG. 25b is a side elevation view of the lysing tip of the embodiment depicted in FIG. 25a.

FIG. 25c is a cross-sectional view taken along line 25c-25c in FIG. 25b.

Figures 26A, 26B, 26C, 26D, 26E:
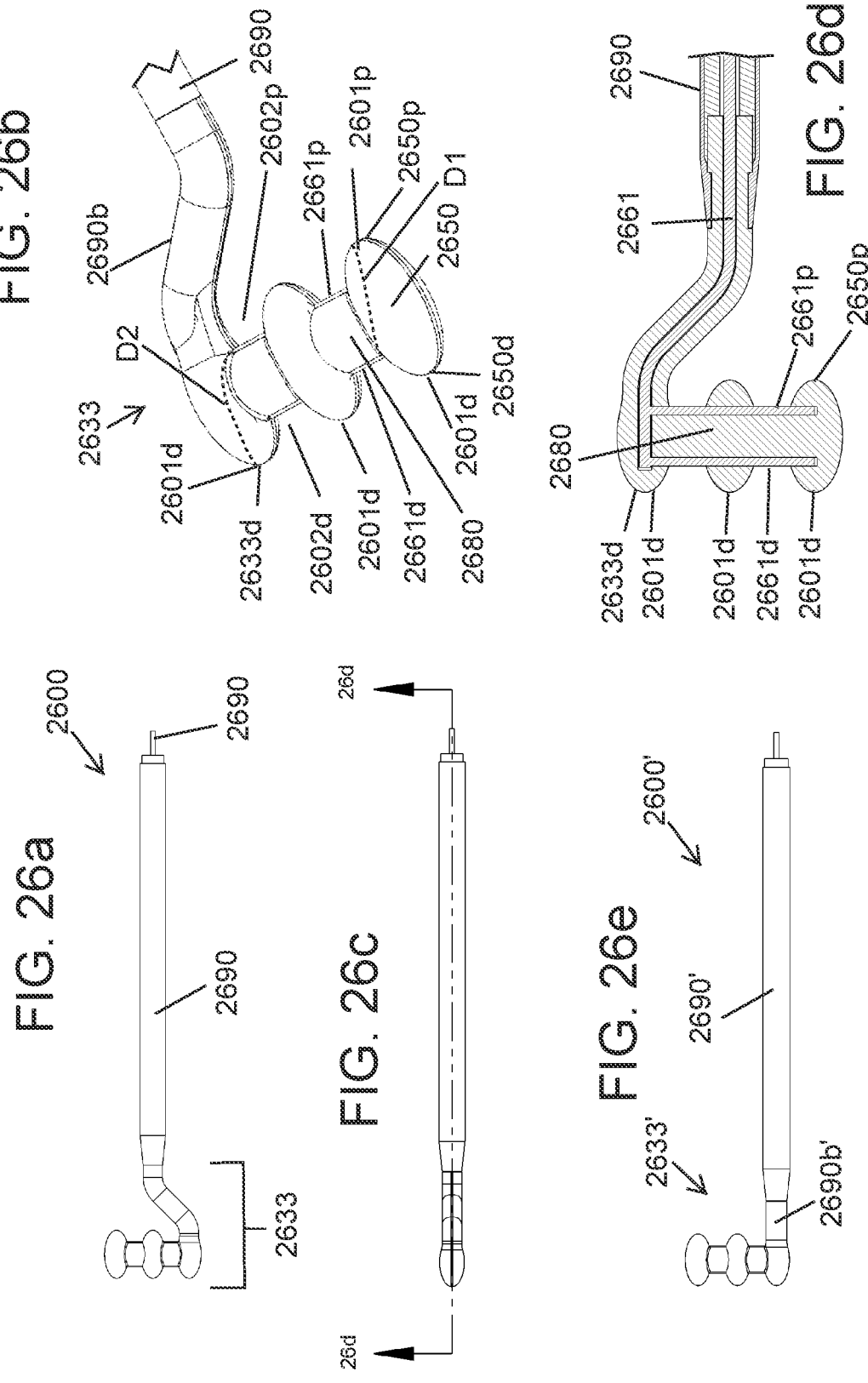

FIG. 26a is a top plan view of an embodiment of a lysing instrument comprising angled portions.

FIG. 26b is a perspective view of the embodiment depicted in FIG. 26a.

FIG. 26c is a side elevation view of the embodiment depicted in FIG. 26a.

FIG. 26d is a cross-sectional view of the top half of the embodiment depicted in FIG. 26a taken along line 26d-26d—in FIG. 26b.

FIG. 26e is an alternative embodiment of the lysing instrument depicted in FIG. 26a in which the shaft is not angled or curved.

Figures 27A, 27B, 27C:
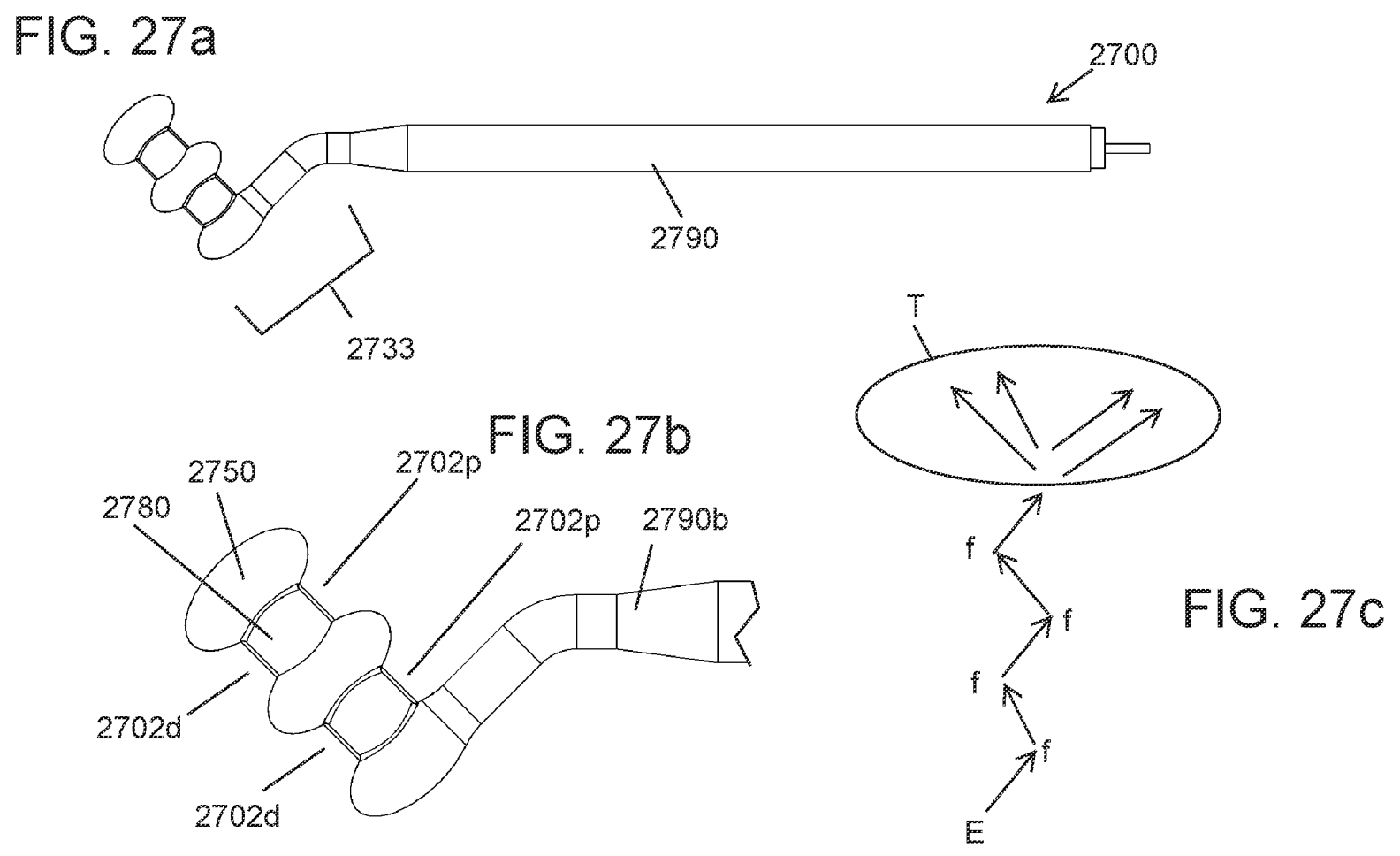

FIG. 27a is a top plan view of an alternative embodiment of lysing instrument comprising an angled shaft and an angled lysing tip.

FIG. 27b is a closeup perspective view of the lysing tip of embodiment depicted in FIG. 27a.

FIG. 27c is an illustrated depiction of a potential tissue dissection path that may be employed with the instrument depicted in FIG. 27a.

Figures 28A, 28B, 29A, 29B:
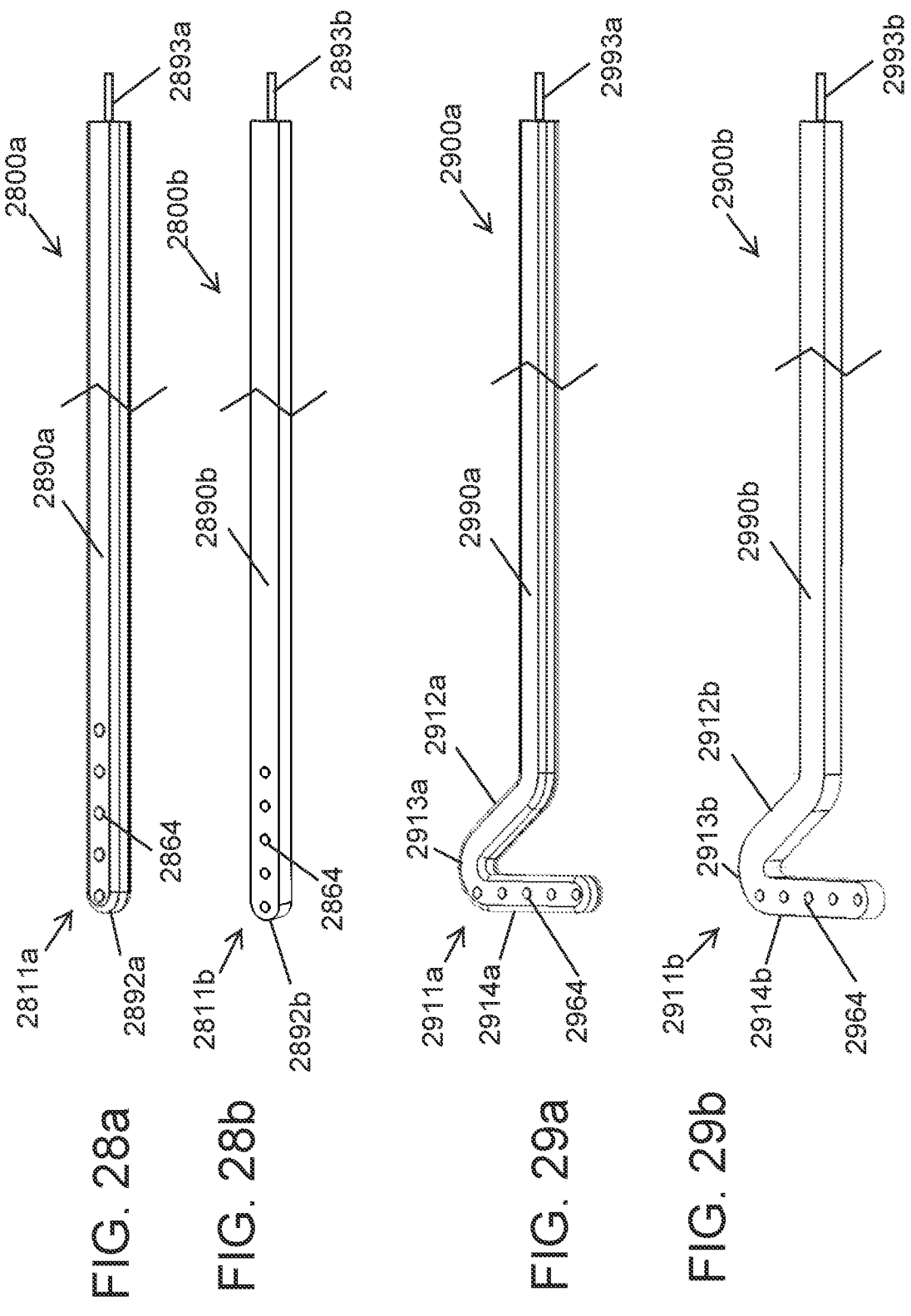

FIG. 28a is a perspective view of a tissue modification device that is comprised of an axial treatment tip with rounded edges.

FIG. 28b is a perspective view of a tissue modification device that is comprised of an axial treatment tip with edges that are not rounded.

FIG. 29a is a perspective view of a tissue modification device comprising an anfractuous treatment tip that extends perpendicular to the shaft and has rounded edges.

FIG. 29b is a perspective view of a tissue modification device comprising an anfractuous treatment tip that extends perpendicular to the shaft with that are not rounded.

Figures 30, 31:
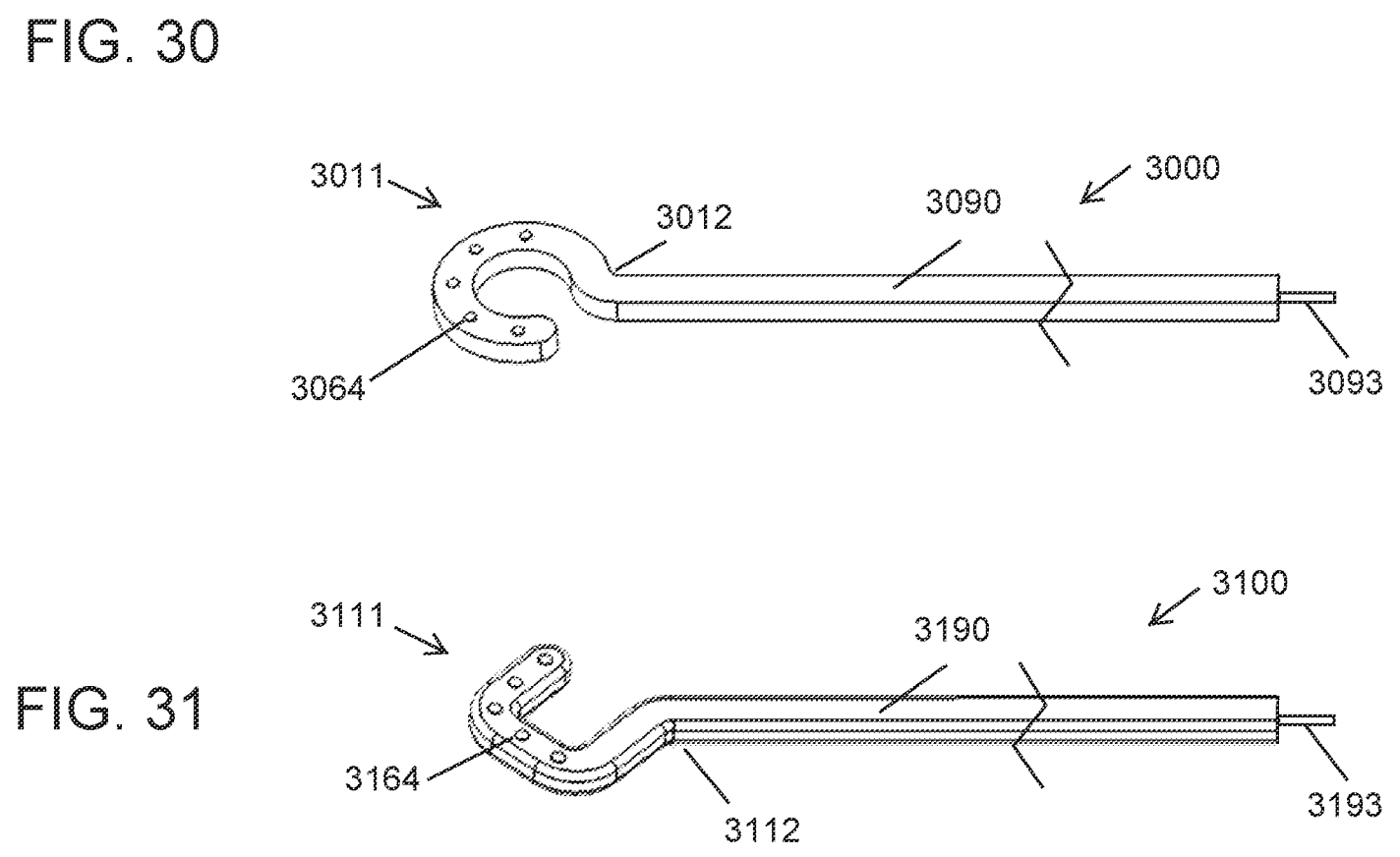

FIG. 30 is a perspective view of a tissue modification device with a continuously curved treatment tip.

FIG. 31 is a perspective view of a tissue modification device comprising an anfractuous treatment tip having a pointed distal end.

Figure 32:
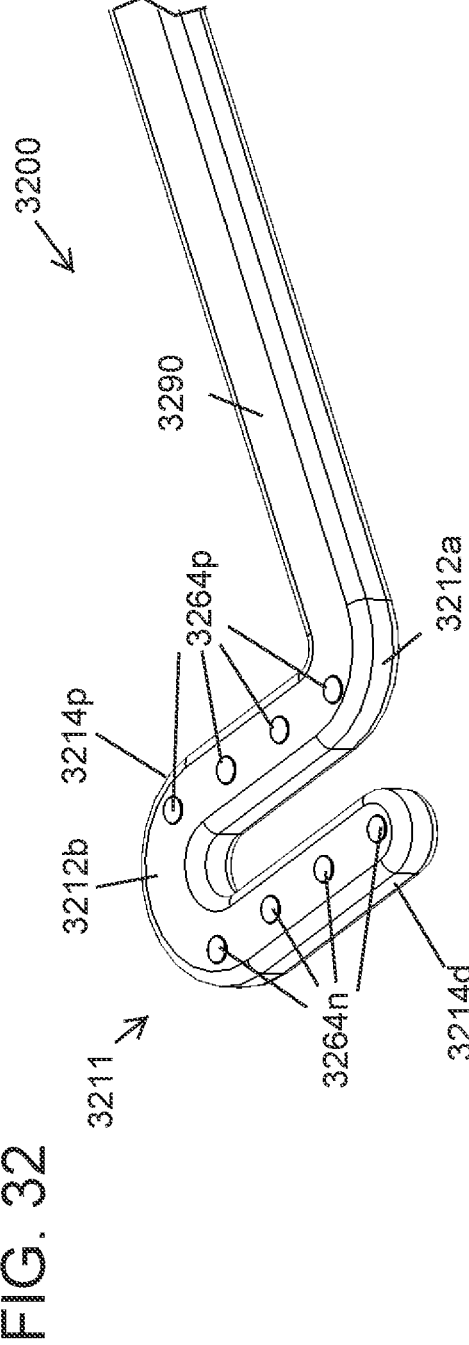

FIG. 32 is a perspective view of a bipolar TMT device.

Figures 33A, 33B, 33C, 33D, 34A, 34B, 34C, 34D, 35A, 35B, 35C, 35D, 36A, 36B, 36C, 36D:
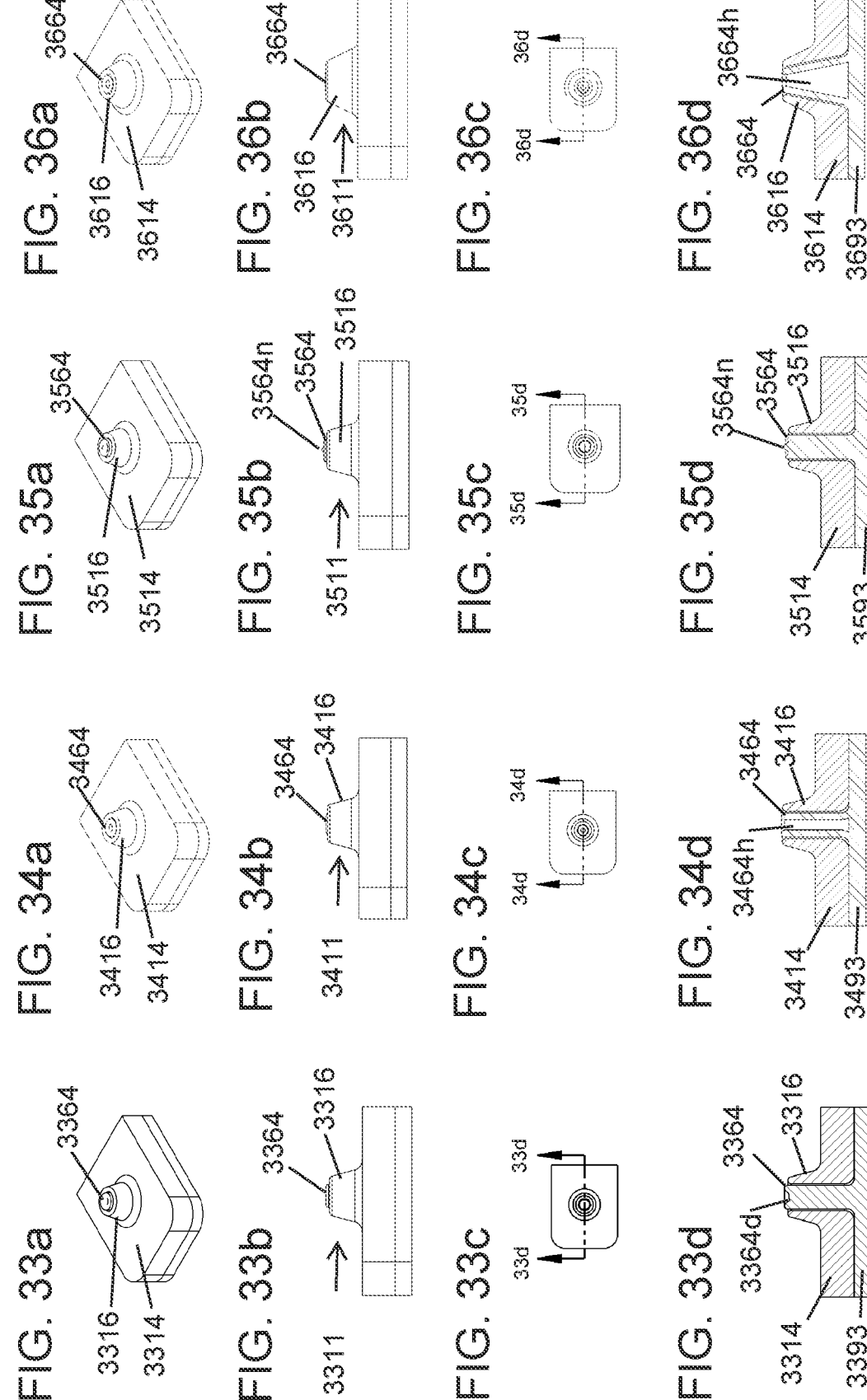

FIG. 33a is a perspective view of an electrode termini with a depression.

FIG. 33b is a side elevation view of the embodiment depicted in FIG. 33a.

FIG. 33c is a top plan view of the embodiment depicted in FIG. 33a.

FIG. 33d is a cross sectional view taken along line 33d-33d, in FIG. 33c.

FIG. 34a is a perspective view of an electrode termini with a cylinder with a hole.

FIG. 34b is a side elevation view of the embodiment depicted in FIG. 34a.

FIG. 34c is a top plan view of the embodiment depicted in FIG. 34a.

FIG. 34d is a cross sectional view taken along line 34d-34d, in FIG. 34c.

FIG. 35a is a perspective view of an electrode termini with a dome/projecting island in the center of the dome.

FIG. 35b is a side elevation view of the embodiment depicted in FIG. 35a.

FIG. 35c is a top plan view of the embodiment depicted in FIG. 35a.

FIG. 35d is a cross sectional view taken along line 35d-35d, in FIG. 35c.

FIG. 36a is a perspective view of an electrode termini with a conical conductive core with a conical hole/opening.

FIG. 36b is a side elevation view of the embodiment depicted in FIG. 36a.

FIG. 36c is a top plan view of the embodiment depicted in FIG. 36a.

FIG. 36d is a cross sectional view taken along line 36d-36d, in FIG. 36c.

Figure 37:
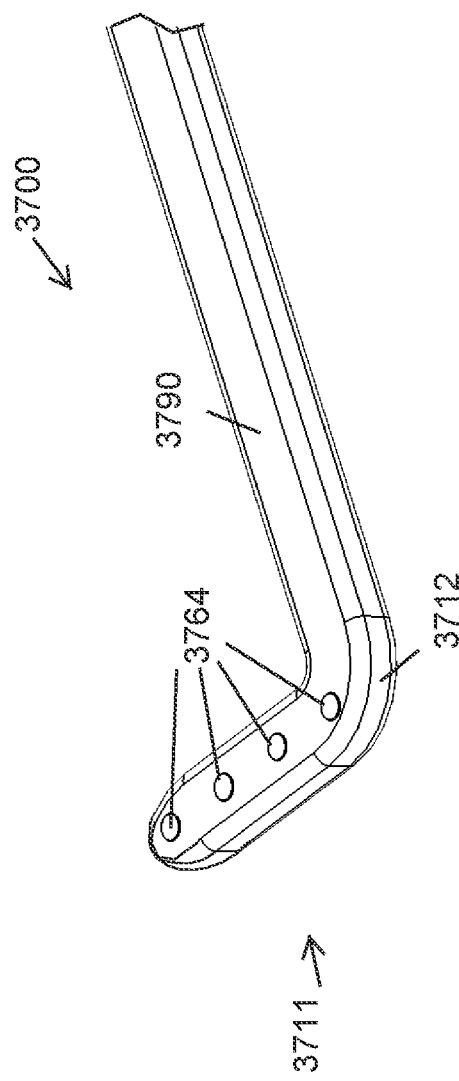

FIG. 37 is an elevation view of a TMT instrument with a shaft comprising a right angle relative to the shaft.

Figure 38:
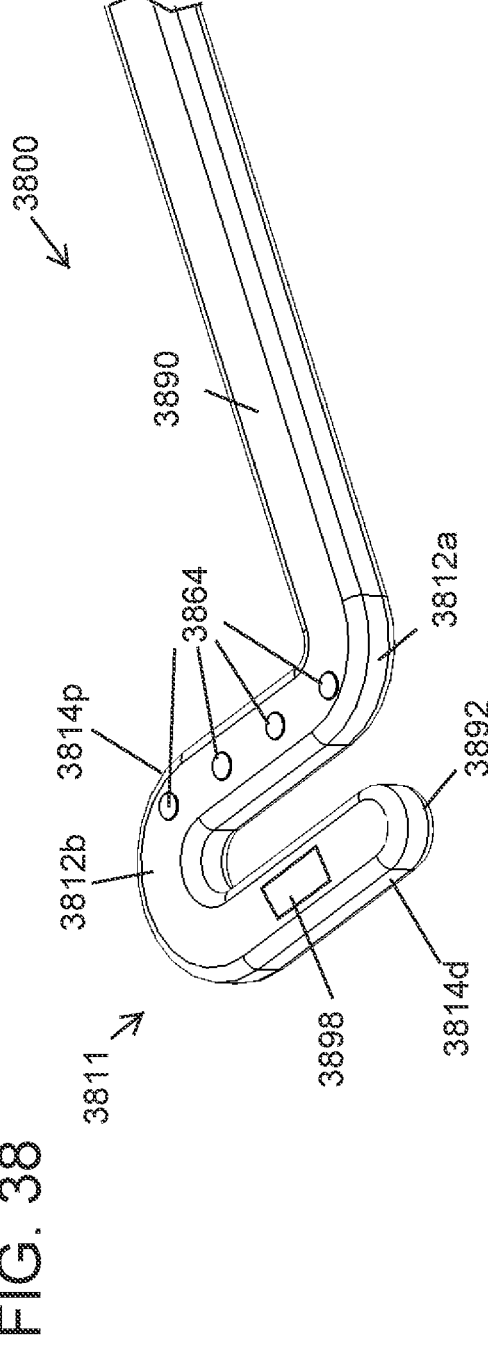

FIG. 38 is a perspective view of a TMT instrument comprising a treatment window on one portion and a sensor window on another portion.

Figure 39B:
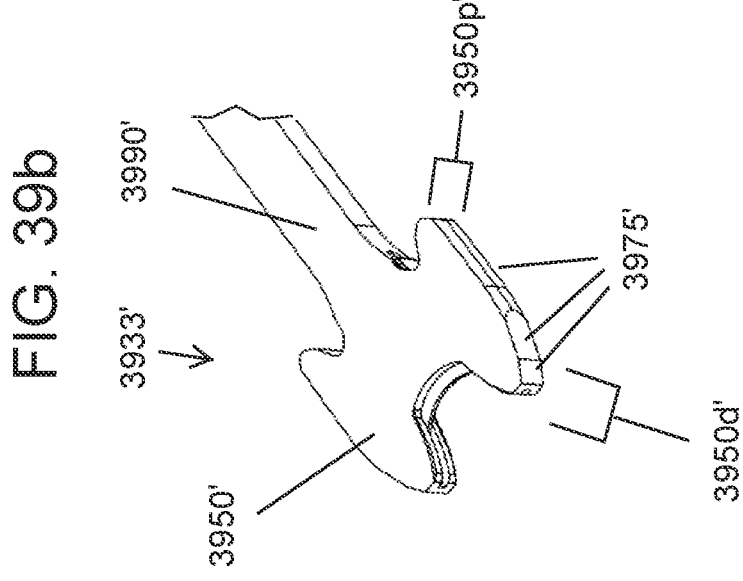
Figure 39A:
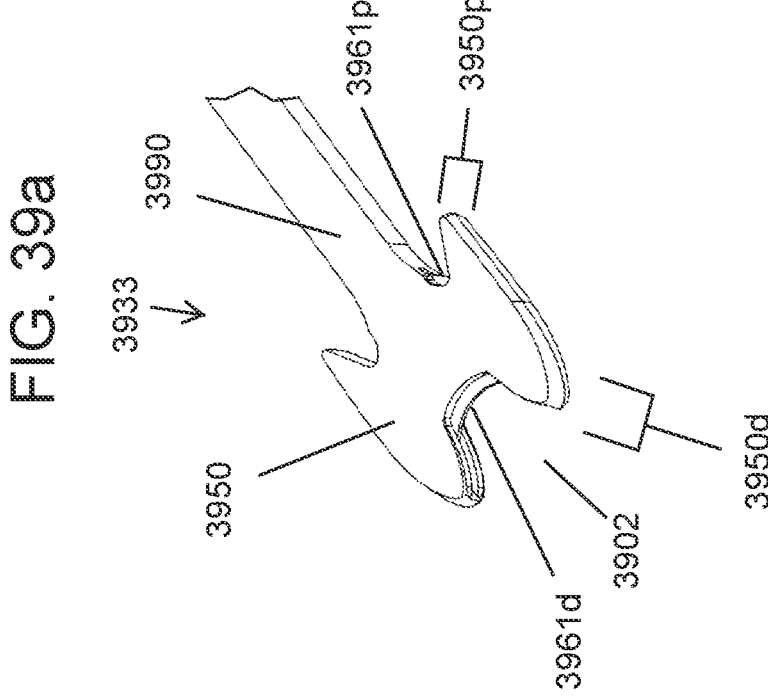

FIG. 39a is a perspective view of a dissector with flattened features.

FIG. 39b is a perspective view of a dissector with flattened features and facets.

DETAILED DESCRIPTION

Further details regarding various embodiments will now be provided with reference to the drawings.

Figures 1J, 1K, 1L, 1M, 1N, 1O, 1P:
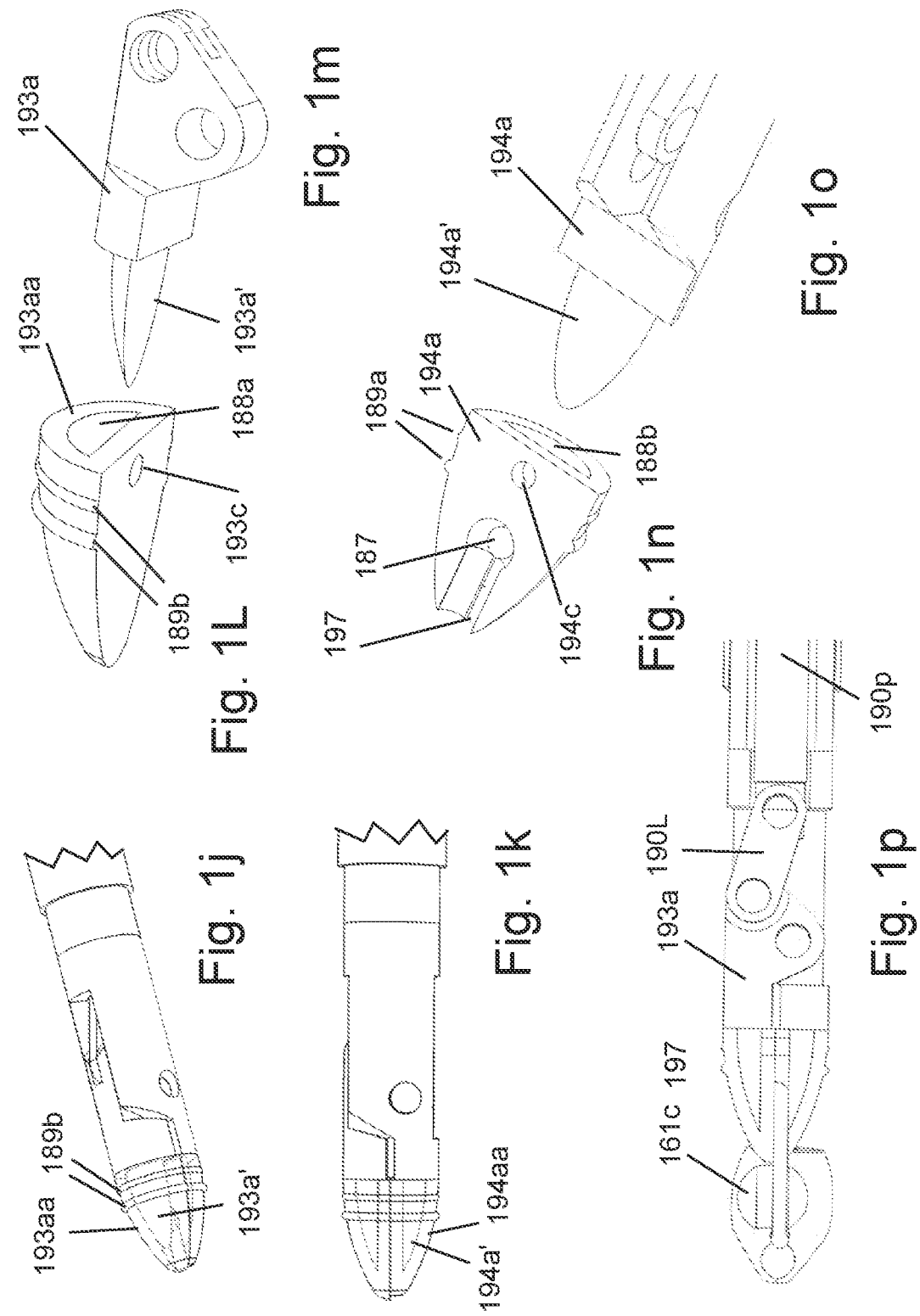
FIG. 1j is a perspective view of the distal tip of the grasping/control instrument with transparent jaw coverings exposing the jaw tongues of the embodiment shown in FIG. 1r.
FIG. 1k is a side view of the distal tip of the grasping/control instrument with transparent jaw coverings exposing the jaw tongues of the grasping/control instrument of the embodiment shown in FIG. 1r.
FIG. 1L is perspective view of an upper jaw covering of the grasping/control instrument of the embodiment shown in FIG. 1r.
FIG. 1m is a perspective view of an upper jaw armature and jaw tongue of the grasping/control instrument of the embodiment shown in FIG. 1r.
FIG. 1n is a perspective view of a lower jaw covering of the grasping/control instrument of the embodiment shown in FIG. 1r.
FIG. 1o is a perspective view of a lower jaw armature and jaw tongue of the grasping/control instrument of the embodiment shown in FIG. 1r.
FIG. 1p is a cross sectional side view of the grasping/control instrument and lysing tip of the embodiment shown in FIG. 1r.

FIGS. 1a-1v depict an embodiment of a CDTD (Cannula Delivered Tissue Dissector) or non-CDTD system 100. System 100 comprises a plurality of protrusions 101 defined by beads 151 and jaw covers 193aa/194aa and recessions 102 positioned in between adjacent beads 151 and jaw covers 193aa/194aa. System 100 comprises a lysing tip 110 that is configured to be completely separable from any other element of the system, however, lysing tip 110 may be configured to work in conjunction with the distal end of jaw assemblies 193/194 of grasping/control instrument 190, as the rigid grasping member 161 may provide a desirable spacing between the lysing tip 110 and the distal ends of the jaw.

Lysing tip 110 may comprise two beads 151a/151b positioned at opposite end of lysing member 160. In alternative embodiments, beads 151a/b may be replaced with beads of any shape, including but not limited to those depicted in FIGS. 7aa to 7zzz. Beads 151 may be comprised of facets 152. In the depicted embodiment, lysing member 160 may be permanently or temporarily coupled to a rigid and/or substantially rigid grasping member 161 as shown in FIGS. 1d, 1e, 1f, 1g, and 1i. In the depicted embodiment, grasping member 161 comprises a grasping wire. However, other embodiments are contemplated in which grasping member may comprise, for example, a flattened grasping member, such as a grasping plate. As also depicted in the figures, grasping member 161 extends at right angle with respect to lysing member 160, although this need not be the case in alternative embodiments. In some embodiments, one or both of jaws 193/194 may comprise a slot 197 configured to receive the rigid grasping member/wire 161. Slot 197 may be configured so as to tightly receive rigid grasping wire 161 so as to prevent or at least inhibit rotation of lysing tip 110.

Alternatively, slot 197 may either be slightly larger than the diameter of rigid grasping wire 161 or may be configured to allow a user to adjust the size of slot 197 by actuating one or both of jaw assemblies 193/194 such that the user can provide for a desired amount of rotation corresponding with the force delivered to jaw assemblies 193/194. In other embodiments, the grasping member/wire 161 may have a non-circular cross-section and the slot 197 may have a similar non-circular cross-section so as to inhibit rotation. Other features may be included to limit or selectively allow for rotation of the lysing tip 110 by inhibiting the rotation of rigid lysing wire 161, such as welds and/or modifications to the terminus of grasping wire 161 such as welded/metallic terminus 161a. For example, in some embodiments, terminus 161a may shaped as a spheroid, ellipsoid, or other geometric shape, which may be enlarged with respect to grasping member/wire 161 (in the depicted embodiment, terminus 161a comprises a conductive-metal hemisphere). In some embodiments, terminus 161a may be configured to be received in a terminal portion of slot 197, such as opening 187, which may keep tip 110 in a fixed position with respect to instrument 190. As described below, in some embodiments, opening 187 may also comprise a conduit to allow for delivery of electrosurgical energy from instrument 190 to lysing member 160 of tip 110. In some such embodiments, terminus 161a may protrude through opening 187 to allow for direct contact with a conductive portion of instrument 190, such as tongue 194a'.

In other contemplated embodiments, spacers may be positioned adjacent to opposing outer beads 151a/b such that the rigid grasping wire 161 may intersect the lysing member/rod between two spacers (not shown) and such that spacers are positioned between each two adjacent beads, as described below in connection with an alternative embodiment in FIG. 2. Such spacers may be used to either inhibit or selectively limit rotation by, for example, their shape, and/or proximity to the intersection point. In alternative embodiments, spacers may be replaced with spacers of any shape, including but not limited to those depicted in FIGS. 7h-7t. This alternative embodiment may be applied to other embodiments herein.

In this embodiment, beads 151a/b may rotate about lysing rod 160, thus, a surgeon may be able to dissect on one or more of the sides of the dissection plane on the backstroke, possibly making surgery more efficient via dissecting in the reverse direction. In some embodiments, beads 151a/b may be configured to rotate about lysing rod 160 such that the distal ends of the beads become the proximal ends when the motion of the lysing tip is reversed. However, in other embodiments, the rotation may be limited to another predetermined range of motion.

It can also be seen in, for example, FIG. 1g, that lysing rod 160 defines both distal-facing and proximal-facing lysing segments. In other words, on the distal end of lysing tip 110, a distal-facing lysing segment is defined by lysing rod 160 in between beads 151a and 151b and on the opposite side a pair of lysing segments are defined on either side of wire 161 in between wire 161 and/or insulating object 161c and the adjacent bead. Thus, both the beads 151a/151b and the lysing members/elements of lysing tip 110 are specifically configured to provide for dissection in both distal and proximal directions during use.

It should also be understood that beads 151a and 151b are preferably, at least along their respective surfaces, non-conductive, or at least substantially non-conductive. As such, the beads 151a and 151b can serve a protective function to prepare the adjacent tissue for sequestered dissection and/or electrodessication by the adjacent lysing segments. Otherwise stated, by providing an adjacent protruding, non-conductive surface, the lysing segments may be sequestered from the tissue to be treated, while the bead surfaces, preferably protruding distally and proximally, may be used to stretch, spread, guide, and/or position the target tissue without directly delivering electrosurgical energy from the beads to the dissected tissues. Delivering electrosurgical energy from the beads themselves may cause unwanted tissue damage and inhibit this functionality.

In the depicted embodiment, a moveable sheath 195 external to the grasping control device 190 may reduce electrosurgical discharge by preventing upper and lower conductive jaw armature 193a/194a from being exposed to bodily fluids, charred material, and debris. The moveable sheath 195 is usually present along a substantial length of the shaft 190a of the grasping control instrument 190. Sheath 195 may be comprised of plastic, silicone, ceramic, cermet, halogenated hydrocarbon, and/or other nonconductive materials. Sheath 195 may be disposable facilitating cleaning of the instrument and replacement of sheath. Prior to use, sheath 195 may be slid into a position to expose the metal armature of the jaw assemblies to facilitate cleaning. During delivery and use, sheath 195 may be slid distally until the distal end of sheath 195 contacts the most distal rib of ribs 189b of jaw coverings 193aa/194aa. Upper and lower jaw coverings 193aa and 194aa may be nonconductive and specially shaped with one or more ribs 189a/189b ridges, and/or surface features so as to prevent outer sheath 195 overlying shaft 190a from sliding to an unwanted position. Sheath and ribs as well, when suitably positioned, may form a seal to prevent unwanted electrical discharge. In some embodiments, ribs 189a/189b may also provide the surgeon with a physical end point to the extension of sheath 195.

While the grasping/control instrument 190 is energized with electrosurgical energy, beads 151a/151b and upper and lower jaw coverings 193aa and 194aa are preferably nonconductive, thus minimizing unwanted electrical discharge. Each upper and lower jaw assembly 193/194 respectively, may be comprised of upper and lower jaws 193a/194a (that may be conductive and/or metallic) and upper and lower jaw coverings 193aa/194aa, respectively. Upper and lower jaws 193a/194a may comprise corresponding distal jaw tongues 193a'/194a'. The inside of one or both non-conductive jaw coverings 193aa and 194aa may be formed with one or more receiving chambers 188a and 188b respectively, to receive their corresponding conductive tongues 193a' or 194a'. The electrically conductive tongues 193a' and/or 194a' may have an area adjacent to opening 187 in one or more of the nonconductive jaw coverings 193aa/194aa in order to permit electrosurgical energy flow to from one or more electroconductive tongues to the terminus 161a of rigid grasping wire 161. In some embodiments, a portion of tongues 194a' and/or 193a' may be configured to protrude into opening 187 to further facilitate such energy transfer, possibly instead of protruding terminus 161a. However, in the depicted embodiment, tongues 194a' and/or 193a' may be relatively flat in this region. Nonconductive jaw coverings 193aa/194aa may be comprised of ceramic, cermet, glass, various halogenated hydrocarbons, and any other suitable nonconductors. Nonconductive jaw coverings 193aa/194aa may be restricted in their motion and/or affixed to conductive tongues 193a'/194a' via one or more cover welds placed in cover weld holes 193c/194c, said welds may be affixed to each tongue thus restricting movement of the corresponding jaw covering. When an electrosurgical generator is activated by a surgeon, electrosurgical energy may be transmitted through the metal pushrod 190p, through linkage 190L, and through upper and/or lower jaws 193a/194a coupled to jaw tongues 193a'/194a'. The pivot points along the electrical path may be coupled in ways commonly known in the art, for example, via pins.

Jaw assemblies 193/194 may be comprised of single action or double action jaws that may, but need not, open more than 10 to 15 degrees relative to one another in order to accept/capture the terminus 161a of rigid grasping wire 161. This reduced range of motion may reduce damage to ceramic coverings 193aa/194aa.

Lysing tip 110 may be configured to prevent or limit lateral movement of outer beads 151a/b by joining metallic spheroid 160a via weld 160w to lysing rod 160 within bead rod tunnels 154 and corresponding bead holes 155 intersect. In some embodiments, other objects may be welded or glued to effectively couple the beads 151a/151b to lysing rod 160. In the depicted embodiment, metallic bulbs 160a, such as ball bearings or other spheroids, may be passed down hole 155 and welded to the ends of lysing rod 160 at bead weld 160w. This may allow for rotational movement of beads around the lysing rod 160. Any suitable welding technique may be used, however, resistance welding may be preferred. In the depicted embodiment, beads 151 are about 4 mm in length, tunnel 154 is about 0.55 mm in diameter containing lysing rod 160 about 0.5 mm in diameter, and/or bead hole 155 is about 0.8 mm in diameter which can capacitate the transport and welding of an about 0.7 mm metallic spheroids 160a. The diameter of metallic spheroids 160a is preferably smaller than hole 155, but larger than tunnel 154 so bulbs/spheroids 160a can be inserted through tunnel 154 and, once welded, metallic spheroids 160a prevent the lysing rod 161 from being withdrawn through/from tunnel 154. In some embodiments, other geometric shapes may be used that prevent the lysing rod 161 from being withdrawn through/from tunnel 154. The spheroidal shape of a ball bearing or substantially spheroidal shape of a polyhedron may still allow for rotation of beads 151a/b provided the tunnel sizes and weld sizes permit. Alternatively, other shapes and/or sizes of bulbs may be used to inhibits, or limit, rotation of corresponding beads as desired.

In alternative embodiments, the dimensions of lysing rod 160 may be modified to approach the width and/or thickness of previously described lysing plates, as described in U.S. patent application Ser. No. 15/464,199 titled "Apparatus, Systems, and Methods for Minimally Invasive Dissection of Tissues", which is hereby incorporated herein by reference in its entirety. Additionally, in alternative embodiments, the rigid grasping wire 161 may be modified in width and in thickness to resemble a plate. The terminus 161a may also be modified so as to require a corresponding recession in the upper jaw in order to allow proper occlusion of the jaws.

In some embodiments, the exposed regions of rigid grasping wire 161 may be overlaid with an insulating coating, such as a ceramic, cermet, glass, halogenated hydrocarbon, diamond-like carbon coating, plastic, epoxy, or the like. In the depicted embodiment, however, rather than a coating, one or more exposed regions of rigid grasping wire 161 may be covered with a non-conductive object 161c that may be comprised of ceramics, cermets, and glass, and may be shaped as spheroids, cylinders, and/or capsule shapes. Such a dielectric object 161c on the exposed area of the rigid grasping wire 161 may, among others, facilitate smooth tissue movement of the lysing tip and reduce tissue trauma while reducing unwanted electrical discharge. Non-conductive objects, such as object 161c, may be preferred over mere coatings due to enhanced ability to inhibit undesired transfer of electrosurgical energy and may be applied by sliding such objects in place over the grasping wire 161.

While traditional non-conductive coatings of metallic parts may be applied to the distal grasper's jaws and armature, such coatings may not be as effective at preventing electrical discharge after a certain number of uses and/or cleaning cycles. Using ceramics and/or more robust non-conductive materials to make the jaw coverings may allow for a greater number of cleaning cycles thus providing more cost value to surgeons and/or patients.

Beads 151, or any of the other beads described herein, are preferably made from a suitable inert, biocompatible, and non-conductive material, for example, such as a suitable plastic, alumina, zirconia, silicon nitride, silicon carbide, glass, graphite, silicate, diamond, carbon-containing compounds, cermet, or ceramic material or the like, or a combination of one or more of the foregoing.

In the depicted embodiment, lysing rod/member 160 is positioned through beads 151 at a location such that beads 151 may be non-symmetrical and/or eccentric relative to tunnels 154. In other words, as best shown in FIG. 1*c*, tunnels 154 more be positioned to extend through a non-central location within beads 151. Moreover, in the depicted embodiment, beads 151 are non-symmetrical relative to an axis extending through the side-to-side centers of beads 151 (perpendicular to the long axis of the beads). In addition, as shown in the figures, the distal/forward tip of beads 151 may have a more narrowed end to act more as a wedge for purposes of acting as a blunt dissector between tissues and tissue planes; the proximal/non-distal/back portions being less narrowed and/or larger in volume may create a desirable drag effect thus orienting the bead in a desirable direction for dissection. Whereas the rear/proximal end of beads 151 may take many shapes that may be larger and/or more prominent than that of the front/distal end of the beads. As in FIG. 1*a*, the forward tip may be narrowed by use of facets 152; three are visible and numbered and the fourth is on the opposite side of the one facing the reader. As described later in FIGS. 7*aa-zzz*, a wide variety of alternative bead shapes are possible including, for example, ovoid shapes, spherical shapes, wheel shapes, bullet shapes or other shapes having a flat terminal end (such as, for example, frusto-shaped), wing shapes, etc. As can be seen from some of the examples shown in FIGS. 7*aa-zzz*, in some embodiments, beads may be symmetrical relative to the openings for receiving the rod. In some embodiments, beads 151 may be faceted on the top, bottom, sides, front and/or back. Facets are preferably formed on the distal/front/leading portions of the bead to facilitate tip movement through/between tissue layers.

In some embodiments, the tunnels 154 may be positioned in a non-central location within beads 151. For example, in some preferred embodiments, the tunnels 154 may be positioned in a forward or distal location relative to a central axis of beads 151. This may be preferable to allow the lysing tip 110 to be directed through tissue in a desired manner, such as without allowing the beads 151 to rotate on their respective tunnels in an undue manner. However, some embodiments may be configured to allow a certain amount of such rotation so that the tip can be maneuvered through patient tissue in a flexible manner.

In some alternative embodiments, the forward or distal portions 101 of beads relative to tunnels 154 may also, or alternatively, be wider than such that beads 151 have a trailing end that may be longer and/or more narrow, which may yield desired aerodynamics and/or maneuverability; this may be similar to a 'kite-tail' effect.

Preferably, the entire surface of the beads may be smooth, however, some faceting features may provide for a surface that is less smooth. For example, providing a smooth front end and a smooth trailing end may allow the lysing tip to be moved in a forward direction and then in a rearward direction back and forth without catching an undesirable amount of tissue on beads to inhibit such movement. However, as mentioned elsewhere in this disclosure, in some embodiments, the trailing end may comprise a flat surface such that the entire bead comprises a frusto-ellipsoidal shape or another similar shape. Preferably, at least the forward or distal surface of the beads is smooth and defines an ellipsoidal shape or another shape having an at least substantially smooth forward surface. In alternative embodiments, various portions of the bead may be textured or given surface irregularities that may yield a desired dissection orientation such as for example having the non-proximal/rear portion of the bead roughened on the surface to create drag from the rear.

In some embodiments, it may be desirable to allow beads 151 to rotate on lysing rod 160. Thus, beads 151 may not be fixed three-dimensionally with respect to lysing rod 160 and/or one or more other elements of lysing tip 110. In some such embodiments, beads 151 may be at least partially rotatable with respect to the entire lysing tip 110. For example, the beads may rotate about the rod upon encountering tissue similar to that of a vegetable/fruit peeler. In embodiments in which beads 151 are rotatable in this manner, it may be desirable to use a lysing rod having a circular cross section. Other embodiments are contemplated in which, instead of being rotatable, the beads may be otherwise movable with respect to one or more elements of a lysing tip 110. In any such embodiments, such beads may be considered not three-dimensionally fixed with respect to the lysing rod and/or lysing tip.

Each bead may comprise hole 155 that may be positioned perpendicular to lysing rod hole 154; holes 155 may be available as a platform/location to add other features/components such as providing a location for coupling of a cord as described below in connection with other embodiments and/or locating a sensor and/or RFID location component and/or being used for placement of luminescent and/or light production element(s) for visualization, for example, tritium and the like.

The shape of lysing member/lysing rod 160 may also be important as to the most efficient and safe means to transfer electrosurgical energy from the lysing rod to the tissue(s). Since electrosurgical energy on/under a surface tends to move toward edges of an object, a lysing rod with a circular cross section may force current to the opposing lysing rod tips and/or protuberances creating hot spots at/near adjacent beads and/or protuberances. Therefore, it may be beneficial for lysing rod 160 to comprise a non-circular cross section with substantially uniform edges along its length from which electrosurgical energy may uniformly be transferred to tissues. In contemplated embodiments, a pentagonal or hexagonal cross-sectional shape may be preferable. In other embodiments, spacers with non-circular cross-sections may accumulate less debris and/or eschar on lysing rod and/or spacer because debris may have a more difficult time adhering to an angled edge when forces are applied to the debris.

In alternative embodiments, system 100 may be delivered into the body via a cannula and/or trocar as shown in FIGS. 8*a*-8*d*.

Grasping/control instrument 190 may comprise means for grasping and/or controlling lysing tip 110. "Controlling" herein may be described as including, but not limited to, the physical movement of lysing tip in any direction and/or orientation and the conduction of electrosurgical energy to lysing tip.

The deployment assembly of system 100 may further comprise a handle assembly 60 that may be used to selectively deploy via shaft 191 lysing tip 110 and control various aspects of its delivery and/or use during surgery. Handle assembly 60 comprises a body 61 coupled with a pistol grip 62. Shaft 191 may extend from and be coupled with handle assembly 60. A rocker assembly 65 or another such control means may be provided for actuation of various features/functions/elements in system 100. For example, rocker assembly 65 may be coupled with cords (not shown) such that, upon pressing rocker assembly 165 along a top portion of the assembly, one or more of jaw assemblies 193/194 may open or close.

An electrosurgical actuation button 167a may be provided, which a surgeon may use to initiate transmission of electrosurgical energy to lysing tip 110. More particularly, electrosurgical actuation button 167a may be used to initiate transmission of electrosurgical cutting or blended energy to lysing tip 110. Additionally, a second electrosurgical actuation button 167b may be positioned to enable delivery of another type of energy to lysing tip 110. Buttons 167a/b may be positioned on rocker assembly 65 if desired or at the location of button 167b, as shown in FIG. it. Pressing or otherwise actuation of buttons 167a/b may result in delivery of such energy from an electrosurgical generator coupled with handle assembly 60. Handle assembly 60 may also be used in connection with any of the other embodiments disclosed herein.

It should be understood that handle assembly 60 may be used in connection with one or more of the other systems disclosed herein. Of course, those of ordinary skill in the art will appreciate that any other handle assembly, gun, or other available control mechanism may also be used, as desired.

Handle assembly 60 may be more conducive to procedures in which the lysing tip is intended for use within a lumen of the body and/or through cannulas/trocars that act as corridors from outside the body to inside the body. In alternative embodiments, hand assembly 60' depicted in FIGS. 1u-v, may provide the surgeon with a more optimal and/or comfortable means to manipulate lysing tip 110 via shaft 191'. In this embodiment, as more precisely shown in cross-sectional FIG. 1v, pushrod 190p within shaft 191' may reversibly or permanently couple with coupling linkage 64. In alternative embodiments, coupling means 63 may be used to facilitate the coupling between pushrod 190p and coupling linkage 64. As the user moves toggle 65' back and forth, coupling linkage 64 is likewise moved and transfers its directional movement to pushrod 190p that opens and/or closes one or both jaw assemblies 193/194. Delivery of one or more energy types of energy may be actuated via buttons 167a' and 167b' in order to cause electrosurgical generator to deliver a particular type of electrosurgical energy to lysing tip 110 via handle assembly 60' and shaft 191.

FIGS. 2a-2m depict an embodiment of a CDTD or non-CDTD system 200. System 200 comprises a plurality of protrusions 201 defined by beads 251 and jaw covers 293aa/294aa and recessions 202 positioned in between adjacent beads 251 and jaw covers 293aa/294aa. System 200 comprises a lysing tip 210 that is configured to be completely separable from any other element of the system, however, lysing tip 210 may be configured to work in conjunction with the substantially ellipsoidal distal end of jaw assemblies 293/294 of grasping/control instrument 290 to serve as a "pseudo-bead" during an electrosurgical procedure. Grasping/control instrument may comprise grasping channel 297 (which may further comprise an electrosurgical energy transfer opening 287. Channel 297 may be configured to receive and/or hold lysing rod 260.

Lysing tip 210 may comprise two beads 251a/251b positioned at opposite end of lysing member 260. Lysing member 260 may be divided into lysing segments 261a (covered by spacer 262) and 261b. In other embodiments, other features may be included to limit or selectively allow for rotation such as welds and/or spacers (for example, spacer 262 extending from the inside of the bottom bead, as shown in FIG. 2f to the jaw assemblies 293/294). In some embodiments, spacers may be positioned adjacent to opposing outer beads such that jaws may grip lysing rod in between the two spacers. Such spacers may be used to either inhibit or selectively limit rotation by, for example, their shape, and/or proximity to jaw assemblies 293/294. This alternative embodiment may be applied to other embodiments herein. In alternative embodiments, spacers 262 may be replaced with spacers of any shape, including but not limited to those depicted in FIGS. 7h to 7t. In the depicted embodiment, beads 251a/b may rotate about lysing rod 260, thus, a surgeon may be able to dissect on one or more of the sides of the dissection plane on the backstroke, possibly making surgery more efficient via dissecting in the reverse direction. Beads 251a/b may be configured to rotate about lysing rod 260 such that the distal ends of the beads become the proximal ends when the motion of the lysing tip is reversed.

In the depicted embodiment, a moveable sheath 295 external to the grasping control device 290 may reduce electrosurgical discharge by preventing upper and lower conductive jaw armature 293a/294a from being exposed to bodily fluids, charred material, and debris. The moveable sheath 295 is usually present along a substantial length of the shaft 291 of the grasping control instrument 290. Sheath 295 may be comprised of plastic, silicone, ceramic, cermet, halogenated hydrocarbon, and/or other nonconductive materials. Sheath 295 may be disposable, thereby facilitating cleaning of the instrument and replacement of sheath. Prior to use, sheath 295 may be slid into a position to expose the metal armature of the jaw assemblies to facilitate cleaning. During delivery and use, sheath 295 may be slid distally until the distal end of sheath 295 contacts the most distal rib of ribs 289a of jaw coverings 293aa/294aa. Upper and lower jaw coverings 293aa and 294aa may be nonconductive and specially shaped with ribs 289a/289b and/or ridges and/or surface features so as to prevent outer sheath 295 overlying shaft 291 from sliding to an unwanted position. Sheath 295 and ribs 289a may also, when suitably positioned, form a seal to prevent unwanted electrical discharge. In some embodiments, ribs 289a/289b may also provide the surgeon with a physical end point to the extension of sheath 295.

While the grasping/control instrument 290 is energized with electrosurgical energy, beads 251a/251b and upper and lower jaw coverings 293aa and 294aa are preferably nonconductive, thus minimizing unwanted electrical discharge. Each upper and lower jaw assembly 293/294 respectively, may therefore be comprised of upper and lower jaws 293a/294a (that may be conductive and/or metallic) and nonconductive upper and lower jaw coverings 293aa/294aa, respectively. Upper and lower jaws 293a/294a may comprise corresponding distal jaw tongues 293a'/294a'. The inside of one or both non-conductive jaw coverings 293aa and 294aa may be formed with one or more receiving chambers 288a (lower jaw covering depicted, upper jaw covering not depicted) respectively, to receive their corresponding conductive tongues 293a' or 294a'. The electrically conductive tongues 293a' and/or 294a' may be configured to deliver electrosurgical energy through electrosurgical energy transfer opening 287 in one or more of the nonconductive jaw coverings 293aa/294aa in order to permit electrosurgical energy flow to lysing rod 260.

Figures 2H, 2I, 2J, 2K, 2L, 2M:
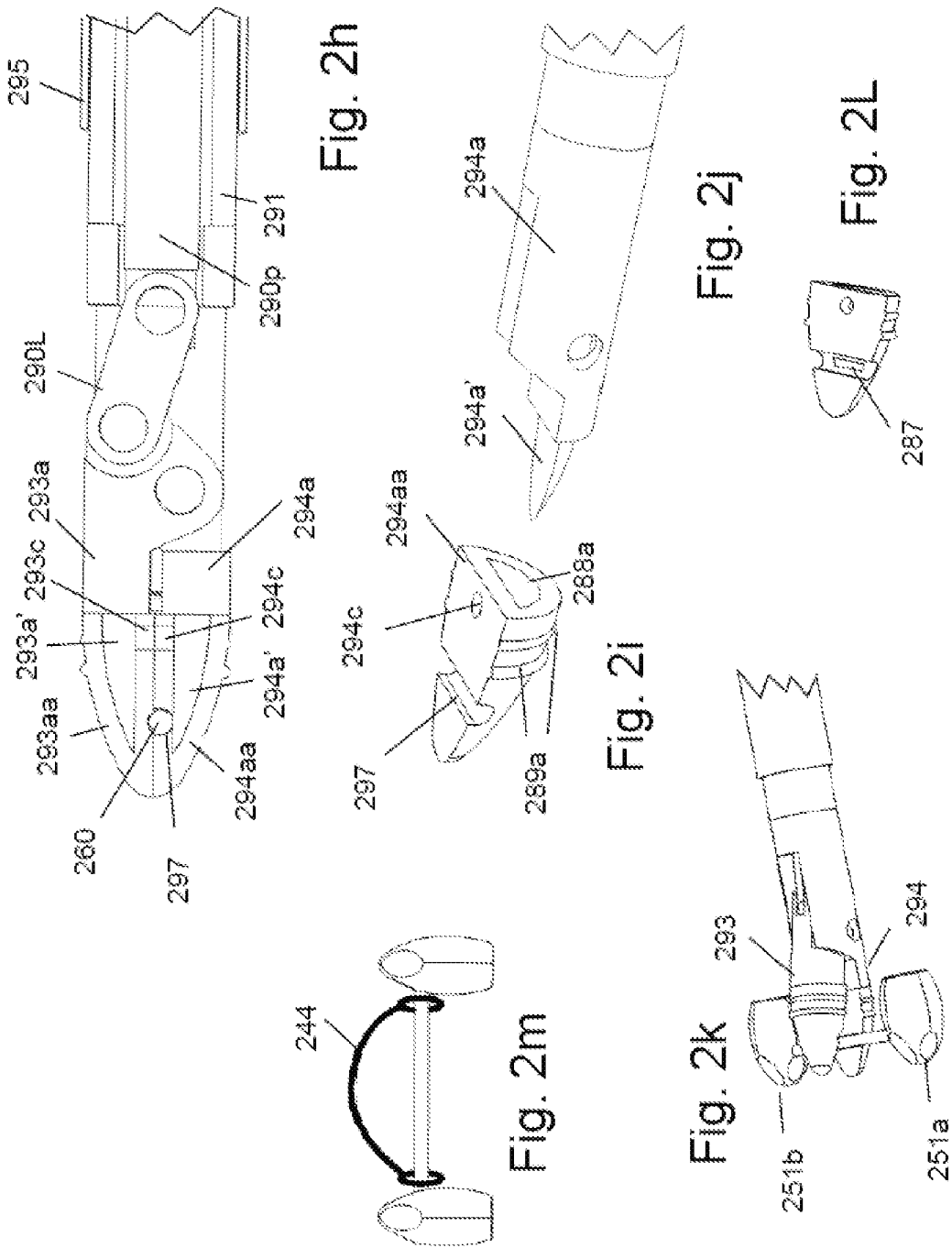

In this embodiment, opening 287 and slot 297 may be formed so as allow a portion of tongue 294a' to protrude into slot 297 to allow for direct contact between lysing rod 260 and tongue 294a', as best shown by the cross section in FIG. 2h. Nonconductive jaw coverings 293aa/294aa may be comprised of ceramic, cermet, glass, various halogenated hydrocarbons, and any other suitable nonconductors. Nonconductive jaw coverings 293aa/294aa may be restricted in their motion and/or affixed to conductive tongues 293a'/294a' via one or more cover welds placed in cover weld holes 293c/294c, said welds may be affixed to each tongue thus restricting movement of the corresponding jaw covering. When an electrosurgical generator is activated by a surgeon, electrosurgical energy may be transmitted through the metal pushrod 290p, through linkage 290L, and through upper and/or lower jaws 293a/294a coupled to jaw tongues 293a'/294a'. The pivot points along the electrical path may be coupled in ways commonly known in the art and as previously mentioned, for example, via pins.

Jaw assemblies 293/294 may be comprised of single action or double action jaws that may, but need not, open more than 10 to 15 degrees relative to one another.

In some embodiments, lysing tip 210 may be configured to prevent or limit lateral movement of outer beads 251a/b by, as previously described, joining spheroids 260a or other bulbs via weld to lysing rod 260 within rod tunnels (tunnels 154a/154b shown in FIG. 1b) and corresponding bead holes (holes 155a/155b intersect tunnels shown in FIG. 1c). In some embodiments, other objects may be welded or glued to effectively couple the beads 251a/251b to lysing rod 260. In the depicted embodiment, metallic spheroids 260a such as ball bearings may be passed down bead hole and welded to the ends of lysing rod 260. This may allow for rotational movement of beads around the lysing rod 260. Any suitable welding technique may be used, however, resistance welding may be preferred. In the depicted embodiment, beads 255a/b are about 4 mm in length, bead tunnel is about 0.55 mm in diameter containing lysing rod 260 about 0.5 mm in diameter, and/or bead hole is about 0.8 mm in diameter which can capacitate the transport and welding of an about 0.7 mm metallic spheroids 260a. The diameter of metallic spheroids 260a is preferably larger than bead tunnel so once welded, now-welded metallic spheroids 260a prevent the lysing rod 260 from being withdrawn through/from tunnel. In some embodiments, other geometric shapes may be used that prevent the lysing rod 260 from being withdrawn through/from tunnel. The spheroidal shape of a ball bearing or substantially spheroidal shape of a polyhedron may still allow for rotation of beads 251a/b provided the tunnel sizes and weld sizes permit.

In alternative embodiments, the dimensions of lysing rod 260 may be modified to approach the width and/or thickness of lysing plates as shown in FIGS. 4a-4j.

While traditional non-conductive coatings of metallic parts may be applied to the distal grasper's jaws and armature, such coatings may not be as effective at preventing electrical discharge after a certain number of uses and/or cleaning cycles. Using ceramics and/or more robust nonconductive materials to make the jaw coverings may allow for a greater number of cleaning cycles thus providing more cost value to surgeons and/or patients.

In alternative embodiments such as that depicted in FIG. 2m, the lysing rod 260 and/or lysing tip 210 may be manipulated within a trocar and/or cannula and/or internal body cavity via loop 244 which may comprise a biodegradable substance which may also comprise absorbable suture, gelatin, wax, etc. In contemplated embodiments, a loop may comprise absorbable suture material, including but not limited to polyglycaprone, polyglycolic acid, polylactic acid, and polydioxanone. An opposing grasping instrument may temporarily grasp loop 244 to hold lysing tip 210 in place while the jaws of the treatment/grasping instrument 290 lock down on the desired portion of the lysing rod 260 and/or lysing tip 210. Once the device is electrosurgically activated and discharges energy and significant temperatures are generated, the biodegradable loop 244 may be configured to melt or decompose thus exposing the desire portions of lysing rod 210 so treatment may commence. Various shapes of loop 244 may be used varying from the simplest of tied suture knots to the bubble-blower shaped shown in FIG. 2m to a simple rectangle with a hole that allows string passage like a luggage ticket string. Alternatively, loop 244 may be glued on to lysing rod 260 with a biocompatible glue that may decompose at the high temperatures of electrosurgery which may vary from 100° C. to the extremes of electrical discharge within the body. In additional embodiments, a tab may be coupled with the lysing tip to/from facilitate transfer to a grasping control instrument in a similar manner such as the tab 860t shown in FIGS. 8a & 8b.

In other embodiments, system 200 may be modified to include a tether permanently or reversibly attached to lysing rod 260 that is threaded through an opening in one or both of jaw assemblies 293 and/or 294. For example, prior to a procedure, a biocompatible thread may be tied via knot to lysing rod 260 and threaded through an opening in one jaw. The threaded lysing tip 210 may be passed through an incision into the body or through a cannula/trocar, perhaps aided by the jaws of grasping control instrument 290. Once the tip of grasping/control instrument 290 is in a location with space sufficient for coupling, the tether may be pulled tight either manually or by way of a mechanism, thus directing lysing rod 260 into slot 297.

FIGS. 3a-3i depict another embodiment of a CDTD or non-CDTD system 300. System 300 comprises a lysing tip 310 comprising protrusions 301 and recessions 302 defined by the regions between adjacent beads 351a/b/c/d and, more particularly, a lysing member comprising a lysing plate 360 extending along tip 310. System 300 comprises a lysing tip 310 that may be configured to be completely separable from any other element of the system. However, in some embodiments, lysing tip 310 may be configured to work in conjunction with the substantially ellipsoidal-shape at the distal end of jaw assemblies 393/394 of grasping/control instrument 390, as this preferably insulated shape may serve the same functions as beads 351ab/c/d as previously discussed. Thus, the shape of the distal end of grasping/control instrument 390 may mimic the shape of the distal ends of each of the various beads 351 Lysing tip 310 comprises four beads 351a/b/c/d. One of these beads 351d is positioned at a first end of lysing tip 310 and beads 351a-c extend along lysing member 360 in a row adjacent to bead 351d. Rather than having a bead positioned opposite from bead 351d, a bulbous terminus 361 is provided at the opposite end. Bulbous terminus 361 may comprise, for example, a spherical or semi-spherical (frusto-spherical, for example) shape that, as discussed below, may be used to allow for a suitable instrument, such as grasping/control instrument 390, to hold and/or manipulate lysing tip 310 during a surgical procedure. Although it may be preferred to position bulbous terminus 361 at a terminal end of lysing tip 310, other embodiments are contemplated in which a bulb or other structure used for grasping and/or controlling may be positioned at another location along lysing member 360 and/or tip 310.

In system 300, lysing plate 360 may be inserted through and/or into the beads 351 via widened tunnels 354 and maintained in place by a welds or glues or other fasteners placed in holes 355 in the rear of the frusto-shaped beads. In other embodiments, holes 355 to facilitate welding or otherwise coupling of beads 351*a/b/c/d* (collectively 351) to lysing plate 360 may exit beads 351*a/b/c/d* in any number of locations. The dimensions of the lysing plate may be approximately 0.3 mm in thickness and approximately 2 mm in width by approximately 7 mm in length. However, in further contemplated embodiments, these dimensions may be ⅓ to 10× in number. System 300 may be configured to prevent or limit lateral movement of beads 351 by fixing bead holes 355 in the beads and to corresponding lysing plate weld zones. Alternatively, a substantially solid object like a pin or glue may be inserted to effectively couple the beads 351 to the lysing plate 360 if corresponding holes are made in lysing plate 360. In alternative embodiments, holes in lysing plate 360 may be replaced with grooves that may receive the solid object(s) inserted through fixing bead holes 355.

In the depicted embodiment, lysing member 360 comprises plate 360 which may comprise proximal lysing plate 360*p* and a grasping terminus comprising a bulbous terminus 361. In the depicted embodiment, the grasping terminus is a metallic spheroid 361, which may be configured to match the shape of a corresponding feature of one or both jaws of instrument 390. Although this shape may allow for some rotation/pivoting of tip 310 while within instrument 390, as described in greater detail below, other shapes are contemplated in which this shape may vary. Thus, the grasping and/or bulbous terminus 361 may comprise a geometrically shaped terminus 361 such as spheroid, polyhedron, etc. Upon being grasped by grasping/control instrument 390 to perform a surgical procedure, in some embodiments, the distal end of jaw assemblies 393/394 of grasping/control instrument 390 may substantially mimic the shape and/or function of beads 351*a/b/c/d* such that lysing segments are defined between each bead 351*a/b/c/d* and between the jaw assemblies 393/394 and bead 351*a*. In some embodiments, the portion of jaw assemblies 393/394 extending onto or beyond lysing plate 360 may have an identical or at least similar distal shape and size to beads 351. For example, this distal portion of jaw assemblies 393/394 may have rounded/smooth surfaces that taper towards a rounded tip similar to beads. At the very least, it is preferred that distal tip jaw assemblies 393/394 be shaped and sized such that the adjacent portion of lysing plate 360 can come in contact with or near contact with target tissues. Together, beads 351 and distal portion of jaw assemblies 393/394 may function as blunt dissectors to separate tissues without cutting. While the device is energized with electrosurgical energy, beads 351 and the outer surfaces of jaw assemblies 393/394 are preferably non-conductive in order to perform the blunt dissection function. The inside of one or both jaw assemblies 393/394 and/or its corresponding lower jaw define a receiving slot 397. In some embodiments, receiving slot 397 may be formed in a cover, as previously mentioned, that may fit over one or both jaws of instrument 390. Alternative embodiments are contemplated, however, in which receiving slot 397 may be formed directly in one or both of the jaws themselves.

In the depicted embodiment, receiving slot 397 may comprise a treatment locking portion 397*a*, which may comprise a flattened groove, which may be configured to match the shape of lysing member 360 at one end near terminus 361. Receiving slot 397 may further, or alternatively solely, comprise a rotational portion 397*b*, which may comprise a rounded opening, which may be configured to rotationally engage bulbous terminus 361 and allow for rotation between delivery and treatment configurations. In some embodiments, a similarly rotational slot may be formed in the opposing jaw. In the depicted embodiment, receiving slot 397 may also serve as an opening for delivery of electrosurgical energy from instrument 390 through a jaw cover and into lysing member 360. Thus, rotational portion 397*b* may coincide with an opening 387 in lower jaw covering 394*aa*. Upon placement of the grasping/bulbous terminus 361 into the opening-to-electroconductivity 387 of the receiving slot 397, if electrosurgical energy is applied to the grasping/control device 390, electrosurgical energy may pass through the lysing plate 360 into target tissues when in proper proximity. Preferably, bulbous terminus 361, opening 387, and jaw 394 are configured so as to facilitate direct contact between a conductive jaw or jaw portion and bulbous terminus 361.

Figures 3A, 3B, 3C, 3D, 3E, 3F, 3G, 3H, 3I:
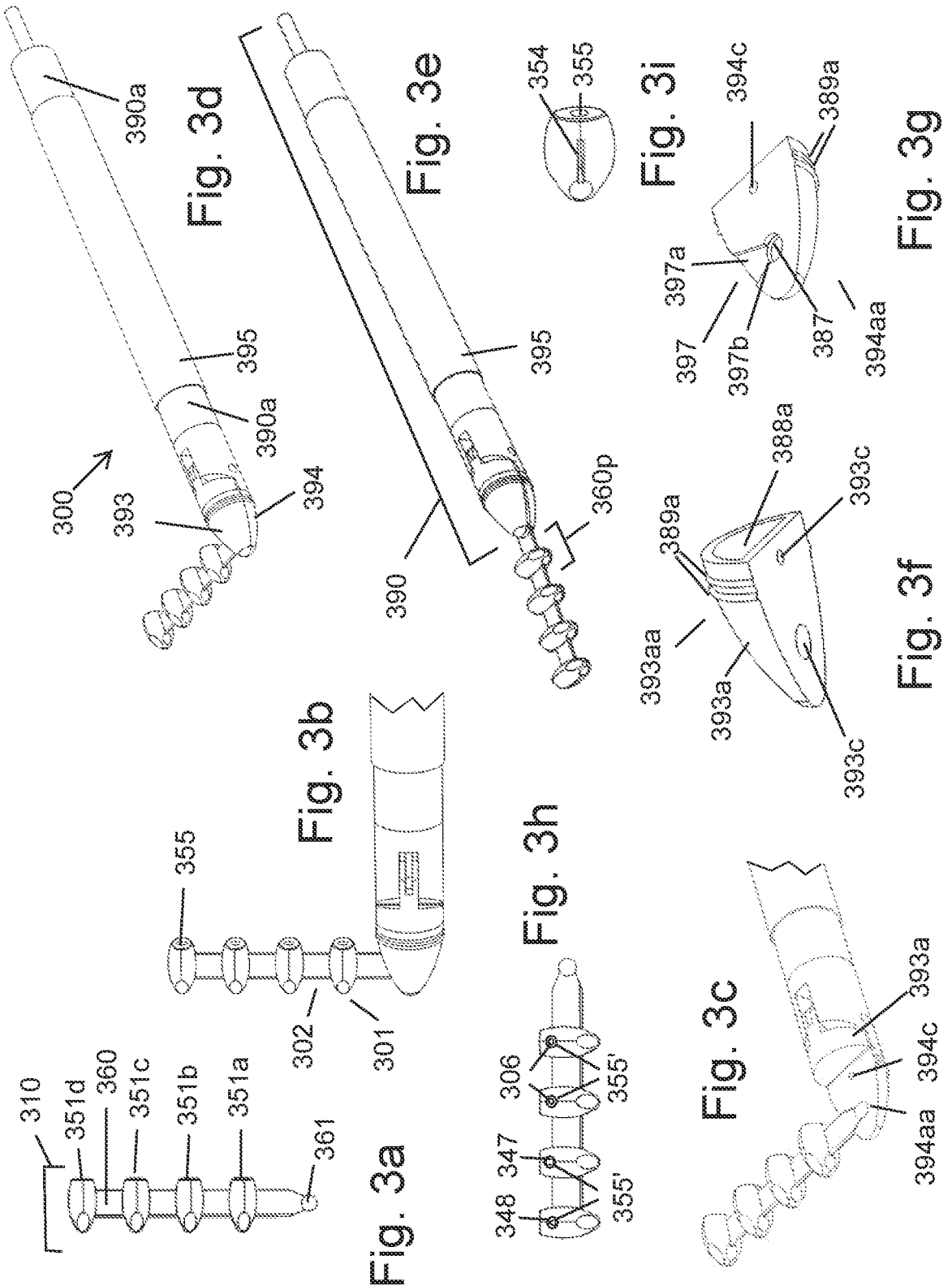
FIG. 3a is an upper view of lysing tip of the embodiment of FIG. 3d.
FIG. 3b is an upper perspective view of the distal tip of the embodiment depicted in FIG. 3d in the treatment configuration.
FIG. 3c is a perspective view of the embodiment previously depicted in FIG. 3a in the delivery configuration.
FIG. 3d is a perspective view of an embodiment of a system for delivery of a lysing tip in a treatment configuration.
FIG. 3e is a perspective view of the embodiment depicted in FIG. 3d in the delivery configuration.
FIG. 3f is a perspective view of the upper jaw covering of the embodiment depicted in FIG. 3d.
FIG. 3g is a perspective view of the lower jaw covering of the embodiment depicted in FIG. 3d
FIG. 3h is an upper view of additional features that may be added to lysing tip of the embodiment depicted in FIG. 3d
FIG. 3i is a side perspective view of a bead of the embodiment depicted in FIG. 3d

FIGS. 3*b*, 3*c*, and 3*d* depict the system 300 in the treatment configuration in which the lysing plate is locked between the jaw assemblies 393/394 and held in place at the proximal lysing plate 360*p* and grasping terminus 361 by virtue of their fitting like a key and a lock into receiving slot 397 and electro-conductive opening-to-electroconductivity 387 in lower jaw covering 394*aa*.

FIG. 3*e* depicts the system 300 in the delivery/deployment configuration in which the lysing plate 360 is held approximately parallel to the axis of the shaft 390*a*. The proximal lysing plate 360*p* lies between the slightly open jaw assemblies 393/394. The proximal lysing plate 360 may be prevented from falling out of the jaws by virtue that the spheroid at the grasping terminus 361 being captured by the opening-to-electroconductivity 387 as well as, in some embodiments, a corresponding opening in the upper jaw assembly 393 to receive the upper portion of grasping terminus 361. Thus, upon delivery of lysing tip 310 into a human body, which may be done via cannula, for example, in the delivery configuration of FIG. 3*e*, the lysing tip 310 may be rotated and seated within receiving slot 397 in the treatment configuration of FIG. 3*d*.

In some embodiments, lysing member 360 may comprise a rigid and/or substantially rigid wire. In such embodiments, one or both of jaw assemblies 394/394 may be modified in shape at the treatment-position-locking-slot to accommodate the size of the rigid wire. In some embodiments, such a rigid wire may also comprise a grasping terminus, which may be provided at a distal end of the wire.

In some embodiments, spacers may be positioned adjacent to opposing beads 351 and/or between bead 351*a* and terminus 361 such that rotation or movement may be modified. Such spacers may be used to either inhibit or selectively limit rotation by, for example, their shape, and/or proximity to jaw assemblies 393/394. In this embodiment, a surgeon may be able to dissect on one or more of the sides on the backstroke, possibly making surgery more efficient. In some preferred embodiments and implementations, allowing for reverse dissection.

In alternative embodiments, beads 351 may be replaced with beads of any shape, including but not limited to those depicted in FIGS. 7*aa* to 7*zzz*. In some embodiments wherein a spacer is positioned between a lysing rod and grasper jaws, the tolerance between the lysing rod and a spacer may allow for rotation of the lysing rod within the spacer and thus allow for rotation of beads with respect to a spacer and/or grasper. The tolerance may be adjusted to allow for a predetermined amount of rotation.

In the depicted embodiment, a moveable sheath 395 external to the grasping control device 390 may reduce electrosurgical discharge by preventing upper and lower conductive jaw armature from being exposed to bodily fluids, charred material, and debris. The moveable sheath 395 may be slidably positionable along a substantial length of the shaft 390*a* of the grasping control instrument 390. Sheath 395 may be comprised of plastic, silicone, ceramic, cermet, halogenated hydrocarbon, and/or other nonconductive materials. Sheath 395 may be disposable to facilitate cleaning of the instrument 390 and/or replacement of sheath 395. Prior to use, sheath 395 may be slid into a position to expose the metal armature of the jaw assemblies to facilitate cleaning. During delivery and use, sheath 395 may be slid distally until the distal end of sheath 395 contacts one or both of ribs 389*a* of jaw coverings 393*aa*/394*aa*. Upper and lower jaw coverings 393*aa* and 394*aa* may be nonconductive and specially shaped with ribs 389*a* and/or ridges and/or surface features so as to prevent outer sheath 395 overlying shaft 390*a* from sliding to an unwanted position. Sheath 390 and ribs 389*a* as well, when suitably positioned, may form a seal to prevent unwanted electrical discharge. Another feature of ribs 389*a* is to provide the surgeon with a physical end point to the extension of sheath 395.

While the grasping/control instrument 390 is similar to grasping control instruments 190 and 290 such that when energized with electrosurgical energy, beads 351 and upper and lower jaw coverings 393*aa* and 394*aa* are preferably non-conductive, thus minimizing unwanted electrical discharge. Each upper and lower jaw assembly 393/394 respectively, may be comprised of upper and lower jaws 393*a*/394*a* (that may be conductive and/or metallic) and upper and lower jaw coverings 393*aa*/394*aa*, respectively. Upper and lower jaws 393/394 may comprise corresponding distal jaw tongues, as previously described. The inside of one or both non-conductive jaw coverings 393*aa* and 394*aa* may be formed with one or more receiving chambers 388*a* (receiving chamber for lower jaw covering 394*aa* not shown) respectively, to receive their corresponding conductive tongues. The electrically conductive tongues and/or may be configured to deliver electrosurgical energy through electrosurgical energy transfer opening 387 in one or more of the nonconductive jaw coverings 393*aa*/394*aa* in order to permit electrosurgical energy flow to or from one or more electro-conductive tongues to the terminus 361 of lysing plate 360. Nonconductive jaw coverings 393*aa*/394*aa* may be comprised of ceramic, cermet, glass, various halogenated hydrocarbons, and any other suitable nonconductors. Nonconductive jaw coverings 393*aa*/394*aa* may be restricted in their motion and/or affixed to conductive tongues via one or more cover welds placed in cover weld holes 393*c*/394*c*, said welds may be affixed to each tongue thus restricting movement of the corresponding jaw covering. When an electrosurgical generator is activated by a surgeon, electrosurgical energy may be transmitted through a metal pushrod, and/or linkage, as previously described. This energy may then be delivered through upper and/or lower jaws 393/394 through their respective jaw tongues. The pivot points along the electrical path may be coupled in ways commonly known in the art, for example, via pins.

Jaw assemblies 393/394 may be comprised of single action or double action jaws that may, but need not, open more than 10 to 15 degrees relative to one another in order to accept/capture the terminus 361 of lysing member 360.

In the depicted embodiment, 347 represents an antenna configured to deliver a signal to a receiver unit. In some embodiments, antenna 347 may comprise radiofrequency identification (RFID) TAG. In some embodiments the RFID tag may comprise an RFID transponder. In other embodiments the RFID tag may comprise a passive tag. It should be understood that antenna 347 is not depicted in every one of the other figures; any of the embodiments described herein may comprise one or more such elements. Other embodiments may comprise one or more antenna on any other suitable location on the embodiment, including but not limited to on the protrusions or otherwise on the tip, and on the shaft. In embodiments in which antenna 347 comprises an RFID transponder, the RFID transponder may comprise a microchip, such as a microchip having a rewritable memory. In some embodiments, the tag may measure less than a few millimeters. In some embodiments a reader may generate an alternating electromagnetic field which activates the RFID transponder and data may be sent via frequency modulation. In an embodiment, the position of the RFID tag or other antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency. Examples of potentially useful systems and methods for mapping/tracking a surgical instrument in relation to a patient's body may be found in U.S. Patent Application Publication No. 2007/0225550 titled "System and Method for 3-D Tracking of Surgical Instrument in Relation to Patient Body", which is hereby incorporated by reference in its entirety.

In some embodiments, a transmission unit may be provided that may generate a high-frequency electromagnetic field configured to be received by an antenna of the RFID tag or another antenna. The antenna may be configured to create an inductive current from the electromagnetic field. This current may activate a circuit of the tag, which may result in transmission of electromagnetic radiation from the tag. In some embodiments, this may be accomplished by modulation of the field created by the transmission unit. The frequency of the electromagnetic radiation emitted by the tag may be distinct from the radiation emitted from the transmission unit. In this manner, it may be possible to identify and distinguish the two signals. In some embodiments, the frequency of the signal from the tag may lie within a range of the frequency of the radiation emitted from the transmission unit. Additional details regarding RFID technology that may be useful in connection with one or more embodiments discussed herein may be found in, for example, U.S. Patent Application Publication No. 2009/0281419 titled "System for Determining the Position of a Medical Instrument," the entire contents of which are incorporated herein by specific reference.

In other embodiments, antenna 347 may comprise a Bluetooth antenna. In such embodiments, multiple corresponding Bluetooth receivers at known locations may be configured to sense signal strengths from the Bluetooth antenna 347 and triangulate such data in order to localize the signal from the Bluetooth antenna 347 and thereby locate the lysing tip within a patient's body. Other embodiments may be configured to use angle-based, electronic localization techniques and equipment in order to locate the antenna 347. Some such embodiments may comprise use of directional antennas, which may be useful to increase the accuracy of the localization. Still other embodiments may comprise use of other types of hardware and/or signals that may be useful for localization, such as WIFI and cellular signals, for example. Antenna 347 may be located within holes 355'.

One or more receiver units may be set up to receive the signal from the tag. By evaluating, for example, the strength of the signal at various receiver units, the distances from the various receiver units may be determined. By so determining such distances, a precise location of the lysing tip relative to a patient and/or a particular organ or other surgical site on the patient may be determined. In some embodiments, a display screen with appropriate software may be coupled with the RFID or other localization technology to allow a surgeon to visualize at least an approximate location of the tag/antenna, and therefore the lysing tip, relative to the patient's body.

Some embodiments may be further configured such that data from the antenna(s) may be used in connection with sensor data from the device. For example, some embodiments comprising one or more sensors 348 may be further configured with one or more RFID tags. As such, data from the one or more sensors may be paired or otherwise used in connection with data from the one or more RFID tags or other antennas. For example, some embodiments may be configured to provide information to a surgeon regarding one or more locations on the body from which one or more sensor readings were obtained. In some embodiments, temperature sensors may include thermistors and/or thermocouples. To further illustrate using another example, information regarding tissue temperature may be combined with a location from which such tissue temperature(s) were taken. In this manner, a surgeon may be provided with specific information regarding which locations within a patient's body have already been treated in an effective manner and thus which locations need not receive further treatment using the device.

In some such embodiments, a visual display may be provided comprising an image of the patient's body and/or one or more selected regions of a patient's body. Such a system may be configured so as to provide a visual indication for one or more regions within the image corresponding to regions of the patient's tissue that have been sufficiently treated. For example, a display of a patient's liver may change colors at locations on the display that correspond with regions of the liver that have experienced a sufficient degree of fibrosis or other treatment. Such regions may, in some embodiments, be configured such that pixels corresponding to particular regions only light up after the corresponding tissue in that region reaches a particular threshold temperature.

Such sensor 348 may be coupled with an antenna, which may send and/or receive one or more signals to/from a processing unit. Alternatively, or additionally, data from such sensors resulting from tissue and/or fluid analysis using such sensors may be stored locally and transmitted later. As yet another alternative, such a signal may be transmitted following surgery. In such implementations, the signals need not necessarily be transmitted wirelessly. In fact, some embodiments may be configured to store data locally, after which a data module, such as a memory stick, may be removed from the device and uploaded to a separate computer for analysis. Sensor 348 may be located within holes 355'.

In alternative embodiments, energy windows 306 may be positioned within bead holes 355' or on a surface of bead 351 and may be configured to deliver energy of a different type in a different direction. For example, in FIG. 3h, energy windows 306 may direct energy perpendicular to the forward motion direction of lysing tip 310 and/or may be configured to deliver another type of electrosurgical energy, or energy of different modalities, including, but not limited to, laser, intense pulse light, resistive heating, radiant heat, thermochromic, ultrasound, mechanical, and/or microwave.

FIGS. 4a-4j depict an embodiment of a CDTD or non-CDTD system 400. System 400 comprises a plurality of protrusions 401 defined by beads 451 and jaw covers 493aa/494aa and recessions 402 positioned in between adjacent beads 451 and jaw covers 493aa/494aa. System 400 comprises a lysing tip 410 that is configured to be completely separable from any other element of the system, however, lysing tip 410 may be configured to work in conjunction with the substantially ellipsoidal distal end of jaw assemblies 493/494 of grasping/control instrument 490 to serve as a "pseudo-bead" during an electrosurgical procedure. Lysing tip 410 comprises a plurality of beads 451 positioned on lysing member 460 which comprises lysing plate 460. Lysing plate 460 may also comprise a grasping/control instrument interface 461a which comprises a protruding conductive-metal hemisphere or other protruding member that is configured to be engaged with a corresponding feature on one or both jaw assemblies 493/494. It should be noted that in the embodiments of 4a-4j, beads 451 are supported laterally by lysing plate 460. It should also be noted that beads 451 lack a base, such as base 105 for system 100 detailed in U.S. patent application Ser. No. 15/464,199 and instead define a lysing tip that lacks structure immediately behind the beads for support. It should also be noted that lysing tip 410 comprises beads 451 that project both distally and proximally relative to lysing plate 460.

Grasping/control instrument 490 may comprise grasping channel 497 (which may further comprise an electrosurgical energy transfer opening 487. Channel 497 may be configured to receive and/or hold lysing plate 460. The leading edge of lysing plate 460 may comprise a beveled feature 460b which may cause the lysing tip 460 to rise when traversing tissue if positioned on the bottom of lysing tip 460. This feature 460b may also be sharpened to facilitate transfer of electrosurgical energy in a desired manner and/or allow for manually dissection in the absence of electrosurgical energy.

In the depicted embodiment, a moveable sheath 495 external to the grasping control device 490 may reduce electrosurgical discharge by preventing upper and lower conductive jaw armature 493a/494a from being exposed to bodily fluids, charred material, and debris. The moveable sheath 495 is usually present along a substantial length of the shaft 491 of the grasping control instrument 490. Sheath 495 may comprise plastic, silicone, ceramic, cermet, halogenated hydrocarbon, and/or other nonconductive materials. Sheath 495 may be disposable, thereby facilitating cleaning of the instrument and replacement of sheath. Prior to use, sheath 495 may be slid into a position to expose the metal armature of the jaw assemblies to facilitate cleaning. During delivery and use, sheath 495 may be slid distally until the distal end of sheath 495 contacts the most distal rib of ribs 489a of jaw coverings 493aa/494aa. Upper and lower jaw coverings 493aa and 494aa may be nonconductive and specially shaped with ribs 489a and/or ridges and/or surface features so as to prevent outer sheath 495 overlying shaft 491 from sliding to an unwanted position. Sheath 495 and ribs 489a may also, when suitably positioned, form a seal to prevent unwanted electrical discharge. In some embodiments, ribs 489a may also provide the surgeon with a physical end point to the extension of sheath 495.

While the grasping/control instrument 490 is energized with electrosurgical energy, beads 451 and upper and lower jaw coverings 493aa and 494aa are preferably non-conductive, thus minimizing unwanted electrical discharge. Each upper and lower jaw assembly 493/494 respectively, may therefore be comprised of upper and lower jaws 493a/494a (that may be conductive and/or metallic) and non-conductive upper and lower jaw coverings 493aa/494aa, respectively. Upper and lower jaws 493a/494a may comprise corresponding distal jaw tongues 493a'/494a'. The inside of one or both non-conductive jaw coverings 493aa and 494aa may be formed with one or more receiving chambers 488a (lower jaw covering depicted, upper jaw covering not depicted) respectively, to receive their corresponding conductive tongues 493a' or 494a'. The electrically conductive tongues 493a' and/or 494a' may be configured to deliver electrosurgical energy through electrosurgical energy transfer opening 487 in one or more of the nonconductive jaw coverings 493aa/494aa in order to permit electrosurgical energy flow to lysing plate 460

In this embodiment, opening 487 and slot 497 may be formed so as allow a portion of tongue 494a' to protrude into slot 497 to allow for direct contact between lysing plate 460 and tongue 494a', as best shown by the cross section in FIG. 4i. Nonconductive jaw coverings 493aa/494aa may be comprised of ceramic, cermet, glass, various halogenated hydrocarbons, and any other suitable nonconductors. Nonconductive jaw coverings 493aa/494aa may be restricted in their motion and/or affixed to conductive tongues 493a'/494a' via one or more cover welds placed in cover weld holes 493c/494c, said welds may be affixed to each tongue thus restricting movement of the corresponding jaw covering. When an electrosurgical generator is activated by a surgeon, electrosurgical energy may be transmitted through the metal pushrod 490p, through linkage 490L, and through upper and/or lower jaws 493a/494a coupled to jaw tongues 493a'/494a'. The pivot points along the electrical path may be coupled in ways commonly known in the art and as previously mentioned, for example, via pins.

Jaw assemblies 493/494 may be comprised of single action or double action jaws that may, but need not, open more than 10 to 15 degrees relative to one another.

In some embodiments, lysing tip 410 may be configured to prevent or limit lateral movement of outer beads 451 by, as previously described, joining spheroids or other objects via weld to lysing plate 460 within the intersection of plate tunnel 454 and bead holes 455 as described previously. In some embodiments, other objects may be welded or glued to effectively couple the beads 451 to lysing plate 460. In the depicted embodiment, metallic spheroids 460a such as ball bearings may be passed down bead hole and welded to the ends of or the top of the ends of lysing plate 460. Any suitable welding technique may be used, however, resistance welding may be preferred. In some embodiments, other geometric shapes may be used that prevent the lysing plate 460 from being withdrawn through/from tunnel. The spheroidal shape of a ball bearing or substantially spheroidal shape of a polyhedron may still allow for rotation of beads 451 provided the tunnel sizes and weld sizes permit. In some embodiments, pins, screws, rivets or the like or epoxy, or metallic welds may extend through vertical holes 455 to affix the two elements together. In alternative embodiments, holes 455 may be replaced by bevels. Thus, in some embodiments, horizontal and/or vertical tunnels may not be needed. However, in other embodiments, plate 460 may comprise beveled or narrowed regions configured to fit within such tunnels formed within beads 451. Because use of a plate 460 may provide more rigidity than certain other embodiments, use of spacers may not be needed for lysing tip 410. Beads 451 may comprise facets 452.

FIGS. 5a-h depict a TMT system 500 comprising a free-floating tissue modification tip (TMT) 511 that may couple to grasping/control instrument 590. In this embodiment TMT 511 may comprise a grasping terminus comprising a bulbous portion 506a. In the depicted embodiment, the grasping terminus comprises a metallic spheroid 506a, which may be configured to match the shape of a corresponding feature of one or both jaws of instrument 590. Although this shape may allow for some rotation/pivoting of tip 510 while within instrument 590, as described in greater detail below, other shapes are contemplated in which this shape may vary. Thus, the grasping and/or bulbous terminus 506a may comprise a geometrically shaped terminus 506a such as polyhedron, etc. Upon being grasped by grasping/control instrument 590 to perform a surgical procedure, in some embodiments, energy, such as electrosurgical energy, may be delivered from one or both of jaw assemblies 593/594 of instrument 591, such as tongues 593aa/594aa of these jaws. As previously mentioned, the inside of one or both of these jaws may define a receiving slot 597, which may be configured to engage terminus 506a and allow for contacting with a conductive portion of one or both jaws, electrosurgical energy transfer opening 587. In some embodiments, receiving slot 597 may be formed in a cover, as previously mentioned, that may fit over one or both jaws of instrument 590. Alternative embodiments are contemplated, however, in which receiving slot 597 may be formed directly in one or both of the jaws themselves.

In the depicted embodiment, receiving slot 597 may comprise a treatment locking portion 597a, which may comprise a flattened groove, which may be configured to match the shape of tip 511 at one end near terminus 506a, such as at flattened region 506. Receiving slot 597 may further, or alternatively solely, comprise a rotational portion 597b, which may comprise a rounded opening, which may be configured to rotationally engage bulbous terminus 506a and allow for rotation between the delivery configuration of FIG. 5b and the treatment configuration of FIG. 5a. In some embodiments, a similar rotational slot may be formed in the opposing jaw. In the depicted embodiment, receiving slot 597 may also serve as an opening for delivery of electrosurgical energy from instrument 590 through a jaw cover via electrosurgical energy transfer opening 587 and into a conductive portion of tip 511.

More particularly, tip 511 comprises an energy window 508o that may be positioned to face an upper and/or lower tissue plane that may have already been lysed/dissected. A non-conductive cover 508 may have one or more windows 508o that may allow for a conductive element 506t to extend therethrough to provide for delivery of energy, electrosurgical or otherwise, therethrough. In alternative embodiments, one or more bars or other structural elements may be formed in cover 508, which may separate an elongated energy window 506t into a plurality of isolated energy windows. Although energy window 506t is in the shape of a bar, a wide variety of alternative shapes and sizes of energy windows and/or structures for defining emission regions of energy windows may be provided as desired. In some embodiments, cover 508 may be formed with a plurality of circular opening. Cover 508 may be over-molded onto tip

511. Cover 508 may be produced in two pieces that couple around the metal member 506. In alternative embodiments, the region of energy window 506*t* may comprise one or more (a plurality of) energy emitters positioned in a manner to optimize the intended tissue modification effect.

As previously mentioned, rotational portion 597*b* may coincide with an opening 587 in lower jaw covering 594*aa*. Upon placement of the grasping/bulbous terminus 506*a* into the opening-to-electroconductivity 587 of the receiving slot 597, if electrosurgical energy is applied to the grasping/control device 590, electrosurgical energy may pass through the energy window 506*t* into target tissues when in proper proximity. Preferably, bulbous terminus 506*a*, opening 587, and jaw 594 are configured so as to facilitate direct contact between a conductive jaw or jaw portion and bulbous terminus 506*a*. Grasping/control instrument 590 may comprise shaft 591, pushrod 592, and jaw assemblies 593/594 which may be covered by moveable, non-conductive sheath 595.

In alternative embodiments, energy window 506*t* may be configured to be positioned on the bottom of the device. However, in various implementations, a surgeon may simply invert the tip of a top-mounted energy window 506*t* so that it points in the opposite direction (for example, away from the surface skin and toward the subcutaneous tissues. This inward/subcutaneous direction of energy may be useful in directing energy toward the subcutaneous deposits in cellulite and other cosmetic conditions.

Some embodiments may comprise an energy window 506*t* located proximally to protrusions 201. In the depicted embodiment, energy window system 506*t* may comprise electrode termini which may be supplied energy from an energy source via conduits (not shown) that may comprise, for example, wires and/or fiber optic filaments and/or the like. Energy window 506*t* may be configured in any manner to accommodate any energy modality, including, but not limited to, laser, intense pulse light, resistive heating, radiant heat, thermochromic, ultrasound, mechanical, and/or microwave.

Figures 6A, 6B:
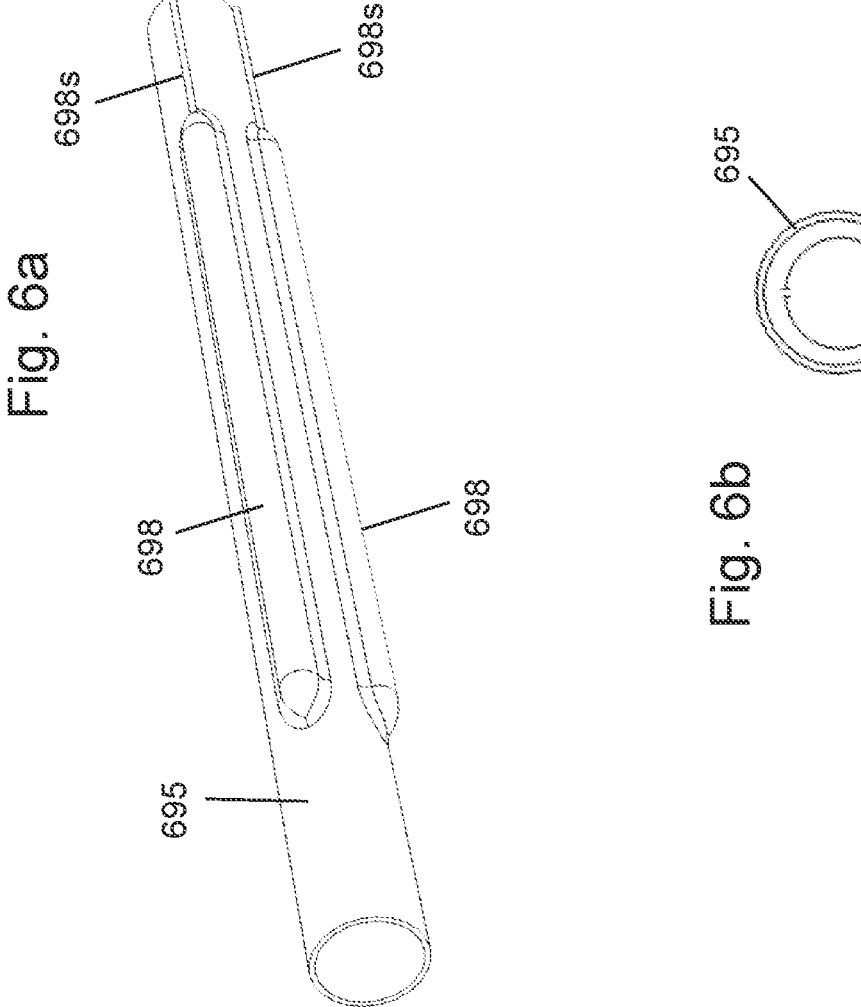

In other embodiments depicted in FIGS. 6*a-b*, the external sheath 695 or, in alternative embodiments, an external surface of a grasping and/or control instrument, may comprise inflatable segments 698 along a portion of the shaft and/or sheath 695, preferably along a distal portion of the shaft and/or sheath 695. Longer cannulas may tend to be less controllable for more distant applications from the entrance wound. Thus, these inflatable segments 698 may be useful especially in cosmetic procedures, such as cellulite treatment, in order to force the jaws and lysing rod/segment more superficially against the lower dermis. In the depicted embodiment, two balloon-like, tube-shaped, inflatable segments 698 may be present on the distal to mid-distal portions of the sheath. One or more supply tubes 698*s* may be coupled to the inflatable segments 698. Inflatable segments 698 may measure half the diameter of sleeve 695. However, in other embodiments, inflatable segments 698 may vary from ¹⁄₁₀th the diameter of the sheath to 10 times the diameter of the sheath. Inflatable segments 698 may expand in size (for example, from about 10% to about 10,000%) when filled with fluid, which may include gas, water, carbon dioxide, nitrogen, and the like. The presence of the inflated segments 698 may facilitate surgery in more distal locations from the entrance wound. Inflatable segments 698 may be deflated prior to removal of the device. The balloon-like segments 698 may be part of the sheath or may be otherwise attached to the sheath, for example, by glue or heat seal and/or ultrasonic seal. Or, as mentioned above, the balloon-like segments 698 may be coupled with a portion of the instrument itself, such as a suitable external surface of the instrument in the event that a sheath is not needed. Inflatable segments 698 may number from 1 to 10 on a given sheath. Inflatable segments 698 may be comprised of silicone, rubber, plastic, halogenated hydrocarbon, silastic, vinyl, and the like.

In alternative embodiments, inflatable segments 698 may be replaced with another means for pressing a portion of a control instrument and/or lysing tip against a tissue to direct the lysing tip towards a desired treatment tissue in a direction normal or at least substantially normal to an axis of the control instrument. For example, inflatable segments 698 may be replaced with mechanical jack or lift assembly, which may similarly be positioned on an exterior surface of a sheath or instrument. Such mechanical jack/lift assemblies are another example of a means for pressing a portion of a control instrument and/or lying tip against a tissue to direct the lysing tip towards a desired treatment tissue in a direction normal or at least substantially normal to an axis of the control instrument.

FIGS. 7*a*-7*zzz* depict 3 general components of the lysing tip and various potential shapes: Lysing rod (FIGS. 7*a*-7*g*), spacers (FIGS. 7*h*-7*t*), and beads (FIGS. 7*aa*-7*zzz*).

FIGS. 7*a*-7*g* depict various examples of cross-sectional shapes of wires or other lysing members. In some embodiments, these shapes may be formed by crimping a wire or other suitable lysing member into the desired shape. Crimping the lysing member may be particularly useful in connection with certain embodiments and/or implementations of the invention, as it may facilitate a preferred coupling between various other elements of the CDTD system, such as the beads and/or spacers. Crimping may also, or alternatively, be useful in providing for a preferred delivery of electrosurgical energy through the wire/lysing member. Other methods of shaping the lysing member may include but not be limited to cutting, polishing, forging or forming by extrusion. In additional embodiments, various coatings may be applied to lysing rods that may reduce adhesion of heated biological material to the lysing rod or spacers.

FIG. 7*a* comprises a lysing rod having a circular cross-section. The shape of lysing member/lysing rods may also be important as to the most efficient and safe means to transfer electrosurgical energy from the lysing members to the tissue(s). Electrosurgical energy on/under a surface may tend to move toward edges of an object. This shape may be useful for allowing a useful distribution of a coating to the surface of the lysing rod that may be used to reduce char buildup and/or modify ease of movement of a lysing tip through tissue. FIG. 7*b* comprises a lysing rod having a triangular cross-section; this may be useful for maximizing electrosurgical energy discharge and minimizing char build-up about the lysing rod. FIG. 7*c* comprises a lysing rod having a square cross-section. FIG. 7*d* comprises a lysing rod having a pentagonal cross-section along its length while FIG. 7*dx* comprises a lysing rod having a pentagonal cross-section that is twisted along its length. FIG. 7*e* comprises a lysing rod having a hexagonal cross-section. FIG. 7*f* comprises a lysing rod having a wedge-shaped cross-section. FIG. 7*g* comprises a lysing rod having a semi-circular or frusto-circular cross-section.

FIGS. 7*h*-7*t* depict various shapes for spacers that may be used in connection with one or more of the embodiments disclosed herein. Each may have a hole through which lysing members may extend. As illustrated in these figures, FIG. 7*h* illustrates a spacer having flat ends and a cylindrical shape. FIG. 7*i* illustrates a spacer having a circular cross-section and tapered ends which may be useful for allowing a desired distribution of a coating to the surface of the spacer to reduce char buildup and/or modify ease of movement of a lysing tip through tissue. FIG. 7*j* comprises various openings, such as holes, for delivery of electrosurgical energy therethrough; this may allow for making spacers of a non-conductive material and still deliver such energy therethrough. FIG. 7*k* illustrates an alternative spacer that is arced. FIGS. 7L (resting) and 7*m* (stressed) illustrate an alternative spacer having opposing loops with central openings configured to allow for receipt of a wire or other lysing rod therethrough and a flexible connector extending between the two loops. As shown in FIG. 7*m*, once coupled with adjacent beads (not shown), the flexible connector may bend to serve as a brace and space apart the adjacent beads. This spacer may also be configured such that the opposing loops may be flexed to the side to allow for coupling of adjacent beads and receipt of a lysing rod therethrough (not shown). FIG. 7*n* illustrates a cross-sectional view of another spacer having a triangular cross-sectional shape and an opening for receipt of a lysing rod therethrough. FIG. 7*o* illustrates a cross-sectional view of another spacer having a rectangular cross-sectional shape and an opening for receipt of a lysing rod therethrough. FIG. 7*p* illustrates a cross-sectional view of another spacer having a pentagonal cross-sectional shape along its length and an opening for receipt of a lysing rod therethrough while FIG. 7*px* comprises a spacer having a pentagonal cross-section that is twisted along its length and an opening for receipt of a lysing rod therethrough. Spacers with twisted features may acquire less debris along its surface and may tend to rotate thus multiple sides of a spacer are exposed to charred tissue. FIG. 7*q* illustrates a cross-sectional view of another spacer having a hexagonal cross-sectional shape and an opening for receipt of a lysing rod therethrough. FIG. 7*r* illustrates a blade-style cross-sectional shape with smooth, rounded outer surfaces that meet at the distal edge and an opening for receipt of a lysing wire or other lysing rod therethrough. FIG. 7*s* illustrates a cross-sectional view of another spacer having a blade cross-sectional shape (differing from FIG. 7*r* in that outer surfaces are formed by intersecting planar/flat surfaces) and an opening for receipt of a lysing wire or other lysing rod therethrough. FIG. 7*t* illustrates a cross-sectional view of another spacer having a spindle cross-sectional shape and an opening for receipt of a lysing wire or other lysing rod therethrough.

The cross-sectional shape of the exterior surface of spacers may also be important as to the most efficient and safe means to transfer electrosurgical energy from spacers to the tissue(s). Electrosurgical energy on/under a surface may tend to move toward edges of an object, so a spacer with an exterior surface having a circular cross section may force current to the opposing spacer ends creating hot spots at/near adjacent beads. Therefore, it may be beneficial for spacers to comprise an exterior surface having a non-circular cross section with one or more substantially uniform edges along its length from which electrosurgical energy may uniformly be transferred to tissues. In contemplated embodiments, a pentagonal or hexagonal cross-sectional shape may be preferable. Additionally, spacers with non-circular cross-sections may accumulate less debris and/or eschar on lysing rod and/or spacer because debris may have a more difficult time adhering to an angled edge. In some embodiments, one or more (in some embodiments, all) of the spacers may comprise a leading edge for delivery of electrosurgical energy from the lysing member(s). In some such embodiments, one or more of the spacers may comprise only a single such leading edge. In some such embodiments, the spacer(s) may comprise a smooth, or at least substantially smooth, exterior surface, other than the single leading edge. For example, the spacer(s) (or, in some embodiments, the lysing member/rod itself) may comprise a circular or oval shape in cross section with a flattened leading end terminating in a leading edge. This may be useful for controlling the delivery of electrosurgical energy.

Because the spacers may be configured to receive the lysing member/rod therethrough, the spacers may also comprise an opening extending therethrough for receiving the lysing member/rod. Thus, the spacers may also have an interior cross-sectional shape, which may differ from the shape of the exterior surface. For example, it may be useful to form the spacers with an opening having a cross-sectional shape that matches the cross-sectional shape of the lysing member/rod. Thus, if the lysing member/rod comprises a circular or polygonal shape in cross-section, the spacer(s) may comprise an opening having a similar cross-sectional shape. In some embodiments, the shape of the exterior surface of the spacers may therefore be used to primarily dictate preferred delivery locations for the electrosurgical energy.

FIGS. 7*aa*-7*zzz* show alternative shapes for beads positioned along a lysing tip. As illustrated in these figures, bead shapes that may be useful may include spheres (FIG. 7*aa*), wheel shapes (FIG. 7*bb*), dodecahedron shapes (FIG. 7*cc*). In other embodiments, bead shapes may be bullet-shaped or partially or substantially ellipsoidal (FIGS. 7*dd*-7*ff*) and may have facets (FIGS. 7*ee* and 7*ff*). In other contemplated embodiments, beads of various geometries may be cut off having flat or slightly curved proximal surfaces or further shaped by geometric cuts (FIGS. 7*gg*-7LL) (herein, this may be referred to as "frusto-shaped"). In other contemplated embodiments, bead shapes and/or tunnels through them may be uniform spherical and/or centered. In other contemplated embodiments, beads may have skeleton features supported by a hub that may be adjacent to the lysing rod or adjacent to or formed around a ceramic sleeve through which a lysing rod is extended (FIGS. 7*mm*-7*rr*). In some contemplated embodiments, providing a rough trailing end may create frictional drag on that portion of the bead thus helping reorient the front end of the bead for further tissue passage. Thus, in some embodiments, the trailing end may have a rougher surface than the front end. For example, in some embodiments, the trailing end, or at least a portion of the trailing end, of one or more beads may be sanded with a rougher sanding material than the leading end, may be formed with ridges, grooves, or other roughening elements, or may otherwise be made with a less smooth surface for this purpose. In some contemplated embodiments such as that depicted in FIG. 7*rr*, a bead may comprise a slot beginning at its trailing end and terminating within the bead 7*rr* so as to allow for receipt of a lysing rod therein. In some such embodiments, a hole 755 may be positioned to extend through the bead and may at least partially intersect with slot 753. Thus, a weld, plug, glue, insert or other method of fixation may be inserted via hole 755 to attach to a lysing rod thus restricting movement of a bead and/or rotation of the bead with respect to its lysing rod.

In alternative embodiments, beads may comprise a conductive material such as metal and coated with an insulator; for example, a bead shaped such as FIG. 7*rr* but made of metal (internally) may be pressed over a lysing rod with increased pressure closing the slot behind the lysing rod causing the bead to remain in place along a lysing rod.

In alternative embodiments such as in FIGS. 7ss-7yy, beads may be flattened, curved, hollowed-out or distorted in one or more axis. Curved beads such as those depicted in FIGS. 7xx and 7yy may allow for redirection of the tip in various tissues. As well, flattened beads, such as those in FIG. 7ww or other shapes depicted herein, may be tilted or bound on one or more axes that redirect the angle of attack and/or tissue passage to an angle different than the primary axis of the shaft of a lysing tip or the guiding shaft coupled to the lysing tip.

In still other embodiments, beads with shapes as those depicted in 7zz and 7zzz may comprise surface regularities or one or multiple surface irregularities, respectively.

In still other embodiments, a particular lysing tip may comprise one or more bead shapes.

FIGS. 8a-8b depict an embodiment of a system 800 and illustrate some of the steps involved in an implementation for introducing detachable lysing tip 810 into the body with grasping/control instrument 890 and/or transfer/grasping instrument 896 by way of cannula 832, which may be a trocar. Transfer/grasping instrument 896 may be delivered by way of a second cannula 835. As depicted in FIGS. 8a-b, lysing tip 810 may be delivered through a first/primary cannula 832, which may comprise, for example, a trocar, and then coupled with a first surgical tool, such as a grasping/control instrument 890 that can be used to control and/or energize the lysing tip 810 within the body of a patient during a surgical procedure. In some embodiments and implementations, a second cannula 835 may be used to deliver a second surgical tool, such as a transfer/grasping instrument 896, that may be used to facilitate coupling of lysing tip 810 to the grasping/control instrument 890, which instrument may be delivered through the same cannula 832 through which the lysing tip 810 is delivered. In some embodiments, grasping/control instrument 890 may have the same configuration as grasping/transfer instrument 896. In alternative embodiments, transfer/grasping instrument 896 may be configured differently from grasping control instrument 890 in that, for example, it may not have the capability to transfer energy to lysing tip 810 and/or may have a different jaw and/or tip design in order to facilitate grasping/holding lysing tip 810 between two beads or other protrusions. Alternatively, the lysing tip 810 may be delivered though a second unattached cannula 835 along with a grasping/transfer instrument 896 used to couple the lysing tip 810 to the first surgical tool delivered through the first/primary cannula, which other surgical tool may be used to control lysing tip 810 and perform the surgical procedure. As shown in the FIG. 8a, lysing tip 810 is positioned within outer cannula 832 with an axis extending between the beads 851 in lysing tip 810 aligned with a primary axis of cannula 832 and with a treatment side of lysing tip 810 facing an internal surface of cannula 832.

In some implementations of methods using system 800, the lysing tip may be reconfigured from a delivery configuration to a treatment configuration by delivering lysing tip 810 through a cannula at least substantially along a treatment axis of the lysing tip extending between opposing outer beads and then rotating the lysing tip once outside the distal end of the cannula. In some such implementations, the step of reconfiguration of the lysing tip from delivery to treatment configuration may further comprise grasping a portion of the lysing tip in a manner such that the lysing tip axis is at least substantially perpendicular to an axis of the grasping instrument.

As also depicted in FIGS. 8a and 8b, lysing tip 810 further comprises a grasping tab 860t coupled to the lysing rod 860 of lysing tip 810. In some embodiments, grasping tab 860t may be configured to facilitate transfer of lysing tip 810 from a delivery to a treatment configuration by being configured for being grasped by instrument 896 after lysing tip 810 has been advanced through the distal opening of cannula 832. In preferred embodiments, grasping tab 860t may be configured dissolve and/or biodegrade upon application of electrosurgical energy to lysing rod 860. For example, grasping tab 860t may comprise a biodegradable substance which may also comprise absorbable suture, gelatin, wax, polyglycaprone, polyglycolic acid, polylactic acid, and/or polydioxanone. While opposing grasping instrument 896 is temporarily grasping tab 860t, the jaws of the treatment/grasping instrument 890 may lock down on the desired portion of the lysing rod 860 and/or another portion of lysing tip 810. Once the device is electrosurgically activated and discharges energy and significant temperatures are generated, the tab 860t may be configured to melt or decompose thus exposing the desired portions of lysing rod 860 so treatment may commence. Once the tab 860t has been melted or otherwise removed from lysing rod 860, preferably tab 860t is bioresorbable and/or bioabsorbable and therefore need not be removed from the body following the procedure.

In alternative implementations, a standard 3-5 mm diameter grasping instrument with handle (without a lysing tip attached) may be directed into the body cavity, possibly via a trocar of accepting diameter or via an incision in the skin, and exit extracorporeally via another trocar (for example, of larger diameter at umbilicus), whereupon the grasper may open and receive the lysing tip at an angle that permits the grasper to pull lysing tip into the body cavity through the larger trocar. Once inside the body cavity, the lysing tip may be reconfigured from a delivery configuration to a treatment configuration.

In alternative embodiments, the transfer grasping instrument may comprise at the distal end other means for grasping the lysing tip 810 such as a hook and/or magnet and/or glue.

An alternative system for use of a lysing tip 814t with a modular grasping instrument tip 814g is shown in FIGS. 8c and 8d. In some embodiments, modular instrument tip 814g and lysing tip 814t may be permanently coupled to one another as described below. Alternatively, in other embodiments, lysing tip 814t may be removable from modular instrument tip 814g. When the instrument tip 814g and lysing tip 814t may be combined, they may be referred to herein as a modular grasper/tip 814. Modular instrument tip 814g comprises a locking lumen 897' that is configured to be coupled with a distal end of a pushrod 897 and shaft 896 of a modular grasping/control instrument 90.

In an example of a procedure using the system of FIG. 8c, a surgeon may initially place a trocar 832' at a desired location such as through an incision 6' positioned through the umbilicus 5. A second incision 6, which may be a smaller incision than incision 6', may be made at a location spaced apart from incision 6'. In some embodiments and implementations, incision 6 may be between about 2.5 and about 5 mm. Shaft 896 of instrument 90 may then be extended through incision 6 and then subsequently through incision 6' and trocar 832'. Modular grasping instrument 814g may then be coupled with the distal end of shaft 896 and push rod 897. Once lysing tip 814t is coupled with modular grasping instrument tip 814g, instrument 90 may then be pulled proximally to introduce lysing tip 814t within patient 4. In embodiments in which lysing tip 814t is removable from modular grasping instrument tip 814g, lysing tip 814t may be coupled with the distal end of instrument tip 814g prior to proximally pulling instrument 90 and its distal tip back into the cavity of human or animal body 4. Once modular instrument tip 814g has been coupled with instrument 90, handle 91 may be used to control one or more aspects of lysing tip 814t. For example, actuation of handle 91 may result in locking lysing tip 814t at a particular rotational orientation relative to shaft 896. Alternatively, handle 91 or another actuation element of instrument 90 may be used to rotate lysing tip 814t between delivery and treatment configurations. Instrument 90 may also be used to deliver electrosurgical energy to lysing tip 814t. For example, as shown in FIG. 8c, energy connector 92, which may comprise a conductive post may be used to facilitate an electrical connection with an electrosurgical generator. The electrosurgical energy from this generator may extend through shaft 896 via pushrod 897 and be coupled with one or more lysing members of lysing tip 814t, as previously described.

FIG. 8d depicts a more detailed view of the interface between modular grasping instrument 814g and distal tip of shaft 896 and pushrod 897 of instrument 90. As shown in this figure, the distal end of shaft 896 may comprise a locking feature 898. Locking lumen 897' within modular instrument tip shaft 894 comprises a slot 899s configured to receive locking feature 898 at a predetermined rotational configuration. Upon aligning locking feature 898 with slot 899s, shaft 896 and pushrod 897 may be advanced into locking lumen 899'. After advancing shaft locking feature 898 to its terminal end 898' within coupling rod 892, upon rotation 2 of modular instrument tip shaft 894, locking feature 898 securely couples shaft 896 to coupling rod 892. During the same time period, pushrod 897 and its accompanying pushrod locking feature 899n was advanced to a locking chamber 899n' in which pushrod 897 and its accompanying pushrod locking feature 899n may have been rotated to lock pushrod locking feature 899n in place within locking chamber 899n'. Locking feature 899n preferably comprises a flattened or otherwise asymmetrical piece such that rotation of shaft 896 may result in locking feature 899n engaging a ledge or other locking feature of locking chamber 899n'. In some embodiments, the extent of the rotation of pushrod locking feature 899n may be the same as the extent of rotation of locking feature 898 which may, in some embodiments, be 90 degrees. In some embodiments, pushrod locking feature 899n may comprise a plate or an elongated box or any other feature not having rotational symmetry about the axis pushrod 897. Locking chamber 899n' may comprise, for example, a box or other similar feature given to engage pushrod locking feature 899n upon rotation of pushrod 897.

Locking chamber 899n' is coupled with coupling rod 892 which in turn may be coupled with one or both jaws. Thus, upon advancing or retracting pushrod 897, coupling rod 892 advances or retracts to open or close the jaws so as to capture support member 870 within jaws 893b.

Any of the systems discussed herein may be configured to have their corresponding lysing tips delivered into the body in one or more of the methods described above.

FIGS. 9a-9L depict an alternative embodiment of a CDTD system 900 comprising a plurality of protrusions 901 defined by beads 951 and jaw covers 993aa/994aa and recessions 902 positioned in between adjacent beads 951 and jaw covers 993aa/994aa. System 900 comprises bipolar electrosurgical system. System 900 is configured for bipolar electrosurgical energy delivery and comprises lysing tip 910 that may have 3 protrusions defined by two outer beads 951 and the tip of a laparoscopic grasping instrument simulating the geometry of a middle bead, and 2 lysing segments 961cn/961cp defined by two electrically isolated lysing members 961p/961n.

An electrosurgical grasping/control instrument 991 may be used to deliver electrosurgical energy to lysing tip 910 and control lysing tip 910 during a surgical procedure. Instrument 991 may comprise one or more push rods 992 that may be used to control one or both jaws 993 and 994 and/or deliver electrosurgical energy into tip 910. As previously described, jaws 993 and 994 may each comprise a conductive core or tongue 993a'/994a' and an insulting cover 993aa/994aa. One or both of upper and lower jaw covers 993aa and 994aa may comprise an electrosurgical energy transfer opening configured to allow for contact with conductive portions of tip. These portions may be of opposite polarity and electrically isolated from each other along their paths. This may require that the entire housing and core components of, for example, the upper jaw be made of a ceramic or other non-conductor with perhaps the use of a wire lead that would be electrically isolated from the connected to the upper jaw electrosurgical energy transfer opening 987. For example, energy may flow from the electrosurgical energy transfer opening 987 of the lower jaw into the lysing segment on the side contacting the lower jaw 961n; energy then flows from the lysing segment 961n into the target tissues cutting and/or coagulating the target tissues and energy returns into the opposite side lysing segment 961p and into the, for example, electrosurgical energy transfer opening 987 of upper jaw assembly 993 and then to its electrically isolated lead and back to the electrosurgical generator.

As depicted in FIG. 9e, lysing tip 910 may comprise a bar or plate region 956 between opposing beads to support the beads from the sides. This region may comprise opposing wings 956w defined in part by a central grasping pad 956g that may be recessed from opposing wings 956w. Grasping pad 956g may be configured to be engaged by one or both jaws 993/994. Preferably, the entire portion of tip 910 depicted in FIG. 9e is made up of a ceramic or other non-conductive material. In some embodiments, beads 951 may be coupled with the central portion of lysing tip 910. Alternatively, beads may be formed so as to be an integral part of the non-conductive portion of lysing tip 910.

Isolated conductive lysing members 961p and 961n, as shown in FIGS. 9f and 9g, may be positioned within the portion of tip 910 depicted in FIG. 9e to define a complete lysing tip. As shown in FIG. 9e, slots 956sn and 956sp may be provided in lysing tip 910 to allow the lysing edges 961cn and 961cp of lysing members 961p and 961n to protrude from the non-conductive body of lysing tip 910 and define lysing segments. In addition, openings may be provided in the non-conductive body to allow for receipt of electrosurgical energy into lysing members 961p and 961n. More particularly, as shown in FIG. 9e, an upper opening 956hp may be provided in the upper portion of grasping pad 956g, through which a projection and/or prong, such as terminal post 961tp, of lysing member 961p, may extend. Although not visible in FIG. 9e, a similar opening may be formed in the lower surface of grasping pad 956g for receipt of terminal post 961tn of lysing member 961n. Contact between these various posts and conductive jaw tongues through openings in a non-conductive portion of lysing tip 910 can be seen in FIGS. 9h-9L.

Preferably, the respective terminal posts or other projections of the lysing members protrude beyond the opposing surfaces of grasping pad 956g to allow them to make contact with a conductive portion of opposing jaws 993/994, such as conductive tongues 993a'/994a'. As previously mentioned, openings 987 may be formed in jaw covers 993aa/994aa to allow for such contact. In addition, slots 997 may be formed in the jaw covers of upper and lower jaws 993 and 994 to allow for grasping pad 956g to fit therein. Slots 997 may be formed so as to partially define openings 987 as shown in FIG. 9I.

FIGS. 9j and 9k depict two cross sectional views of system 900 in a direction along the axis of grasping control instrument 990, one at the center of terminal post 961tp and the other at the center of terminal post 961tn respectively. FIG. 9j shows terminal post 961tp contacting upper jaw tongue 993a' while FIG. 9k shows terminal post 961tn contacting lower jaw tongue 994a'.

A non-conductive cover or sleeve 995 may be positioned on a distal portion of instrument 991 in some embodiments, as shown in FIG. 9a.

The relative static permittivity of some ceramics may range from about 5 to 10; this may cause some leakage of current in an undesirable path between closely approximated opposing electrodes during activation. Use of other materials, for example, those having over of relative static permittivities of 5 may undesirably alter the resultant plasma field. The relative static permittivity of the intervening materials housing the opposing electrodes may be enhanced by coating and/or surrounding and/or injection molding thermoresistant polymers of a low relative static permittivity into the housing and/or around one or more portions of bipolar lysing segments 961n/961p to reduce the effective static permittivity of the tip. In an embodiment, the thermoresistant polymer of low relative static permittivity 2.1 may be polytetrafluoroethylene. In other contemplated embodiments, thermoresistant polymers may include polyether etherketone (@3.3) and/or polysulfone (@3.1) and the like may be useful.

In the depicted embodiments, electrical insulator to isolate one or more components or the electrical path to and from the electrosurgical generator may comprise polytetrafluoroethylene. In other contemplated embodiments, the electrical insulator may comprise an electrically nonconductive polymer with a high melting temperature. In some embodiments, the nonconductive polymer may comprise for example, polyether etherketone and/or polysulfone, etc. In other contemplated embodiments, the electrical insulator may comprise an electrically nonconductive and/or thermally nonconductive polymer.

As of the year 2000, the bipolar mode had traditionally been used primarily for coagulation (reference: "The Biomedical Engineering Handbook, Electrosurgical Devices" J Eggleston, W Maltzahn, Ch 81, CRC Press 2000). However, more recent modifications to bipolar electrosurgical outputs may have facilitated the use of bipolar cutting instruments (reference: ValleyLab, Hotline, vol. 4, issue 4 pg. 1), examples of such outputs may include Macrobipolar settings (Reference: ValleyLab ForceTriad Users Guide 2006, chapter/sections: 9-13, 9-16, 9-24).

After application of the TD and/or Heater to the cellulite treatment zone, within approximately 2 to 8 months, the surgeon may inject fluid, including but not limited to tumescent fluid, into and around the treatment zone to stretch the previously treated area. Inflating the treatment zone with fluid and/or gas may tend to separate, stretch, or deform unwanted tendrils or deposits that may be tending to reform or reorganize in the post-surgical treatment zone. The amount of fluid needed may vary from 0.5 cc to 2.0 cc per sqcm. Even larger amounts of fluid per sqcm may be administered depending upon the clinical situation as perhaps the greater the stretch, the longer the duration of surgical result. The fluid may be administered by injection needle, spatula cannula, or any suitable percutaneous device. It may be desirable to have a long injection system for example a 40 cm long spatula cannula so that the entrance wound for the cannula may be placed in a non-conspicuous location. The fluid may be administered under pressure as well via peristaltic pump, elevated IV bag, or mechanical injection mechanism. The process may be repeated every 2 to 8 months, possibly indefinitely to help maintain the surgical result.

FIGS. 10a-10k depict an embodiment of a lysing instrument 1000. Instrument 1000 may comprise shaft 1090 and two-way lysing tip 1033. Lysing tip 1033 is configured for two-way motion (i.e., forward/distal and reverse/proximal motion) due to, as discussed below, the presence of lysing segments that face in the forward/distal direction to facilitate forward motion of lysing tip 1033 through tissue and other lysing segments that face in the rearward/proximal direction to facilitate rearward/proximal motion of lysing tip 1033 through tissue. Shaft 1090 may physically couple lysing tip 1033 to an electrosurgical energy source such as an electrosurgical pencil (not shown) via conductive insert 1060s, which in the depicted embodiment comprises a conductive rod, which may be electrically conductive and act as a conduit for electrosurgical energy to flow to lysing tip 1033. In the depicted embodiment, conductive insert 1060s comprises an integral extension from electrode 1060. In other contemplated embodiments, however, conductive insert 1060s may be coupled to electrode 1060, either directly or indirectly such as by way of a wire or the like.

Lysing tip 1033 comprises one or more distal-facing lysing segments and one or more proximal-facing lysing segments. Each of these various lysing segments may be defined by a single electrode or each by its own respective electrode. In the depicted embodiment, a single electrode 1060 is used to define each of the various lysing segments and a shaped non-conductive body 1033b is used to define various beads, protrusions, and/or other features that define recessions into which the lysing segments are positioned. Non-conductive body 1033b defines two (or more, as shown in other embodiments) forward-facing distal protrusions 1001d defined by the distal tips 1051d of beads 1051 and a distal recession 1002d (more than one distal recession may be provided on other embodiments) positioned between distal tips of beads 1051d. Lysing tip 1033 may further comprise one or more rearward-facing proximal protrusion/recession lysing segments or lysing segment pairs as well to facilitate proximal motion of the device 1000 through tissue. For example, beads 1051 further define rearward protrusions defined by the proximal tips 1001p of beads 1051 and recessions 1002p defined by proximal tips 1001p along with the shaft/neck of lysing tip 1033.

Shaped nonconductive body 1033b may comprise one or more beads 1051 that may be supported by and/or spaced by one or more rigid or substantially rigid struts 1080, each of which may be permanently or temporarily coupled between adjacent beads 1051 and, in some embodiments, may be further coupled along a proximal region with the shaft of lysing tip 1033. In the preferred embodiment shown in FIGS. 10a-10g, shaped nonconductive body 1033b may comprise slot 1080s that may extend between strut 1080. Slot 1080s may define a distal slot opening 1080sd defined on its upper and lower sides by strut 1080 and on its left and right sides by one or more tunnels 1051t in beads 1051.

In this embodiment, electrode 1060 may be passed through distal slot opening 1080sd and operationally positioned and configured for lysing segment 1060d, which is defined by an exposed portion of electrode 1060, to face distally through distal slot opening 1080sd and to allow for delivery of electrosurgical energy therethrough. Shaped nonconductive body 1033b may further comprise one or more proximal slot openings 1080sp through which the proximal lysing segments 1060p of electrode 1060 may be exposed to allow for delivery of electrosurgical energy therethrough and to facilitate rearward movement of lysing tip 1033 through tissue.

Beads 1051 and strut 1080 may be comprised of ceramic, cermet, glass, various halogenated hydrocarbons, and any other suitable nonconductors.

As depicted in FIGS. 10h-10j at cross section line 10j-10j, in other embodiments, beads 1051' may not comprise any tunnels or holes, thereby effectively narrowing slot 1080s' and reducing the width of the distal lysing segment 1060d' of electrode 1060'. Lysing tip shaft 1033s' may define the medial boundaries of proximal lysing segments 1060p', as best shown in FIG. 10j.

When an electrosurgical generator is activated by a surgeon, electrosurgical energy may be transmitted through conductive insert 1060s, through shaft 1090, to electrode 1060, which activates lysing segments 1060d and 1060p for delivery of electrosurgical energy into tissue.

In some embodiments, the conductive material of electrode 1060 may comprise: steel, nickel, alloys, palladium, gold, tungsten, silver, copper, platinum and/or another conductive metal that does not give off toxic residua at operating temperatures. In some embodiments, electrode 1060 may be coated with a non-stick material which may comprise gold, silver, rhodium, titanium, titanium alloys, tungsten, certain cobalt alloys and the like, along with combinations of any of the foregoing.

In some embodiments, the width of the distal portion of lysing tip 1033 (defined between the outermost portions of the outermost beads 1051) may be between about 4 mm and about 5 mm and the length of the beads, which may be defined by the shaped nonconductive body 1033b, may be between about 3 and about 10 mm.

By providing both distal and proximal lysing segments for dissection and/or coagulation of tissue in an anterograde and/or retrograde fashion, a number of benefits may be achievable. For example, the efficiency of dissection may be increased because a forward pass may separate tissue and moving the tip in the reverse direction also separates tissue rather than merely readying the tip for another forward pass. As another example, providing both distal and proximal lysing segments, preferably using recessions, may reduce in the necessary width/size of operating tool so various models may fit down smaller diameter cannulas and/or entrance-wounds/body-openings for minimally invasive surgery and/or entrance wound/scar minimization. In addition, providing for retrograde dissection may favor various dissection angles or patterns when various force vectors are placed upon the target tissues and/or target tissue planes.

It should be understood that the embodiments disclosed herein may have value and application in various different types of surgery. For example, the lysing tips, devices, and methods disclosed herein may be useful for cosmetic surgery, including facial dissection, neck dissection, and cellulite treatment, and may also be useful in connection with internal surgeries, such as laparoscopic and/or endoscopic procedures. Thus, the device may be introduced directly into the body from an opening in the skin or may be introduced using a trocar and/or cannula in other types of surgical procedures.

While the device is energized with electrosurgical energy, beads 1051 and strut 1080 are preferably non-conductive in order to perform the blunt dissection function.

In some embodiments, lysing member/electrode assembly 1060 comprises a rigid and/or substantially rigid plate as shown in FIG. 10d. In such embodiments, one or both of proximal lysing segments 1060p and/or distal lysing segments 1060d may be configured to be electrically coupled with electrode shaft 1060s. In some such embodiments, electrode 1060 may comprise a single, unitary piece of a suitable conductive material that serves each of these functions.

In alternative embodiments, any number of holes may be made at any number of angles to intersect the electrode assembly 1060 and/or its tunnel 1051t or slot 1080sd to deposit a material that restrains the lysing segment/electrode assembly within the beads 1051, the bead tunnels 1051t, and/or slot 1080 (for example, materials may include welds, glues, epoxies, plugs, and the like). In such embodiments, tunnel 1051t may be a blind tunnel not requiring full passage through bead 1051. In other embodiments, tunnels 1051t may be complete tunnels. In alternative embodiments, beads 1051 may be replaced with beads of any shape, including but not limited to those depicted in FIGS. 7aa to 7zzz.

As previously mentioned, lysing tip 1033 comprises a plurality of beads 1051 and a plurality of recessed lying segments that, again, may be defined by one or more electrodes. It should be noted that in the embodiments of FIGS. 10a-10g, beads 1051 are supported laterally along their respective inner sides by strut 1080. In other words, beads 1051 each define a primary and/or elongated axis extending between their respective distal tips and proximal tips. In the depicted embodiment, these axes extend at least substantially parallel to the axis of the instrument 1000. Rather than being supported from behind, such as by an element extending between the proximal ends of beads 1051, beads 1051 are support along their respective sides by an element (strut 1080 in the depicted embodiment) that extends at least substantially perpendicular relative to their respective primary axes so that the bead shape is still apparent from the structure of lysing tip 1033.

It should also be noted that beads 1051 lack a base, such as base 105 for system 100 detailed in U.S. patent application Ser. No. 15/464,199 titled "Apparatus, Systems and Methods for Minimally Invasive Dissection of Tissues" filed on Mar. 20, 2017, which application is hereby incorporated by reference in its entirety. Thus, it should also be understood that beads 1051 lack structure immediately behind the beads for support. It should also be noted that lysing tip 1033 comprises beads 1051 that project both distally and proximally relative to strut 1080.

Shaft 1090 may couple with tip 1033 to facilitate transfer of electrosurgical energy in a desired manner and/or allow for manually dissection in the absence of electrosurgical energy. Shaft 1090 may be deformable, that is, it may be bent so as to angle the lysing tip in a desired direction, for example, to ensure the lysing tip is angled up by 3 to 10 degrees so as to direct cutting/lysing towards the dermis of the skin in a cosmetic procedure.

It should also be noted that beads 1051 may, on the same instrument, be of the same shape, may be of different shapes, and/or may be angled up or angled down by, for example, between about 3 to about 15 degrees to assist in guiding the tip towards the upper or lower tissue plane. In other embodiments, each bead may be angled in a different direction as desired in accordance with the anticipated use of the device. In these embodiments, strut 1080 may remain parallel to the top and/or bottom surfaces of the device or may follow the same angle as its respective bead.

Shaped nonconductive body 1033b may comprise one or more sensor openings 1070 and 1070a (only shown on FIGS. 10a and 10c) which may serve as locations for various sensors including but not limited to temperature sensors, fiberoptics, positioning sensors, RFID sensors/tags, and the like. Sensor openings 1070 and 1070a may be connected to one or more ducts that may pass through shaped noncon- ductive body 1033b and exit on the proximal end of lysing tip 1033. Alternatively, sensors positioned in sensor open- ings 1070 and 1070a may be configured to deliver data wirelessly. It should be noted that sensor 1070a is located on the distal end of bead 1051; a sensor located in opening 1070a may be used to measure temperature during the instrument's back stroke because the treated tissue would typically pass adjacent to this sensor 1070a during a back stroke. In some embodiments, a temperature or other sensor measurement may be taken during an RF activation or between RF pulses. In alternative embodiments, the sensor exposed at sensor opening 1070a may be a fiberoptic that may sense tissue color and/or the presence of blood.

While instrument 1000 is energized with electrosurgical energy, beads 1051 and strut 1080 are preferably non- conductive, thus minimizing unwanted electrical discharge. The electrically conductive electrode 1060 may be config- ured to deliver electrosurgical energy through the various distal and/or proximal lysing segments, as previously men- tioned.

Beads 1051 and strut 1080 may be comprised of ceramic, cermet, glass, various halogenated hydrocarbons, and any other suitable nonconductors. Beads 1051 may be restricted in their motion and/or affixed to strut 1080 via direct coupling (i.e., continuous/integral ceramic) and/or conduc- tive materials such as those that comprise electrode 1060. As well, indirect sealing methods such as epoxy or ceramic glues or potting mixes and the like may be used to seal any unwanted seams or openings to maintain non-conductive integrity in the desired locations. When an electrosurgical generator is activated by a surgeon, electrosurgical energy may be transmitted through any suitable electrical coupling elements to electrode 1060.

In still another embodiment depicted in FIGS. 10k-L, at the cross section of Line 10k-10k set forth in FIG. 10i, electrode 1063 may be modified with nonconductive lip 1063L that is intended to be positioned adjacent to the border created by the edges of strut (not shown) and the edges of beads 1053 and bead tunnels 1053t, if present. Nonconductive lip 1063L may then define or substantially define distal lysing segment 1063d. Nonconductive lip 1063L may assist in sealing the internal components from liquid intrusion, minimize the unwanted escape of RF energy, and/or reduce the surface area of lysing segment exposure. Nonconductive lip 1063L may be composed of various materials that adhere to conductors and/or may be a suitable dielectric, for example, a ceramic or porcelain material.

FIGS. 11a-11e depict an embodiment of a lysing instru- ment 1100. Instrument 1100 may comprise shaft 1190 and two-way lysing tip 1133. Lysing tip 1133 is configured for two-way motion (i.e., forward/distal and reverse/proximal motion) due to, as discussed below, the presence of lysing segments that face in the forward/distal direction to facilitate forward motion of lysing tip 1133 through tissue and other lysing segments that face in the rearward/proximal direction to facilitate rearward/proximal motion of lysing tip 1133 through tissue. The rearward/proximal lysing segments of instrument 1100 extend, as shown in the figures, at least substantially perpendicular to the shaft 1190 of instrument 1100. In the depicted embodiment, both the distal and proximal lysing segments define concave curves. However, both of the points at which these lysing segments terminate (at or adjacent to a bead on one end and at or adjacent to shaft 1190 at the opposite end) define a line that is perpen- dicular, or at least substantially perpendicular, to shaft 1190 and/or the primary/elongated axes of the beads themselves. Similarly, at a central or at least substantially a central point along each of the lysing segments between the two termi- nation points previously referenced, a tangent line to this curvature is perpendicular, or at least substantially perpen- dicular, to shaft 1190 and/or the primary/elongated axes of the beads. Thus, despite the curvature of the depicted lysing segments, they should each be considered to extend at least substantially perpendicular to the shaft 1190 of instrument 1100, and at least substantially perpendicular to the elon- gated and/or primary axis of beads 1151. These aspects of the lysing segments may apply to any of the other embodi- ments depicted and/or otherwise disclosed herein.

However, other embodiments are contemplated in which these lysing segments may extend at another angle relative to the shaft 1190 and/or primary axis of instrument 1100. For example, in other embodiments, the proximal/rearward lys- ing segments may extend at an angle of between about 60 degrees and about 120 degrees from the shaft 1190 and/or primary axis of instrument 1100. Shaft 1190 may physically couple lysing tip 1133 to an electrosurgical energy source such as an electrosurgical pencil (not shown) via conductive insert 1160s, which in the depicted embodiment comprises a conductive rod, which may be electrically conductive and act as a conduit for electrosurgical energy to flow to lysing tip 1133. In the depicted embodiment, conductive insert 1160s comprises an integral extension from electrode 1160. In other contemplated embodiments, however, conductive insert 1160s may be coupled to electrode 1160, either directly or indirectly such as by way of a wire or the like.

Lysing tip 1133 comprises one or more distal-facing lysing segments and one or more proximal-facing lysing segments. Each of these various lysing segments may be defined by a single electrode or each by its own respective electrode. In the depicted embodiment, a single electrode 1160 is used to define each of the various lysing segments, including both the distal facing lysing segments that are configured to facilitate forward/distal motion of instrument 1100 and the proximal-facing lysing segments that are configured to facilitate rearward/proximal motion of instru- ment 1100. A non-conductive body 1133b may be used to define various beads, protrusions, and/or other features that define recessions into which the lysing segments are posi- tioned. In some embodiments, the recessions may be defined by beads, struts, and/or lysing segments. Non-conductive body 1133b defines three forward-facing distal protrusions 1101d defined by the distal tips 1151d of beads 1151 and nose 1136 of shaft 1190 and distal recessions 1102d (more than one distal recession may be provided on other embodi- ments) positioned between distal tips of beads 1151d and nose 1136. Lysing tip 1133 may further comprise one or more rearward-facing proximal protrusion/recession pairs as well to facilitate proximal motion of the device 1100 through tissue. For example, beads 1151 further define rearward protrusions defined by the proximal tips 1101p of beads 1151 and recessions 1102p defined by proximal tips 1101p of beads 1151 along with struts 1180.

Shaped nonconductive body 1133b may comprise one or more beads 1151 that may be supported by and/or spaced by one or more rigid or substantially rigid struts 1180, each of which may be permanently or temporarily coupled between adjacent beads 1151 and/or between an outer bead and the nose 1136 and/or shaft 1190 or shaft portion of lysing tip 1133. In some embodiments, struts 1180 may be further coupled along a proximal region with the shaft of lysing tip 1133. In the preferred embodiment shown in FIGS. 11a-11e, shaped nonconductive body 1133b may comprise one or more slots 1180s that may extend along each strut 1180. Slot(s) 1180s may define a distal slot opening 1180sd defined on its upper and lower sides by struts 1180 and/or nose 1136 and on its left and right sides by one or more beads 1151.

In this embodiment, electrode 1160 may be passed through distal slot opening 1180sd and operationally positioned and configured to define distal lysing segments 1160d, which may be defined by exposed portions of electrode 1160 on either side of nose 1136, to face distally through distal slot opening 1180sd and to allow for delivery of electrosurgical energy, or another type of suitable energy for modification of tissue, therethrough. Shaped nonconductive body 1133b may further comprise one or more proximal slot openings 1180sp through which proximal lysing segments 1160p of electrode 1160 may be exposed to allow for delivery of electrosurgical energy therethrough and to facilitate rearward/proximal movement of lysing tip 1133 through tissue.

In the depicted embodiment, specifically FIG. 11c, an exploded view shows how electrode 1160 may be inserted into distal slot 1180sd which may also receive nose 1136 therein, which may be bonded or otherwise fixed in place to finalize the assembly.

In other embodiments such as in FIG. 11f, the nose defining the center protrusion may be manufactured to receive a nose insert 1136' therein, which may be coupled in place via a coupling agent such as a ceramic glue, fastener, or the like. In still other embodiments, nose insert 1136' (the volume between the upper portion of the nose and the lower portion of the nose) may be filled with a filling agent, such as a high temperature epoxy or the like.

Shaped nonconductive body 1133b may comprise one or more sensor openings 1170a, 1170b, and 1170c (shown only in FIG. 11b) which may serve as locations for various sensors including but not limited to temperature sensors, fiberoptics, positioning sensors, RFID sensors/tags, and the like. Sensor openings 1170a, 1170b, and 1170c may be connected to one or more ducts that may pass through shaped nonconductive body 1133b and exit on the proximal end of lysing tip 1133. Alternatively, sensors positioned in said sensor openings may be configured to deliver data wirelessly. It should be noted that sensor opening 1070b may be located on the distal end of bead 1151. In addition, a sensor may be located in nose sensor opening 1170c. Sensors located in openings 1170b and 1170c may be used to measure temperature during the instrument's back stroke. In some embodiments, said measurement may be taken during an RF pulse or between RF pulses. In alternative embodiments, the sensor exposed at any sensor opening may be a fiberoptic that may sense tissue color and the presence of blood.

Beads 1151, nose 1136, and/or strut 1180 may be comprised of ceramic, cermet, glass, various halogenated hydrocarbons, and any other suitable nonconductors.

As depicted in FIGS. 11g-11h, in other embodiments, beads 1151' may not comprise any tunnels or holes 1151t, thereby effectively narrowing the required length of slot(s) 1180s' and reducing the corresponding width of the distal lysing segments 1160d' of electrode 1160' exposed by slot(s) 1180s'. Lysing tip shaft 1133s' may define the medial boundaries of proximal lysing segments 1160p', as shown in FIG. 11h.

When an electrosurgical generator is activated by a surgeon, electrosurgical energy may be transmitted through conductive insert 1160s, through shaft 1190, to electrode 1160, which activates lysing segments 1160d and 1160p for delivery of electrosurgical energy into tissue.

In some embodiments, the width of the distal portion of lysing tip 1133 (defined between the outermost portions of the outermost beads 1151) may be between about 6 mm and about 12 mm and the length of the beads, which may be defined by the shaped nonconductive body 1133b, may be between about 3 and about 10 mm.

It should be noted that in being able to dissect in forward and backward directions, lysing tips 1033 and 1133 uniquely may be more efficient than single direction lysing tips. Retrograde dissection may also facilitate use of alternative tissue tension force vectors adjacent to the target tissues and/or target tissue planes. Tissue tension force vectors may be applied by surgical assistants and/or the surgeon's non-instrument hand. As well, retrograde dissection may allow for alternative dissection angles.

While the device is energized with electrosurgical energy, beads 1151, nose 1136, and strut 1180 are preferably nonconductive in order to perform the blunt dissection function. However, in some embodiments, one or more of these elements may comprise a conductive core and a nonconductive coating or shell.

In some embodiments, lysing member/electrode assembly 1160 comprises a rigid and/or substantially rigid plate as shown in FIG. 11c. In such embodiments, one or both of proximal lysing segments 1160p and/or distal lysing segments 1160d may be configured to be electrically coupled with electrode shaft 1160s. In some such embodiments, electrode 1160 may comprise a single, unitary piece of a suitable conductive material that serves each of these functions. Slot 1180sd may be configured so as to tightly receive lysing member electrode assembly 1160 so as to prevent or at least inhibit movement or unwanted RF energy escape. As previously mentioned, lysing tip 1133 may comprise a plurality of beads 1151 and a plurality of recessed lysing segments that, again, may be defined by one or more electrodes. It should be noted that in the embodiments of FIGS. 11a-11h, beads 1151 are supported laterally along their respective inner sides by strut 1180. It should also be noted that beads 1151 lack a base, such as base 105 for system 100 detailed in U.S. patent application Ser. No. 15/464,199 titled "Apparatus, Systems and Methods for Minimally Invasive Dissection of Tissues" filed on Mar. 20, 2017, which application is hereby incorporated by reference in its entirety. Thus, it should also be understood that beads 1151 lack structure immediately behind the beads for support. It should also be noted that lysing tip 1133 comprises beads 1151 that project both distally and proximally relative to strut 1180.

Shaft 1190 may couple with tip 1133 to facilitate transfer of electrosurgical energy in a desired manner and/or allow for manually dissection in the absence of electrosurgical energy. Shaft 1190 may be deformable, that is, it may be bent so as to angle the lysing tip in a desired direction, for example, to ensure the lysing tip is angled up by 3 to 10 degrees so as to direct cutting/lysing towards the skin in a cosmetic procedure.

While system 1100 is energized with electrosurgical energy, beads 1151 and strut 1180, or at least a portion thereof (such as surfaces other than those exposed for defining/exposing lysing segments), are preferably nonconductive, thus minimizing unwanted electrical discharge. The electrically conductive electrode 1160 may be configured to deliver electrosurgical energy through the various distal and/or proximal lysing segments, as previously mentioned.

In some embodiments, the conductive material of electrode 1160 may comprise: steel, nickel, alloys, palladium, gold, tungsten, silver, copper, platinum and/or another conductive metal that preferably does not give off toxic residua at typical operating temperatures. In some embodiments, electrode 1160 may be coated with a non-stick material which may include gold, silver, rhodium, titanium, titanium alloys, tungsten, certain cobalt alloys and the like.

Beads 1151, nose 1136, and strut 1180 may be comprised of ceramic, cermet, glass, various halogenated hydrocarbons, and any other suitable nonconductors. Beads 1151 may be restricted in their motion and/or affixed to strut 1180 via direct coupling (i.e., continuous/integral ceramic) and/or conductive materials such as those that comprise electrode 1160. As well, indirect sealing methods such as epoxy or ceramic glues or potting mixes and the like may be used to seal any unwanted seams or openings to maintain nonconductive integrity in the desired locations. When an electrosurgical generator is activated by a surgeon, electrosurgical energy may be transmitted through any suitable electrical coupling elements to electrode 1160.

It should also be noted that beads 1151, on the same instrument, may be of the same shape, may be of different shapes, and/or may be angled/tilted up or angled/tilted down by between about 3 to about 15 degrees to assist in guiding the tip towards the upper or lower tissue plane. In other embodiments, each bead may be angled in a different direction. In some embodiments, strut 1080 may remain parallel to the upper and/or lower surfaces of the device or strut 1080 may follow the same angle as its respective tilted bead such as that of bead 1154 coupled with bent/angled shaft 1134 depicted in FIG. 11*i*.

In another embodiment, lysing tip 1133 may be configured to oscillate in various planes which may assist in reducing eschar buildup and may aid in the movement of lysing tip 1133 through tissues with mechanical energy. In this embodiment, shaft 1190 may comprise a piezoelectric or oscillating/vibrating motor unit 1199, which may be placed in the handle or at another point between the handle and the distal tip wherein the necessary harmonic motion is created. High energy frequencies, like in the ultrasound regions, may be chosen but may be too powerful for a multi-component device. However, lower frequencies with lower energy, similar to those used in toothbrushes to aid in cleaning, may provide the necessary energy to reduce eschar and assist in lysing. Lower frequencies may be possible by use of a voice coil, however, piezoceramics may be preferred. Higher frequency in the ultrasound range requires a smaller piezo. Said frequency range may be from about 1 kHz to about 80 kHz, with a preference for between about 21 to about 40 kHz. A hard-ceramic type piezoceramic motor may be preferred, and for lower excursion, the type could be expanded to include Navy Type I, exemplified by APC 840.

FIG. 12 and FIGS. 13*a*-*c* depict a 2-bead lysing instrument 1200 and a 3-bead lysing instrument 1300, respectively. Instruments 1200 and 1300 both comprise a lysing tip 1233/1333, respectively.

Lysing tip 1233 comprises a conductive, unibody core 1260 (shown in FIG. 12 at the cut-away window through the nonconductive layer), which may comprise a suitable metal or other preferably conductive material. Conductive core 1260 may comprise a unitary shape that forms the structure(s) depicted in the drawings, namely, opposing beads 1250, strut 1280, a distal recess through which a lysing segment may extend, as discussed below, and two proximal recesses through which two corresponding lysing segments may extend. As a finished product, each of the surfaces of lysing instrument 1200 other than these lysing segments may be coated, layered, or otherwise configured to avoid delivering energy, electrosurgical or otherwise, therefrom. Thus, in some embodiments, lysing tip 1233 may be coated with a suitable non-conductive material, such as high melting point polymers, ceramics, and/or glass. Examples of ceramic coatings may include those from MetaCeram® that may be tailored for a particular use and employ such raw materials as high purity chromium oxides, alumina-zirconia composites, and/or blends of aluminum oxide and titanium oxide. Examples of suitable glass coatings may include Porcelain enamels (frits), "art" glass frits, commercial frits, and frits used in dental applications. Glass coating may be employed with application by: dip coating, spray, electrostatic application and sifting. Application may be followed by a curing firing to vitrify the glass. In alternative implementations, PVD may also be used, in which case no further vitrification may be required.

In certain implementations of methods of manufacture, conductive core 1260 of lysing tip 1233 may be entirely coated with any of the aforementioned materials or another suitable material to form a shell 1256 to prevent or at least inhibit transfer of electrosurgical or other energy from the conductive core 1260 to adjacent tissue during a surgical procedure. After this coating has been applied, the coating/shell 1256 may be selectively removed from certain areas, such as regions within the distal and proximal recesses of instrument 1200 defining the desired lysing segments 1260*d* and 1260*p*, by way of etching or another suitable process. In other implementations, the desired lysing segments may be established by masking these regions before the coating/layer(s) is applied to conductive core 1260 so that no etching/removal of shell 1256 is required.

In some embodiments and implementations, the areas defining the lysing segments may further be sharpened or otherwise formed with shapes configured to facilitate desired delivery of energy therethrough and/or dissect tissue without application of energy. This sharpening may be accomplished in the same step as etching the non-conductive shell 1256 or in an independent step.

In FIG. 12, conductive unibody form 1233 comprises structural features similar to embodiments previously described herein, however, these features/elements are preferably indefeasibly coupled as one unitary formed body. Distal protrusions 1201*d* and distal recesses 1202*d* may be substantially defined by a plurality of distal tips 1250*d* of beads 1250, distal lysing element 1260*d*, and/or the front edge of strut 1280. Proximal protrusions 1201*p* and recesses 1202*p* may be defined by proximal tips 1250*p* of beads 1250, proximal lysing elements 1260*p*, and/or the back edge of strut 1280. As previously mentioned, conductive distal lysing segment 1260*d* and conductive proximal lysing segments 1260*p* are exposed to facilitate delivery of energy therethrough.

As depicted in FIGS. 13*a*-*c*, lysing tip 1333 comprises a conductive, unibody core 1360, which may comprise a suitable metal or other preferably conductive material. Conductive core 1360 may comprise a unitary shape that forms the structure(s) depicted in the drawings, namely, opposing beads 1350, struts 1380, and shaft extension/nose 1336.

Beads 1350 define forward and rearward-facing protrusions and partially define corresponding forward and rearward-facing recesses through which corresponding lysing segments may extend, as previously discussed. As a finished product, each of the surfaces of lysing instrument 1300 other than these lysing segments (i.e., distal-facing lysing segments 1360d and proximal-facing lysing segments 1360p) may be coated, layered, or otherwise configured to avoid delivering energy, electrosurgical or otherwise, therefrom. Thus, in some embodiments, lysing tip 1333 may be coated with a suitable non-conductive material, such as those listed for the embodiment depicted in FIG. 12.

As best depicted in FIG. 13c, in certain implementations of methods of manufacture, conductive core 1360 of lysing tip 1333 may be entirely coated or otherwise applied with any of the aforementioned materials or another suitable material to form a coating and/or shell 1356 to prevent or at least inhibit transfer of electrosurgical or other energy from the conductive core 1360 to adjacent tissue during a surgical procedure. After this coating has been applied, the coating/shell 1356 may be selectively removed from certain areas, such as regions within the distal and proximal recesses of instrument 1300 defining the desired lysing segments 1360d and 1360p, by way of etching or another suitable process. In other implementations, the desired lysing segments may be established by masking these regions before the coating/layer(s) is applied to conductive core 1360 so that no etching/removal of shell 1356 is required.

In FIG. 13a, conductive unibody form 1333 comprises structural features similar to embodiments previously described herein, however, these features/elements are preferably indefeasibly coupled as one unitary formed body. Distal protrusions 1301d and distal recesses 1302d may be substantially defined by a plurality of distal tips 1350d of beads 1350, distal lysing segments 1360d, and/or the front edges of strut 1380. Proximal protrusions 1301p and recesses 1302p may be defined by proximal tips 1350p of beads 1350, proximal lysing elements 1360p, and/or the back edge of strut 1380. As previously mentioned, conductive distal lysing segment 1360d and conductive proximal lysing segments 1360p are exposed to facilitate delivery of energy therethrough.

These coating/etching/shell principles may be applied to any of the other embodiments disclosed herein, or to other embodiments available to those of ordinary skill in the art after having received the benefit of this disclosure, such as embodiments having different numbers of beads, distal protrusions, distal recesses and/or lysing segments, proximal protrusions, and/or proximal recesses and/or lysing segments.

In some embodiments, such as that depicted in FIGS. 14a-d, the lysing tip 1433 of a lysing tip system similar to those already disclosed herein may have the angle of attack of its cutting surfaces modified with a means for pressing a portion of a control instrument and/or lysing tip against a tissue to direct the lysing tip towards a desired treatment tissue in a direction normal or at least substantially normal to an axis of the control instrument, such as deflection system 1400. Deflection system 1400 may be used for pressing a portion of a control instrument and/or lysing tip against a tissue to direct the lysing tip towards a desired treatment tissue, such as in the depicted embodiment in a direction normal or at least substantially normal to an axis of the control instrument. In other embodiments, it is contemplated that deflection system 1400 may be configured to deflect or otherwise move the lysing tip away from or towards a particular tissue and/or treatment area without necessarily doing so in a direction normal to the axis of the instrument. Longer cannulas may tend to be less controllable for treatment zones that are distant from the entrance wound. Thus, one or more deflection legs 1490L or other suitable deflection means may be useful, especially in cosmetic procedures, such as cellulite treatment, in order to force the lysing tip 1433 more superficially against the lower dermis, for example. The presence of the deployed deflection legs 1490L may facilitate surgery in more distal locations from the entrance wound. In the depicted embodiment, four bow-like, segments, deflection legs 1490L may be present on the distal to mid-distal portions of the device shaft and be deployable individually or as a group.

More specifically, deflection legs 1490L may be part of a deflection sleeve 1490, which may comprise one or more slidable deployment members 1490a, each of which may be coupled to one or more deflection legs 1490L. In the depicted embodiment, an upper deployment member 1490a is coupled to two upper deflection legs 1490L and a lower deployment member 1490a is coupled to two lower deflection legs 1490L. In this manner, a surgical instrument used with deflection system 1400 may be configured for being deflected in either direction (or, in other embodiments, any number of more precise directions according to the number of deflection legs 1490L and/or deployment members 1490a) depending upon which of the deployment members 1490a is actuated. Thus, as shown in FIG. 14d, upon advancement of the upper deployment member 1490a, which in the depicted embodiment defines a cylindrical surface configured to extend over (or inside of) a similarly-shaped instrument shaft, the upper two deflection legs 1490L bow outward in order to provide a deflection force, as described above.

In the depicted embodiment, it will be assumed that base lysing device is similar to one previously disclosed (e.g., 1090 and 1190) wherein a lysing tip 1433 is supported and driven by proximal shaft that leads to an energy supply. Deflection system 1400 comprises outer sheath 1495, which may comprise slots 1495s configured to allow deflection legs 1490L to extend/bow therethrough, and deflector sleeve 1490. Deflector sleeve 1490 may comprise collar 1490c, deflector legs 1490L, and deployment member(s) 1490a, which may comprise holes 1490h that may be coupled with a suitable handle and/or control for separately actuating each of the various deployment members 1490a. Collar 1490c effectively couples the deflector sleeve 1490 to the device shaft. Again, deployment members 1490a each couple to a separate leg 1490L and when pushed distally or pulled proximally the proper distance, deploy or retract the leg 1490L to which it is coupled, respectively. Outer sheath 1495 comprises slits 1495s through which the deflector legs 1490L may also hold deployment members 1490a in place for operation.

Deflection legs 1490L may vary in number as desired in accordance with preferred functionality, such as from 1 to 10 on a given assembly. Deflection legs 1490L may be comprised of silicone, rubber, plastic, halogenated hydrocarbon, silastic, nylon, vinyl, polycarbonate, and the like. Deflection legs 1490L may also be comprised of stainless steel, in preferred embodiments approximately 0.1 mm thick. In some embodiments, the shape of deflection legs 1490L may comprise a slightly bent shape in the relaxed state so that when manipulated with a compression force to extend the legs, the relaxed shape will permit efficient extension. In other embodiments, the shape of the deflection legs 1490L may be fully extended in the relaxed state and may be retracted with a withdrawal force from deployment members 1490*a*.

FIGS. 15*a*-15*d* depict an embodiment of a bipolar lysing instrument 1500. Instrument 1500 may comprise shaft 1590 and two-way lysing tip 1533. Lysing tip 1533 is configured for two-way motion (i.e., forward/distal and reverse/proximal motion) due to, as discussed above, the presence of lysing segments that face in the forward/distal direction to facilitate forward motion of lysing tip 1533 through tissue and other lysing segments that face in the rearward/proximal direction to facilitate rearward/proximal motion of lysing tip 1533 through tissue.

In contrast to the previous similar embodiments that may be monopolar, instrument 1500 is bipolar and is comprised of two isolated electrodes, each of opposite and alternating polarity, namely, electrodes 1560*p* and 1560*n*. Electrodes 1560*p* and 1560*n* may define distal lysing segments 1560*pd* and 1560*nd*, respectively, and may define proximal lysing segments 1560*pp* and 1560*np*, respectively. Shaft 1590 may physically couple lysing tip 1533 to an electrosurgical energy source via proximal shafts of electrodes 1560*p* and 1560*n*, respectively, which, in the depicted embodiment comprises a conductive rod, which may be electrically conductive and act as a conduit for electrosurgical energy to flow to/from lysing tip 1533. In the depicted embodiment, proximal shafts of electrodes 1560*p* and 1560*n* comprise an integral extension from their corresponding electrode portions that extend into or are otherwise coupled with beads 1501. Of course, in alternative embodiments, wires 1561*p* and 1561*n*, or another suitable means for electrical coupling, may instead extend all the way to the portions of their corresponding electrodes that are within lysing lip 1533.

The rearward/proximal lysing segments of instrument 1500 extend, as shown in the figures, at least substantially perpendicular to the shaft 1590 of instrument 1500 as previously described in connection with FIGS. 11*a*-11*e*.

Lysing tip 1533 comprises one or more distal-facing lysing segments and one or more proximal-facing lysing segments. The lysing segments, both proximal and distal-facing, on one side of lysing tip 1533 may be defined by a single electrode or each by its own respective electrode. Thus, in the depicted embodiment, a single positive electrode 1560*p* is used to define the distal-facing lysing segment 1560*pd* and the proximal-facing lysing segment 1560*pp* on the right half of lysing tip 1533. Similarly, a single negative electrode 1560*n* is used to define the distal-facing lysing segment 1560*nd* and the proximal-facing lysing segment 1560*np* on the left half of lysing tip 1533. Again, separate positive and negative electrodes may be used to separately define the distal and proximal facing lysing segments instead if desired.

A non-conductive body 1533*b* may be used to define various beads, protrusions, and/or other features that define recesses into which the lysing segments are positioned and/or extend. In some embodiments, the recesses may be defined by beads, struts, and/or lysing segments, as previously described. Non-conductive body 1533*b* defines three forward-facing distal protrusions 1501*d* defined by the distal tips 1551*d* of beads 1551 and nose 1536 of shaft 1590 and/or partly by distal recesses 1502*d* (more than two distal recesses may be provided in other embodiments) positioned between distal tips of beads 1551*d* and nose 1536. Non-conductive body 1533*b* defines three rearward-facing proximal protrusions 1501*p* defined by the proximal tips of beads 1551 and shaft 1590 and/or partly by proximal recesses

1502*p* (more than two distal recesses may be provided in other embodiments) positioned between distal tips of beads 1551*d* and nose 1536.

Lysing tip 1533 and/or shaft 1590 may further comprise an insulating barrier 1554, which may be positioned in between positive electrode(s) 1560*p* and negative electrode(s) 1560*n* so as to keep these electrodes electrically isolated, or at least substantially electrically isolated, from each other. Insulating barrier 1554 preferably comprises a suitable electrically non-conductive material, such as an electrically nonconductive polymer, preferably with relatively high melting temperature, such as greater than about 300 degrees F. In some embodiments, the nonconductive polymer may comprise for example, polytetrafluoroethylene, polyether etherketone, polysulfone, or the like. In other contemplated embodiments, this material may comprise an electrically nonconductive and/or thermally nonconductive polymer. In still other embodiments, a ceramic material may be used to serve as an insulating barrier. For example, in some embodiments, insulting barrier 1554 may comprise a part (in some such embodiments, an integral part) of the non-conductive body 1533*b*.

Although a nose 1536 is present in the depicted embodiment, an example of which was also discussed and depicted previously, it should be understood that, in other embodiments, barrier 1554 may extend all the way to the tip of the center portion of lysing tip 1533, which in the depicted embodiment comprises nose 1536.

Shaped nonconductive body 1533*b* may comprise one or more beads 1551 that may be supported by and/or spaced by one or more rigid or substantially rigid struts 1580, each of which may be permanently or temporarily coupled between adjacent beads 1551 and/or between an outer bead and the nose 1536 and/or shaft 1590 or shaft portion of lysing tip 1533. In some embodiments, struts 1580 may be further coupled along a proximal region with the shaft of lysing tip 1533. In the preferred embodiment shown in FIGS. 15*a*-15*d*, shaped nonconductive body 1533*b* may comprise one or more slots that may extend along each strut 1580 to allow for exposure and/or positioning of electrodes/lysing segments therein. As previously mentioned, in some embodiments, slot(s) 1580*s* may define a distal slot opening defined on its upper and lower sides by struts 1580 and/or nose 1536 and on its left and right sides by one or more beads 1551.

In this embodiment, electrodes 1560*p* and 1560*n* may be passed through a distal slot opening formed in nose 1536 and/or struts 1580 and positioned and configured to define respective positive and negative distal lysing segments 1560*nd*, which may be defined by exposed portions of electrodes 1560*p* and 1560*n* on either side of nose 1536, to face distally through slots 1580*s* and allow for delivery of electrosurgical energy, or another type of suitable energy, for modification of tissue, therethrough. Shaped nonconductive body 1533*b* may further comprise one or more similar proximal slot openings 1580*sp* through which proximal lysing segments 1560*n/p-p* of electrodes 1560*p* and 1560*n* may be exposed to allow for delivery of electrosurgical energy therethrough and to facilitate rearward/proximal movement of lysing tip 1533 through tissue, as previously explained in greater detail.

In some embodiments the nose 1536 defining the center protrusion may be manufactured to receive a nose insert 1536 therein, which may be coupled in place via a coupling agent such as a ceramic glue, fastener, or the like.

Beads 1551, nose 1536, and/or strut 1580 may be comprised of ceramic, cermet, glass, various halogenated hydrocarbons, and any other suitable nonconductors.

As previously mentioned, in some embodiments, beads 1551 may comprise slots, holes, or tunnels for partially receiving electrodes 1560p and 1560n therein. In other embodiments, beads 1551 may not comprise any tunnels or holes, as also previously mentioned.

When an electrosurgical generator is activated by a surgeon, electrosurgical energy may be transmitted through wires 1561p and 1561n, or another suitable conductive member, to electrodes 1560p and 1560n, which activates lysing segments 1560d and 1560p for delivery of bipolar electrosurgical energy into tissue.

In some embodiments, the width of the distal portion of lysing tip 1533 (defined between the outermost portions of the outermost beads 1551) may be between about 6 mm and about 12 mm and the length of the beads, which may be defined by the shaped nonconductive body 1533b, may be between about 3 and about 10 mm.

Retrograde dissection may also facilitate use of alternative tissue tension force vectors adjacent to the target tissues and/or target tissue planes. Tissue tension force vectors may be applied by surgical assistants and/or the surgeon's non-instrument hand. As well, retrograde dissection may allow for alternative dissection angles.

While the device is energized with electrosurgical energy, beads 1551, nose 1536, and strut 1580 are preferably non-conductive in order to perform the blunt dissection function. However, in some embodiments, one or more of these elements may comprise a conductive core and a non-conductive coating or shell.

In some embodiments, electrodes 1560p and/or 1506n may comprise a rigid or at least substantially rigid plate, as shown in FIG. 15c. In some such embodiments, electrodes 1560p and/or 1560n may comprise a single, unitary piece of a suitable conductive material that serves each of the aforementioned functions. Slots 1580s and/or tunnels in beads 1551 may be configured so as to tightly receive the respective electrodes therein so as to prevent or at least inhibit movement or unwanted RF energy escape. As previously mentioned, lysing tip 1533 may comprise a plurality of beads 1551 and a plurality of recessed lying segments that, again, may be defined by one or more electrodes. It should be noted that in the embodiments of FIGS. 15a-15d, beads 1551 are supported laterally along their respective inner sides by struts 1580. It should also be noted that beads 1551 lack a base, such as base 105 for system 100 detailed in U.S. patent application Ser. No. 15/464,199 titled "Apparatus, Systems and Methods for Minimally Invasive Dissection of Tissues" filed on Mar. 20, 2017, which application is hereby incorporated by reference in its entirety. Thus, it should also be understood that beads 1551 lack structure immediately behind the beads, or along the rear ends of beads 1551, for support. It should also be noted that lysing tip 1533 comprises beads 1551 that have opposing tips that project both distally and proximally relative to struts 1580.

Shaft 1590 may couple with tip 1533 to facilitate transfer of electrosurgical energy in a desired manner and/or allow for manual dissection in the absence of electrosurgical energy. Shaft 1590 or shaft of tip 1533 may be deformable, that is, it may be bent so as to angle the lysing tip in a desired direction, for example, to ensure the lysing tip is angled up by 3 to 10 degrees so as to direct cutting/lysing towards the skin in a cosmetic procedure.

While lysing tip 1533 is energized with electrosurgical energy, beads 1551 and strut 1580, or at least a portion thereof (such as surfaces other than those exposed for defining/exposing lysing segments), are preferably non-conductive, thus minimizing unwanted electrical discharge.

The electrically conductive electrode 1560 may be configured to deliver electrosurgical energy through the various distal and/or proximal lysing segments, as previously mentioned.

Beads 1551, nose 1536, and strut 1580 may therefore be comprised of ceramic, cermet, glass, various halogenated hydrocarbons, and any other suitable nonconductors. Beads 1551 may be restricted in their motion and/or affixed to struts 1580 via direct coupling (i.e., continuous/integral ceramic) and/or conductive materials such as those that make up electrodes 1560p and 1560n. Other sealing methods, such as epoxy or ceramic glues or potting mixes and the like may be used to seal any unwanted seams or openings to maintain non-conductive integrity in the desired locations. When an electrosurgical generator is activated by a surgeon, electrosurgical energy may be transmitted through any suitable electrical coupling elements to electrode 1560.

As previously mentioned, two or more sets of electrodes of bipolar instrument 1500 may be of opposite polarity and electrically isolated from each other along their paths. This may require that the entire housing and core components of the instrument be made of a ceramic or other non-conductor with perhaps the use of wire leads that would be electrically isolated from each other and separately coupled to respective electrodes or electrode sets.

FIGS. 16a-f depict a TMT system 1600 comprising a tissue modification tip (TMT) 1610 that may couple to main shaft 1690 that may connect to a power source, such as an electrosurgical energy source. TMT 1610 may comprise nonconductive housing 1633 and one or more tissue modification arms 1611. Tissue modification arm 1611 may be configured to be positioned/deployed in various positions relative to nonconductive housing 1633. For example, FIG. 16c depicts a deployed position/configuration, FIGS. 16d and 16e depict a retracted position/configuration, and an intermediate position is depicted in FIG. 16b. Once deployed, tissue modification arm 1611 may be rotated to a treatment configuration, as generally depicted in the exploded view of FIG. 16f.

Modification arm 1611 may comprise nonconductive arm body 1611b, within which one or more electrodes may be positioned. For example, in some embodiments, a single electrode may be positioned within nonconductive body 1611b, which electrode (or, in other embodiments, a plurality of electrodes) may define one or more electrode termini 1664, which termini may protrude from and/or be exposed by openings formed in nonconductive body 1611b. In some embodiments, a nonconductive mound 1611m may be positioned about these openings for exposure of electrode termini 1664.

Modification arm 1611 may further comprise guide member 1612, which may serve to fix the position of arm 1611b relative to housing 1633 in a deployed position. Guide member 1612 may comprise a protrusion from body 1611b and may further comprise a flattened surface on one side that may be configured to slide against the outer surface of housing 1633 adjacent to slide slot 1614. In this manner, guide member 1612, in combination with slide slot 1614, may be configured to prevent rotation/pivoting of arm 1613, or at least inhibit such rotation beyond a predetermined range.

Housing 1633 comprises axial shaft-slot 1615 and lateral slide-slot 1614. Shaft-slot 1615 may run the length of housing 1633, or at least a suitable length along the distal end of housing 1633, thereby permitting positioning arm 1613 to pass through by advancing arm 1613 axially and may further be configured to facilitate coupling of one or more electrodes defining electrode termini 1664 with an energy conduit and/or source proximal to TMT 1610. Positioning arm 1613 may further comprise knob 1613*a*, which may be positioned and configured to pivotably couple with an opening 1611*h* formed in modification arm 1611. Preferably, this coupling also provides an electrical or other energy coupling that allows for delivery of electrosurgical energy or other energy to electrode termini 1614.

During use, a surgeon may use digital manipulation to rotate arm 1611 after it has been advanced axially through slot 1615. Slide-slot 1614 may then serve as a guide to position and reversibly fix modification arm 1611 during its deployment and, in some embodiments, at intermediate positions. During a reverse/retraction motion by a surgeon, arm 1613 may retract and contact the proximal portion of slot 1614, which may serve to pivot arm 1611 to turn its tip more axially and ultimately with sufficient force, return arm 1613 to its axial configuration. However, by the interaction of the outer portions of slide-slot 1614 and guide 1612, modification arm 1611 may remain relatively fixed, or at least fixed within a particular desired range of motion, during a backstroke of the instrument.

In alternative embodiments, termini 1664 may be configured to be positioned on the bottom of arm 1611, either in addition to or as an alternative to the position of termini 1664 depicted in the figures. However, in various implementations, a surgeon may simply invert the tip of a top-mounted set of termini 1664 so that the termini point in the opposite direction (for example, away from the surface skin and toward the subcutaneous tissues). This inward/subcutaneous direction of energy may be useful in directing energy toward the subcutaneous deposits in cellulite and other cosmetic and surgically modifiable conditions.

Electrode termini may receive energy from an energy source via conduits (not shown) that may comprise, for example, wires and/or fiber optic filaments and/or the like. Termini 1664 may be configured in any manner to accommodate any energy modality, including, but not limited to, laser, intense pulse light, resistive heating, radiant heat, thermochromic, ultrasound, mechanical, and/or microwave.

FIGS. 17*a*-17*e* depict yet another embodiment of a lysing instrument 1700 comprising a lysing tip 1733 having a plurality of beads 1751 and a plurality of lysing segments. Although only distal lysing segments are depicted in the accompanying drawings, it should be understood that alternative embodiments are contemplated in which proximal/rearward lysing segments may also, or alternatively to the distal lysing segments, be included. The lysing segments may be defined by two electrodes, namely, a first electrode 1760*a* that extends through a lumen or other opening formed in shaft 1790 and bends to the right side of the instrument 1700 (from the perspective of the surgeon) and a second electrode 1760*b* that extends through a lumen or other opening (could be the same or a different lumen/opening as the first electrode) formed in shaft 1790 and bends to the left side of the instrument 1700. Thus, one electrode 1760 forms two lysing segments on the right side of lysing tip 1733 (one between a first outermost bead and an adjacent bead and another between the adjacent bead and the nose/tip 1701*n* of the lysing tip and/or shaft 1790) and another electrode forms another two lysing segments on the opposite side of the device. However, it should be understood that, in other contemplated embodiments, a single electrode may form each of the four lysing segments of lysing tip 1733 or, alternatively, four separate electrodes may be used to form each of the four lysing segments.

Lysing tip 1733 may further comprise one or more struts for separating the beads and/or facilitating definition and/or exposure of the various lysing segments. For example, in the depicted embodiment, strut 1780 extends through openings and/or holes formed in each of the various beads to provide spacing between the beads and define recesses between adjacent beads and/or bead-like structures, such as the distal nose/tip 1701*n*. Of course, separate struts may be used to define these features and/or provide this spacing if desired. Strut(s) 1780 may comprise an elongated slot along its distal edge and/or surface to as to allow for exposure of one or more electrodes 1760*a/b* therein so as to define lysing segments along the distal portion of lysing tip 1733. Electrode(s) 1760*a/b* may protrude from this slot or may be recessed within the slot, depending upon the desired lysing characteristics of the device and the type of energy used. As previously mentioned, in other embodiments, a similar slot may be formed along the rear portion of the strut(s) 1780 so as to provide for rearward lysing if desired.

In the embodiment of FIGS. 17*d* and 17*e*, one or more of the beads 1751*a* may further comprise spacing 1751*ao*, which may be provided by increasing the diameter of the opening/tunnel through which electrode(s) 1760 and/or strut(s) 1780 extend or, in other embodiments, by forming hollow regions and/or cutouts adjacent to the lysing segments and/or struts. This added spacing may provide one or more desired functions, such as allowing the electrode(s) 1760*a/b* to cool. Such spacing may also accommodate/facilitate cleaning of the device, provide more cutting efficiency, assist in determining whether the device has been used previously, particularly for devices intended for single use, may allow for electrical discharge to take place within the hollow area/spacing, and/or may provide for greater cutting and/or electrosurgical discharge surface area.

However, as shown in FIG. 17*a*, this spacing may be omitted in other embodiments and the opening/tunnel for receiving the strut(s) and/or electrode(s) may be relatively tight so as to not accommodate any appreciable spacing adjacent thereto.

As best shown in FIGS. 17*a* and 17*d*, beads 1751/1751*a* may be somewhat flattened, which may provide sufficient rigidity while still exposing the lysing segments to sufficient tissue as the device passes by. This shape of bead may further facilitate guidance of the beads through tissue.

In other embodiments, the basic shape of FIG. 17*a-d* may be formed with all of its components/features as one unibody piece from a suitable conductive material to which an outer shell of relatively non-conductive material is added to prevent energy discharge except for where the lysing segments are exposed by the removal of the outer shell. This concept is similar to that depicted and described in FIGS. 12 and 13*a-c*.

FIGS. 18*a* and 18*b* depict an alternative embodiment of a lysing tip 1833 of a lysing instrument. In this embodiment, the rear portion of the lysing tip 1833 comprises rearward-facing lysing segments 1860*r* that are configured to facilitate backwards/proximal motion of the lysing tip 1833 through tissue. However, unlike the embodiments depicted in previous figures, lysing tip 1833 comprises rearward-facing lysing segments 1860*r* that are not positioned within and/or extended from recesses formed along the rear portion of the lysing tip 1833. Lysing segments 1860*r* may be slightly recessed within slits formed along the rear surface of lysing tip 1833 or, alternatively, may protrude slightly from such slits or other suitable openings formed in the non-conductive body of the lysing tip 1833.

Although this embodiment may be less preferred for certain applications, due to the lack of recesses along the rear portion, which, may contribute to the efficacy of the maneuverability or other desired aspects of the functionality of the lysing tip during proximal movement through tissue, it may be suitable for certain applications.

The front portion of lysing tip 1833 may be similar to the embodiments previously discussed. For example, lysing segments 1860f, which, again, may be defined by individual electrodes or a single electrode positioned within the body of the device, are positioned within concave recesses defined by adjacent protrusions 1801d along the front of lysing tip 1833. Lysing tip 1833 may be coupled and/or integrated with a lysing instrument in any suitable manner, including those discussed in connection with other embodiments disclosed herein.

FIGS. 19a and 19b depict yet another alternative embodiment of a lysing tip 1933. In this embodiment, the basic shape of the lysing tip 1933 is reversed relative to lysing tip 1833. In other words, the front, distal-facing portion of the lysing tip 1933 lacks recesses but, instead, provides lysing segments 1960f that extend along two portions of a relatively flat front surface of the lysing tip 1933. As with lysing tip 1833, lysing tip 1933 may comprise lysing segments 1960f that either protrude slightly from or are recessed within slits or other openings formed in the non-conductive body of lysing tip 1933.

Along the rear portion of lysing tip 1933, similar lysing segments 1960r may be formed that may sit within concave recesses formed by adjacent protrusions extending proximally from lysing lip 1933.

Yet another embodiment of a lysing tip 2033 is depicted in FIGS. 20a and 20b. This embodiment essentially combines the rear portion of lysing tip 1833 with the front portion of lysing tip 1933. In other words, lysing tip 2033 lacks any recesses defined by adjacent protrusions and instead comprises two sets of lysing segments that extend from or are slightly recessed within relatively flat front (2060f) and rear (2060r) surfaces of lysing tip 2033 along the front and rear portions, respectively. Thus, lysing tip 2033 may be configured to provide for forward and rearward motion in essentially the same manner. By contrast, lysing tips 1833 and 1933 may provide a differential between the feel and/or maneuverability of the tip in the proximal vs. distal directions. Although this differential may be preferable for certain procedures, a surgeon may prefer to avoid having such a differential, in which case either the non-recessed embodiment of FIGS. 20a and 20b or the embodiments having concave recessed formed along both the front and the rear of the lysing tip, as previously discussed and described, may be preferred.

FIGS. 21a-21c depict a 3-bead oscillating lysing instrument 2100. Instrument 2100 comprises a lysing tip 2133 and main shaft 2190. Lysing tip 2133 comprises a shaped body, which may be comprised of a suitable durable material designed to withstand strong vibrational forces, for example, titanium and/or a suitable alloy thereof. Tip body 2133b may comprise a unitary shape that forms the structure depicted in the drawings, namely, opposing beads 2150, struts 2180, and two distal recesses and two proximal recesses which each correspond to a lysing and/or cutting segment, as previously described. As a finished product, one or more surfaces of lysing instrument 2100 may be coated. In some embodiments, instrument 2100 may be configured to lyse without use of electrosurgical energy and therefore the coating applied to lysing tip 2133 may comprise a conductive or non-conductive material.

Oscillating lysing tip 2133 comprises structural features similar to embodiments previously described herein, however, these features/elements are preferably indefeasibly coupled as one unitary formed body. Distal protrusions 2101d and distal recesses 2102d may be substantially defined by a plurality of distal tips 2150d of beads 2150, extension/nose 2136, distal lysing element 2161d, and/or the front edge of strut 2180. Proximal protrusions 2101p and recesses 2102p may be defined by proximal tips 2150p of beads 2150, extension/nose 2136, proximal lysing elements 2161p, and/or the back edge of strut 2180. Distal lysing segments 2161d and proximal lysing segments 2161p may be sharpened along the edge to facilitate mechanical cutting/dissection.

Oscillating means 2199 may be located along the shaft at a resonant point that vibrates tip 2133 as specified. The power source to drive oscillating means 2199 is readily known to those skilled in the art. In some embodiments, oscillating means 2199 may operate in the range from about 23 to about 40 kHz. Oscillating means 2199 may comprise hard type piezoceramics as such may have higher Q factors, better linearity, and are harder to depolarize. An example of such ceramic is Navy Type III material, for example, APC 880 from American Piezoceramics, Mackeyville, PA.

The embodiments depicted in FIGS. 21a-c may provide surgeons unique lysing capabilities in certain procedures, for example, cellulite and face/neck tightening procedures.

In some embodiments, a fluid may be distributed at or within one, some or all of the recessions 2102d/2102p via tubes 2194j that may be supplied fluid by fluid channel 2194. Supply of a fluid to the cutting site may reduce eschar and reduce heat.

In some embodiments, a skin protection means that reduces friction at the entrance incision may be disposed around the wound entrance location. Such means may be made from a rigid, low friction plastic such as Teflon or HDPE, in a hollow shaft form, surrounding the main driving element.

FIGS. 22a-e depicts an embodiment of a lysing tip 2233 that may be coupled to an instrument or may itself be used as a lysing instrument. Lysing tip 2233 may comprise shaft 2233b and a two-way lysing/treatment tip 2233t comprising two beads 2250 defining a single distal treatment recession 2202d and a single proximal treatment recession 2202p along one side of shaft 2233b. Lysing tip 2233 may be configured for two-way motion (i.e., forward/distal and reverse/proximal motion) due to, as discussed below, the presence of lysing segments that face in the forward/distal direction to facilitate forward motion of lysing tip 2233 through tissue and other lysing segments that face in the rearward/proximal direction to facilitate rearward/proximal motion of lysing tip 2233 through tissue in the opposite direction. The shaft 2233b of lysing tip 2233 may physically couple lysing tip 2233 to an electrosurgical energy source such as an electrosurgical pencil (not shown) via, in some embodiments, a conductive insert or conductive core 2260s, which may act as a conduit for electrosurgical energy to flow to lysing tip 2233. In the depicted embodiment, conductive core 2260s comprises an integral extension from electrode 2260. In other contemplated embodiments, however, conductive core 2260s may be coupled to electrode 2260, either directly or indirectly such as by way of a wire or the like.

As previously mentioned, lysing tip 2233 comprises one distal-facing lysing segment 2261d and one proximal-facing lysing segment 2261p. Each of these various lysing segments may collectively be defined by a single electrode or each by its own respective electrode. In the depicted embodiment, a single electrode 2260 is used to define each of the various lysing segments and a shaped non-conductive body is used to define various beads, protrusions, and/or other features that define recessions into which the lysing segments are positioned. The non-conductive body of tip 2233 defines two (or more, as shown in other embodiments) forward-facing distal protrusions 2201*d* defined by the distal tips 2250*d* of beads 2250 and a distal recession 2202*d* (more than one distal recession may be provided on other embodiments) positioned between distal tips 2250*d* of beads 2250. Lysing tip 2233 may further comprise one or more rearward-facing proximal protrusion/recession lysing segments or lysing segment pairs as well to facilitate proximal motion of the device/tip 2233 through tissue. For example, beads 2250 further define rearward protrusions 2250*p* defined by the proximal tips 2201*p* of beads 2250 and recessions 2202*p* defined by proximal tips 2201*p* along with the shaft/neck of lysing tip 2233.

However, in the embodiment of FIGS. 22*a*-22*e*, the recession on one side of shaft 2233*b* is filled by tissue-deflecting strut 2281, which is configured to allow for reverse treatment of tissue on the opposite side while deflecting tissue and/or avoiding catching tissue on the side of tissue-deflecting strut 2281. As best shown in FIG. 22*d*, opposing upper and lower surfaces 2281*f* of strut 2281 may be recessed from the body of bead 2250, recessed from shaft 2233*b*, and/or recessed from strut 2280. However, alternative embodiments are contemplated in which strut 2281 may be thicker and may therefore have the same or a greater thickness than one or more of these adjacent elements. Strut 2281 is also preferably non-conductive and may therefore protect adjacent tissue from the underlying electrode(s) such that reverse lysing/tissue treatment only takes place on the opposite side of the device.

Beads 2250 may also be supported by and/or spaced by one or more rigid or substantially rigid cross-struts 2280, each of which may be permanently or temporarily coupled between adjacent beads 2250 and, in some embodiments, may be further coupled along a proximal region with the shaft 2233*b* of lysing tip 2233. In the preferred embodiment shown in FIGS. 22*a*-22*e*, the shaped nonconductive body defining beads 2250 may further comprise one or more slots, such as slot 2280*s* that may extend between strut 2280. Slot 2280*s* may define a distal slot opening defined on its upper and lower sides by strut 2280 and on its left and right sides by one or more tunnels 2250*t* in beads 2250. In alternative embodiments, the shaped nonconductive body defining beads may lack slots.

In this embodiment, electrode 2260 may be positioned within distal slot opening and operationally positioned and configured to define lysing segment 2261*d*, which is defined by an exposed portion of electrode 2260, to face distally through the distal slot opening and to allow for delivery of electrosurgical energy therethrough. The shaped nonconductive body may further comprise one or more proximal slot openings through which the proximal lysing segments 2261*p* of electrode 2260 may be exposed to allow for delivery of electrosurgical energy therethrough and to facilitate rearward movement of lysing tip 2233 through tissue. Again, due to the presence of strut 2281 on one side of the device, only a single proximal lysing segment 2261*p* is defined on the depicted embodiment.

Beads 2250 and struts 2280 and/or 2281 may be comprised of ceramic, cermet, glass, various halogenated hydrocarbons, and any other suitable nonconductors.

When an electrosurgical generator is activated by a surgeon, electrosurgical energy may be transmitted through a conductive core, insert, or wire, for example, through shaft 2233*b*, to electrode 2260, which activates lysing segments 2261*d* and 2261*p* for delivery of electrosurgical energy into tissue.

In some embodiments, the conductive material of electrode 2260 may comprise: steel, nickel, alloys, palladium, gold, tungsten, silver, copper, platinum and/or another conductive metal that does not give off toxic residua at operating temperatures. In some embodiments, electrode 2260 may be coated with a non-stick and/or relatively inert material which may comprise gold, silver, rhodium, titanium, titanium alloys, tungsten, certain cobalt alloys and the like, along with combinations of any of the foregoing.

In some embodiments, the width of the distal portion of lysing tip 2233 (defined between the outermost portions of the outermost beads 2250) may be between about 3 mm and about 5 mm and the length of the beads, which may be defined by the shaped nonconductive body, may be between about 3 and about 10 mm.

By providing both distal and proximal lysing segments for dissection and/or coagulation of tissue in an anterograde and/or retrograde fashion, a number of benefits may be achievable. For example, the efficiency of dissection may be increased because a forward pass may separate tissue and moving the tip in the reverse direction also separates tissue rather than merely readying the tip for another forward pass. As another example, providing both distal and proximal lysing segments, preferably using recessions, may reduce in the necessary width/size of operating tool so various models may fit down smaller diameter cannulas and/or entrance-wounds/body-openings for minimally invasive surgery and/or entrance wound/scar minimization. In addition, providing for retrograde dissection may favor various dissection angles or patterns when various force vectors are placed upon the target tissues and/or target tissue planes.

It should be understood that the embodiments disclosed herein may have value and application in various different types of surgery. For example, the lysing tips, devices, and methods disclosed herein may be useful for cosmetic surgery, including facial dissection, neck dissection, creation of pockets for implants, axillary hyperhidrosis treatment, and cellulite treatment, and may also be useful in connection with internal surgeries, such as laparoscopic and/or endoscopic procedures. Thus, the device may be introduced directly into the body from an opening in the skin or may be introduced using a trocar and/or cannula in other types of surgical procedures.

While the device is energized with electrosurgical energy, beads 2250 and struts 2280 and 2281 are preferably non-conductive.

As previously mentioned, lysing tip 2233 comprises a plurality of beads 2250 and a plurality of recessed lying segments that, again, may be defined by one or more electrodes. It should be noted that in the embodiments of FIGS. 22*a*-22*e*, beads 2250 are supported laterally along their respective inner sides by strut 2280. In other words, beads 2250 each define a primary and/or elongated axis extending between their respective distal tips and proximal tips. In the depicted embodiment, these axes extend at least substantially parallel to the axis of the instrument 2200. Rather than being supported from behind, such as by an element extending between the proximal ends of beads 2250, beads 2250 are supported along their respective sides by an element (strut 2280 in the depicted embodiment) that extends at least substantially perpendicular relative to their respective primary axes so that the bead shape is still apparent from the structure of lysing tip 2233. In addition, although one of the beads 2250 is coupled to tissue-deflecting strut 2281 from behind, it can be seen from several of the accompanying figures, such as FIGS. 22d and 22e for example, that the rearward/proximal facing portion of this bead and its shape are also still apparent. It should also be apparent from these figures that the bead shape on the proximal portion of the bead coupled with strut 2281 is apparent on the outer portion/surface of the bead (relative to shaft 2233b) and at least a portion of the inner portion/surface of the bead. Of course, in alternative embodiments in which the beads are spherical, or at least substantially spherical, the beads need not define an elongated axis but, in some such embodiments, at least a portion of the proximal bead shape may be apparent behind a cross-strut connecting the bead or beads to an adjacent bead or shaft of an instrument.

It should also be understood that beads 2250 are preferably, at least along their respective surfaces, non-conductive, or at least substantially non-conductive. As such, the beads 2250 can serve a protective function to prepare the adjacent tissue for sequestered dissection and/or electrodessication by the adjacent lysing segments. Otherwise stated, by providing an adjacent protruding, non-conductive surface, the lysing segments may be sequestered from the tissue to be treated, while the bead surfaces, preferably protruding distally and proximally, may be used to stretch, spread, guide, and/or position the target tissue without directly delivering electrosurgical energy from the beads to the dissected tissues. Delivering electrosurgical energy from the beads may cause unwanted tissue damage.

Shaft 2290 may couple with tip 2233 to facilitate transfer of electrosurgical energy in a desired manner and/or allow for manually dissection in the absence of electrosurgical energy. Shaft 2290 may be deformable, that is, it may be bent so as to angle the lysing tip in a desired direction, for example, to ensure the lysing tip is angled up by 3 to 10 degrees so as to direct cutting/lysing towards the dermis of the skin in a cosmetic procedure. In some embodiments, a malleable conductor covered by a malleable dielectric cover may be deformed by manually applied external forces and then maintain its deformed shape during the period that primarily axial forces associated with normal use act upon the malleable shaft.

In some embodiments, the shaped nonconductive body may comprise one or more sensors, which in some such embodiments may be positioned within one or more corresponding sensor openings that may serve as locations for various sensors including but not limited to temperature sensors, fiberoptics, positioning sensors, RFID sensors/tags, and the like. Such sensor openings may be connected to one or more ducts that may pass through the shaped nonconductive body of tip 2233 and may exit on the proximal end of lysing tip 2233. Alternatively, sensors positioned in such sensor openings may be configured to deliver data wirelessly. In some embodiments, sensors may be positioned on a distal portion of one or both of beads 2250 and may be used to measure temperature during the instrument's back stroke because the treated tissue would typically pass adjacent to such sensors during a back stroke. Thus, distally-positioned temperature sensors may allow for measurement of tissue temperature following treatment. Similarly, temperature sensors may be positioned proximally for taking tissue temperature measurements during and/or after a forward stroke. In some embodiments, a temperature or other sensor measurement may be taken during an RF activation or between RF pulses. In alternative embodiments, the sensor exposed at a sensor opening may be a fiberoptic that may sense tissue color and/or the presence of blood.

While instrument 2200 is energized with electrosurgical energy, beads 2250 and struts 2280 and 2281 are preferably non-conductive, thus minimizing unwanted electrical discharge. The electrically conductive electrode 2260 may be configured to deliver electrosurgical energy through the various distal and/or proximal lysing segments, as previously mentioned.

Beads 2250 and struts 2280 and 2281 may be comprised of ceramic, cermet, glass, various halogenated hydrocarbons, and any other suitable nonconductors. Beads 2250 may be restricted in their motion and/or affixed to struts 2280 and 2281 via direct coupling (i.e., continuous/integral ceramic) and/or conductive materials such as those that comprise electrode 2260. As well, indirect sealing methods such as epoxy or ceramic glues or potting mixes and the like may be used to seal any unwanted seams or openings to maintain non-conductive integrity in the desired locations. When an electrosurgical generator is activated by a surgeon, electrosurgical energy may be transmitted through any suitable electrical coupling elements to electrode 2260.

It should also be understood that any of the lysing tips and/or instruments disclosed herein, including but not limited to those depicted in FIGS. 22a-22e, may be coupled or otherwise used with another surgical system, such as a robotic surgical system.

FIGS. 23a-23e depict an embodiment of a lysing instrument 2300. Instrument 2300 may comprise shaft 2390 and two-way lysing tip 2333 comprising a treatment tip 2333t and a shaft portion 2333b of tip 2333. Lysing tip 2333 is configured for two-way motion (i.e., forward/distal and reverse/proximal motion) due to, as discussed below, the presence of lysing segments that face in the forward/distal direction to facilitate forward motion of lysing tip 2333 through tissue and one lysing segment that faces in the rearward/proximal direction to facilitate rearward/proximal motion of lysing tip 2333 through tissue.

In the embodiment of FIGS. 23a-23e, the recession on one side of shaft 2333b is occupied by tissue-deflecting strut 2381, which is configured to allow for reverse treatment of tissue on the opposite side while deflecting tissue and/or avoiding catching tissue on the side of tissue-deflecting strut 2381. As best shown in FIG. 23d, opposing upper and lower surfaces 2381f of strut 2381 may be recessed from the body of bead 2350, recessed from shaft 2333b, and/or recessed from strut 2380. Thus, the shape of the proximal portion of the bead 2350 coupled with strut 2381 is still apparent from behind strut 2380. However, alternative embodiments are contemplated in which strut 2381 may be thicker and may therefore have the same or a greater thickness than one or more of these adjacent elements. Strut 2381 is also preferably non-conductive and may therefore protect adjacent tissue from the underlying electrode(s) such that reverse lysing/tissue treatment only takes place on the opposite side of the device. Use of a tissue deflecting strut on one side, such as strut 2381, may be particularly useful when dissecting fatty and/or other tissues that are particularly fibrous, such as facial and/or neck tissues, especially those having undergone previous surgery or other trauma.

The rearward/proximal lysing segment of instrument 2300 extends, as shown in the figures, at least substantially perpendicular to the shaft 2390 of instrument 2300. In the depicted embodiment, both the distal and proximal lysing segments define concave portions and, more particularly, curved concave portions. However, both of the points at which these lysing segments terminate (at or adjacent to a bead on one end and at or adjacent to shaft 2390 at the opposite end) define a line that is perpendicular, or at least substantially perpendicular, to shaft 2390 and/or the primary/elongated axes of the beads themselves. Similarly, at a central or at least substantially a central point along each of the lysing segments between the two termination points previously referenced, a tangent line to this curvature is perpendicular, or at least substantially perpendicular, to shaft 2390 and/or the primary/elongated axes of the beads. Thus, despite the curvature of the depicted lysing segments, they should each be considered to extend at least substantially perpendicular to the shaft 2390 of instrument 2300, and at least substantially perpendicular to the elongated and/or primary axis of beads 2350. These aspects of the lysing segments may apply to any of the other embodiments depicted and/or otherwise disclosed herein.

However, other embodiments are contemplated in which these lysing segments may extend at another angle relative to the shaft 2390 and/or primary axis of instrument 2300. In the depicted embodiment, the proximal/rearward facing lysing segment(s) may extend perpendicular, or at least substantially perpendicular, from the axis of shaft 2390, as shown in FIG. 23c. In other contemplated embodiments, the proximal/rearward lysing segment may extend at an angle of between about 60 degrees and about 120 degrees from the shaft 2390 and/or primary axis of instrument 2300. Shaft 2390 may physically couple lysing tip 2333 to an electrosurgical energy source such as an electrosurgical pencil (not shown) via conductive core 2360s, which in the depicted embodiment comprises a conductive rod, which may be electrically conductive and act as a conduit for electrosurgical energy to flow to lysing tip 2333. In the depicted embodiment, conductive core 2360s comprises an integral extension from electrode 2360. In other contemplated embodiments, however, conductive core 2360s may be coupled to electrode 2360, either directly or indirectly such as by way of a wire or the like.

Lysing tip 2333 comprises one or more distal-facing lysing segments and one or more proximal-facing lysing segments. Each of these various lysing segments may be defined by a single electrode or each by its own respective electrode. In the depicted embodiment, a single electrode 2360 is used to define each of the various lysing segments, including both the distal facing lysing segments that are configured to facilitate forward/distal motion of instrument 2300 and the proximal-facing lysing segment that is configured to facilitate rearward/proximal motion of instrument 2300. In this particular embodiment, a single electrode 2360 defines both distal-facing and proximal-facing lysing segments. However, it is contemplated that, in other embodiments, separate electrodes/lysing members may be used to separately define one or more distal-facing and one or more proximal-facing lysing segments. A non-conductive body 2333b may be used to define various beads, protrusions, and/or other features that define recessions into which the lysing segments are positioned. In some embodiments, the recessions may be defined by beads, struts, and/or lysing segments. Non-conductive body 2333b defines three forward-facing distal protrusions 2301d defined by the distal tips 2350d of beads 2350 and nose 2336 of shaft 2390 and distal recessions 2302d (more than one distal recession may be provided on other embodiments) positioned between distal tips of beads 2350d and nose 2336. Lysing tip 2333 may further comprise one or more rearward-facing proximal protrusion/recession pairs as well to facilitate proximal motion of the device 2300 through tissue. For example, beads 2350 further define a rearward protrusion defined by the proximal tip 2301p of bead 2350 and recession 2302p defined by proximal tip 2301p of bead 2350 along with strut 2380. By providing both distally and proximally facing lysing segments, and preferably by also providing an adjacent bead surface to stretch and/or guide target tissue without directly treating/electrifying the tissue (due to the nonconductive surface provided by the bead) the device may be configured to effectively prepare and, ultimately, dissect target tissue in both directions with or without electrosurgical energy. Thus, it may be preferred to provide a bead having pointed distal and/or proximal surfaces. As is the case with beads 2250 and 2550, these pointed surfaces may be spatially curved in at least one plane (or more than one) and may therefore be smoothly pointed rather than sharply pointed.

Again, on the opposite side, in place of what would otherwise define another recession and corresponding lysing segment, tip 2333 comprises a tissue-deflecting strut 2381 that extends from the rear end of the adjacent bead 2350 to shaft 2390 preferably in a curved manner without any sharp corners, as shown in the drawings.

Shaped nonconductive body 2333b may comprise one or more beads 2350 that may be supported by and/or spaced by one or more rigid or substantially rigid struts 2380, each of which may be permanently or temporarily coupled between adjacent beads 2350 and/or between an outer bead and the nose 2336 and/or shaft 2390 or shaft portion of lysing tip 2333. In some embodiments, strut 2380 may be further coupled along a proximal region with the shaft of lysing tip 2333. In the preferred embodiment shown in FIGS. 23a-23e, shaped nonconductive body 2333b may comprise one or more slots that may extend along each strut 2380. Such slot(s) may define a distal slot opening defined on its upper and lower sides by strut 2380 and/or nose 2336 and on its left and right sides by one or more beads 2350.

In this embodiment, electrode 2360 may be passed through distal slot openings and operationally positioned and configured to define distal lysing segments 2360d, which may be defined by exposed portions of electrode 2360 on either side of nose 2336, to face distally through the distal slot opening and to allow for delivery of electrosurgical energy, or another type of suitable energy for modification of tissue, therethrough.

In other embodiments such as in FIG. 23c, the nose defining the center protrusion may be manufactured to receive a nose insert 2336 therein, which may be coupled in place via a coupling agent such as a ceramic glue, fastener, or the like. In still other embodiments, nose insert 2336 (the volume between the upper portion of the nose and the lower portion of the nose) may be filled with a filling agent, such as a high temperature epoxy or the like.

Shaped nonconductive body 2333b may comprise one or more sensor openings, which may serve as locations for various sensors including but not limited to temperature sensors, fiberoptics, positioning sensors, RFID sensors/tags, and the like. Such openings may be connected to one or more ducts that may pass through shaped nonconductive body 2333b and exit on the proximal end of lysing tip 2333. Alternatively, sensors, including but not limited to sensors positioned in said sensor openings, may be configured to deliver data wirelessly. It should be noted that one or more sensor openings may be located on the distal end of one or more of the beads 2350. In addition, one or more sensors may be located in a nose sensor opening. In some embodiments and implementations, sensors may be used to measure temperature during the instrument's back stroke. In some embodiments, said measurement may be taken during an RF pulse or between RF pulses. In alternative embodiments, the sensor exposed at any sensor opening may be a fiberoptic that may sense tissue color and the presence of blood.

Beads 2350, nose 2336, tissue deflecting strut 2381, and/or strut 2380 may be comprised of ceramic, cermet, glass, various halogenated hydrocarbons, and any other suitable nonconductors.

When an electrosurgical generator is activated by a surgeon, electrosurgical energy may be transmitted through conductive core 2360*s*, through shaft 2390, to electrode 2360, which activates lysing segments 2360*d* and 2360*p* for delivery of electrosurgical energy into tissue.

In some embodiments, the width of the distal portion of lysing tip 2333 (defined between the outermost portions of the outermost beads 2350) may be between about 6 mm and about 12 mm and the length of the beads (between proximal and distal ends), which may be defined by the shaped nonconductive body 2333*b*, may be between about 3 and about 10 mm.

It should be noted that in being able to dissect in forward and backward directions, lysing tips 2233 and 2333 uniquely may be more efficient than single direction lysing tips. Retrograde dissection may also facilitate use of alternative tissue tension force vectors adjacent to the target tissues and/or target tissue planes. Tissue tension force vectors may be applied by surgical assistants and/or the surgeon's non-instrument hand. As well, retrograde dissection may allow for alternative dissection angles.

While the device is energized with electrosurgical energy, beads 2350, nose 2336, tissue deflecting strut 2381, and strut 2380 are preferably non-conductive in order to perform the blunt dissection function. However, in some embodiments, one or more of these elements may comprise a conductive core and a non-conductive coating or shell.

In some embodiments, lysing member/electrode assembly 2360 comprises a rigid and/or substantially rigid plate as shown in FIG. 23*c*. In such embodiments, one or both of proximal lysing segments 2360*p* and/or distal lysing segments 2360*d* may be configured to be electrically coupled with electrode shaft 2360*s*. In some such embodiments, electrode 2360 may comprise a single, unitary piece of a suitable conductive material that serves each of these functions. One or more slots may be configured so as to tightly receive lysing member electrode assembly 2360 so as to prevent or at least inhibit movement or unwanted RF energy escape. As previously mentioned, lysing tip 2333 may comprise a plurality of beads 2350 and a plurality of recessed lying segments that, again, may be defined by one or more electrodes. It should be noted that in the embodiments of FIGS. 23*a*-23*e*, beads 2350 are supported laterally along their respective inner sides by strut 2380.

Shaft 2390 may couple with tip 2333 to facilitate transfer of electrosurgical energy in a desired manner and/or allow for manually dissection in the absence of electrosurgical energy. Shaft 2390 and/or one or more portions of tip 2333 may be deformable, that is, it may be bent so as to angle the lysing tip in a desired direction, for example, to ensure the lysing tip is angled up by 3 to 10 degrees so as to direct cutting/lysing towards the skin in a cosmetic procedure.

While system 2300 is energized with electrosurgical energy, beads 2350, tissue deflecting strut 2381, and strut 2380, or at least a portion of one or more of these elements (such as surfaces other than those exposed for defining/exposing lysing segments), are preferably non-conductive, thus minimizing unwanted electrical discharge. The electrically conductive electrode 2360 may be configured to deliver electrosurgical energy through the various distal and/or proximal lysing segments, as previously mentioned.

In some embodiments, the conductive material of electrode 2360 may comprise: steel, nickel, alloys, palladium, gold, tungsten, silver, copper, platinum and/or another conductive metal that preferably does not give off toxic residua at typical operating temperatures. In some embodiments, electrode 2360 may be coated with a non-stick material which may include gold, silver, rhodium, titanium, titanium alloys, tungsten, certain cobalt alloys and the like.

Beads 2350, nose 2336, tissue deflecting strut 2381, and strut 2380 may be comprised of ceramic, cermet, glass, various halogenated hydrocarbons, and any other suitable nonconductors. Beads 2350 may be restricted in their motion and/or affixed to strut 2380 and/or strut 2381 via direct coupling (i.e., continuous/integral ceramic) and/or conductive materials such as those that comprise electrode 2360. As well, indirect sealing methods such as epoxy or ceramic glues or potting mixes and the like may be used to seal any unwanted seams or openings to maintain nonconductive integrity in the desired locations. When an electrosurgical generator is activated by a surgeon, electrosurgical energy may be transmitted through any suitable electrical coupling elements to electrode 2360.

It should also be noted that beads 2350, on the same instrument, may be of the same shape, may be of different shapes, and/or may be angled/tilted up or angled/tilted down by between about 3 to about 15 degrees to assist in guiding the tip towards the upper or lower tissue plane. In other embodiments, each bead may be angled in a different direction. In some embodiments, struts 2380 and/or 2381 may remain parallel to the upper and/or lower surfaces of the device or may follow the same angle as its respective tilted bead.

In another embodiment, lysing tip 2333 may be configured to oscillate in various planes which may assist in reducing eschar buildup and may aid in the movement of lysing tip 2333 through tissues with mechanical energy. In some such embodiments, shaft 2390 may comprise a piezoelectric or oscillating/vibrating motor unit, which may be placed in the handle or at another point between the handle and the distal tip wherein the necessary harmonic motion is created. High energy frequencies, like in the ultrasound regions, may be chosen but may be too powerful for a multi-component device. However, lower frequencies with lower energy, similar to those used in toothbrushes to aid in cleaning, may provide the necessary energy to reduce eschar and assist in lysing. Lower frequencies may be possible by use of a voice coil, however, piezoceramics may be preferred. Higher frequency in the ultrasound range requires a smaller piezo. Said frequency range may be from about 1 kHz to about 80 kHz, with a preference for between about 21 to about 40 kHz. A hard-ceramic type piezoceramic motor may be preferred, and for lower excursion, the type could be expanded to include Navy Type I, exemplified by APC 840.

FIG. 24 depicts another alternative embodiment of a lysing instrument/tip 2400 comprising a single bead 2450 extending parallel, or at least substantially parallel in related embodiments, to shaft 2433 of instrument 2400. The proximal end of shaft 2433 may be configured to couple with an electrosurgical instrument and/or power source. Bead 2450 is coupled to shaft 2433 by way of a strut 2480, which may be similar to strut 2380 described above. Slots and/or openings may be formed in strut 2480, the inner side of bead 2450, and/or the adjacent outer side of shaft 2433 to allow for a distal lysing segment 2461*d* and a proximal lysing segment 2461*p*, respectively, to protrude from respective recessions 2402*d* and 2402*p* defined by bead 2450, shaft 2433 (tip 2433*d* of shaft 2433 for distal lysing segment 2461*d*), and strut 2480. Again, the various lysing segments may be defined by a single electrode or individual, distinct electrodes, as desired.

With respect to the embodiment of FIG. 24, again the lysing tip is configured to allow for distal and proximal treatment motion and provides distal and proximal lysing segments for this purpose.

FIGS. 25*a*-25*c* depict a lysing instrument/tip that is a modified version of the embodiment of FIG. 24 in which, rather than protruding from the recessions, the portions of lysing segments 2561*d* and 2561*p* defined by electrode 2561 are recessed within the respective recessions defined by shaft 2533, bead 2550, and strut 2580. Thus, as best shown in FIG. 25*c*, electrode 2561 is recessed within the portion of the distal and proximal recessions defined by strut 2580. By recessing the electrode/lysing segments within the structure of the body of the tip as shown in FIG. 25*c*, precision and/or safety may be enhanced and therefore this variation may be preferred for certain surgical procedures and/or by certain physicians over embodiments in which the electrode/lysing segments protrude from the body of the tip as is the case with the embodiment of FIG. 24. As mentioned in connection with other embodiments, a conductive core 2561*c* and/or wires or other means for electrical coupling may be used to electrically couple electrode 2561 through shaft 2533 to a source for electrosurgical or other treatment energy. Of course, in still other alternative embodiments, the portions of the electrode defining the lysing segments may be flush with the ends of the strut(s), the shaft, and/or the bead(s).

Yet another embodiment of a lysing instrument 2600 is depicted in FIGS. 26*a*-26*d*. Lysing instrument 2600 comprises a shaft 2690 terminating in a lysing tip 2633 comprising a plurality of beads 2650 defining a plurality of adjacent protrusions 2601*d*/2601*p* and lysing segments 2661*d*/2661*p* positioned in recessions extending between adjacent protrusions 2601*d*/2601*p*. As previously mentioned, two struts 2680 are used to couple adjacent beads 2650. In the depicted embodiment, each of the lysing segments is defined by a single electrode 2661, although, as previously mentioned, alternative embodiments are contemplated in which multiple electrodes may be used, each of which may be used to define a single, or multiple, lysing segments. A conductive core 2661*c* may be coupled with the electrode 2661 to allow for delivery of an electrosurgical or other treatment energy to the various lysing segments.

Shaft 2690 further comprises an angled portion 2690*b* that extends shaft 2690 away from its proximal axis. In the depicted embodiment, angled portion 2690*b* is configured to allow middle bead 2650 to be positioned along, or at least substantially along, the proximal axis of shaft 2690 and to allow the opposing outer beads to each extend beyond the profile of the proximal portion of shaft 2690 on opposite sides so that the treatment width defined by the opposing outer beads is wider than shaft 2690.

As best shown in FIG. 26*b* and the cross-sectional view of FIG. 26*d*, the distal end of shaft 2690 forms a shape that mimics the distal shape of the two beads 2650 and therefore may provide a function similar to beads 2650 by defining a protrusion 2633*d* and partially defining an adjacent recession for an adjacent lysing segment.

In some embodiments, including the embodiments depicted in FIGS. 26*a*-26*d*, the tip comprises an anfractuous tip configured to be inserted through a relatively small entrance wound, such as an entrance wound of between about 2.5 mm and about 5 mm. Thus, the length of the beads on the tip may be about 4 mm or may not exceed about 5 mm in some embodiments. This may allow the tip to be inserted through the entrance wound with the bead furthest from the shaft first and the angled/snaked through the entrance wound to minimize the requisite entrance wound size. This may also allow for avoiding use of hinges, rotational elements, etc., and may allow for use of a wider treatment area (typically defined between outermost beads on the treatment tip) without requiring such rotational elements.

As also depicted in FIG. 26*b*, some embodiments may be configured with one or more dimensions less than a threshold value to allow for use with a relatively small entrance wound. For example, a surgeon may possibly introduce the device into the entrance wound/incision via the distal tip of the outermost bead 2650*d* with a corner of the entrance wound abutting the adjacent strut 2680 and/or lysing segment 2661*d*. Thus, in some preferred embodiments, the limiting distance D1, which may be no more than about 6 mm in some embodiments, and in more preferred embodiments may be no more than about 5 mm, allows the opposing end of the entrance wound to abut the proximal tip of outermost bead 2650*p*. The process may then be repeated from bead to bead eventuating in the distal end of the shaft 2633*d* contacting another end of the entrance wound while the most proximal inner strut 2680 and/or lysing segment contacts the opposing end of the entrance wound as the device is rotated to prepare for the introduction of shaft 2690*b* into the entrance wound. Thus, distance D2 also becomes a limiting factor in relation to the size of the entrance wound. Thus, distance D2 in preferred embodiments may also be no more than about 6 mm and more preferably no more than about 5 mm. As shown in the drawings, distance D1 is measured from the proximal end of the outermost/distal bead 2650 to a corner at which a distal-most portion of the adjacent strut 2680 and the outermost/distal bead 2650, measured along the three-dimensional surface of this bead 2650. Similarly, distance D2 is measured from the distal tip 2601*d* of shaft 2690 to a corner between the adjacent strut 2602*d* and shaft 2690, the distance again being measured along the curved and/or three-dimensional shape of the bead-mimicking distal end of the shaft 2690, which distance may correspond with the maximum preferred length of the entrance wound for various cosmetic procedures not taking into account tissue stretch and special techniques to incise the entrance incision(s). Although not shown in the drawings, preferably this maximum threshold distance applies to each of the other similar elements in the tip, such as the center bead 2650 and adjacent struts.

FIG. 26*e* depicts an embodiment similar to that embodiment depicted in FIGS. 26*a*-26*d*. However, instrument 2600' in FIG. 26*e* comprises a tip 2633' that extends at a right angle relative to shaft 2690'. Thus, shaft portion 2690*b'* of tip 2633' is straight and extends along the same axis as shaft 2690'.

FIGS. 27*a*-27*b* depict an embodiment similar to that of the embodiment depicted in FIGS. 26*a*-26*d*. However, instrument 2700 depicted in FIGS. 27*a* and 27*b* comprise an angled shaft portion 2790*b* that provides for another example of an anfractuous tip 2733. In this embodiment, the anfractuous tip extends outward relative to shaft 2790. As previously described, tip 2733 further comprises a plurality of beads 2750 coupled to each other by way of struts 2780. In addition, distal and proximal recessions 2702*d*/2702*p* are defined in between adjacent beads 2750 and/or a distal end of shaft 2790*b* that mimics the shape of a bead. Providing an angled treatment tip as shown in FIGS. 27a and 27b allows for use of a unique treatment technique, as discussed below in connection with FIG. 27c.

FIG. 27c depicts an example of a method for forming a path to a target tissue using instrument 2700. This method may begin by inserting the tip 2733 through an entrance wound E, as previously discussed. Then the surgeon/practitioner may consider one of the following patterns using instrument 2700 for establishing a path to the site for tissue treatment. In a first example, a "short" saw-tooth pattern may be used in which the tip 2733 is advanced by a first distance, which may be about 2 cm in preferred implementations, with the tip 2733 pointing in a first direction (e.g., to the front-right). Then the tip 2733 may be rotated/flipped by 180 degrees at a fork point f so that the tip 2733 now points in a second direction, (e.g., to the front-left), after which the tip 2733 may again be advanced by a similar distance (e.g., 2 cm more). This process may then be repeated as many times as needed until the tip 2733 is at a desired target treatment zone T, as shown in FIG. 27c. The short saw-tooth pattern may be preferable in soft fat where short flipping advances result in a saw-tooth pattern for the shaft to follow and, depending upon the rigidity of the shaft and the density and rigidity of the tissue surrounding the path, the shaft may still be able to apply the correct force vector to the tip so that the tip may advance in various directions at the treatment area without having to re-angle the shaft while dissecting the tissue. Simple flipping after various advancements in the treatment area may allow relatively good dissection at a distance. In alternative methods, a surgeon may prefer to combine these two techniques.

In another example of a method for forming a path to a target tissue zone using instrument 2700, a long saw-tooth pattern may be used in which the tip 2733 may be advanced a longer distance, such as between about 5 to about 10 cm with the tip 2733 pointing in the first direction (e.g., to the front-right), after which the tip 2733 may be rotated/flipped 180 degrees so that the tip now points in a second direction, (e.g., to the front-left) and advanced an additional 5-10 cm. In some implementations, the tip 2733 may be withdrawn via one or more back-strokes, possibly while energizing the proximal lysing segments. Alternatively, or additionally, the tip 2733 may be withdrawn and fore-strokes may be made as desired using the energized distal lysing segments to diminish/lyse the remnant saw-tooth that is unseen below the surface tissues but represents the path the device took during initial movement. If the surgeon feels that the saw-tooth is sufficiently diminished and possible future tension on the shaft minimized, the process may be repeated as many times as necessary until the tip 2733 is at the target treatment zone T and/or a sufficient path for a subsequent treatment device has been established using instrument 2700. The long saw-tooth pattern may be used by surgeons once they determine their preferred density of path tissues in respect to the rigidity of the shaft and the distance the shaft must travel.

FIGS. 28a and 28b depict two examples of TMTs for modification of tissues, preferably after another device, such as any of the lysing and/or cutting devices disclosed herein, has dissected tissue preferably to create tissue planes and/or a path within and/or to a target region of a patient. TMT device 2800a comprises a shaft 2890a and a treatment tip 2811a comprising a plurality of isolated electrode termini 2864 through which energy may be delivered for tightening and/or treatment of tissue, such as subdermal/hypodermal/subcutaneous tissue layers and/or adjacent tissue layers. In this embodiment, shaft 2890a is contiguous with tip 2811a and therefore tip 2811a is defined by the presence of termini 2864. Termini 2864 may simply comprise portions through which a conductive core of TMT device 2800a is exposed, or is near the surface of the portion, for delivery of treatment energy, such as radiant heating, resistive heating, thermochromic, microwave, ultrasonic, electrosurgical, intense pulse light, LASER, or any of the other forms of treatment energy disclosed herein. When other, non-electrical types of energy are used, the conductive core may therefore be replaced with another energy deliver conduit, such as a fiber optic bundle for LASER treatment energy or intense pulsed light. Alternatively, termini 2864 may protrude from the surface of tip 2811a and still preferably couple with one or more wires and/or a conductive core to allow for delivery of the energy through shaft 2890a. Conductive projection 2893a/2893b serves to couple the conductive core or another energy delivery conduit of the device to an energy delivery system (not shown). In other embodiments, termini 2864 may not protrude from the surface or be exposed but may preferably define isolated treatment termini below the surface, such as in embodiments utilizing microwave treatment energy. TMT device 2800a further comprises rounded edges 2892a, which may improve the ability of the device to travel through a path preferably created by another device that may comprise any of the lysing tips disclosed herein.

TMT device 2800b is similar to TMT device 2800a except that edges 2892b are not curved/rounded. Thus, TMT device 2800b also comprises a shaft 2890b and a treatment tip 2811b comprising a plurality of isolated treatment electrode termini 2864.

FIGS. 29a, 29b, 30, and 31 depict other embodiments of TMT devices. Each of these TMT devices comprise non-branching, anfractuous, treatment tips. Like TMT devices 2800a and 2800b, these TMT devices may be inserted into relatively small entrance wounds in the skin or other organ systems and/or may be advanced through a tissue path preferably created by one of the lysing tips/devices disclosed herein. Each of the TMT devices disclosed in FIGS. 28-31 is configured to minimize the requisite size for a cutaneous/skin entrance wound and therefore may be ideally configured for use in connection with cosmetic procedures. For example, a 2 to 5 millimeter cutaneous/skin entrance wound may be formed in an area usually covered by a bikini bottom or underwear, which may provide a less visible zone in which to have created a tissue separation using, for example, one or more of the lysing tips/devices disclosed herein. Each of these depicted TMT devices may therefore, in certain preferred embodiments, be configured such that no cross-sectional dimension along the treatment tip and/or a portion of the shaft that may extend through the entrance wound exceeds the size of the entrance wound, which again may be 2-5 mm in preferred embodiments. As previously mentioned, each of the depicted TMT devices in these figures is also non-branching, which may also facilitate extension of the treatment device through an entrance wound of relatively small size.

Thus, one or more of the various depicted TMT devices may be inserted into the relatively small entrance wound, ultimately to be extended through the previously dissected tissue planes for treatment of adjacent tissue. The end of the tip may be inserted into/through the entrance wound. The tip may then be snaked at different angles if necessary, while being advanced into the entrance wound until the shaft portion reaches the entrance wound and/or the tip has been fully inserted into the patient's body. A snaking motion may be thought of as changing the angle of the device while inserting the tip into the entrance wound such that the tip is fully inserted past the entrance wound into the body. The shaft may then be advanced through the entrance wound such that a sufficient amount of the device enters the area/volume between the tissue planes as desired by the surgeon. The TMT device may then be allowed to treat various portions of the exposed tissue plane or planes as it passes in a variety of directions including, but not limited to, fanning to and fro, straight to and fro, windshield wiper, and even random. The TMT device, especially when used in skin, may be monitored by instrumentation including, but not limited to, external infrared camera, thermistor, thermocouple, ultrasonic methods, and the like.

Any of the TMT devices disclosed herein may comprise a device that may be plugged into an electrosurgical pencil and/or another suitable energy source or instrument and may therefore be part of an electrosurgical treatment system. Additional instrumentation that may couple with the TMT may include a grasping device.

With more specific reference to the depicted embodiments, in the embodiments depicted in FIGS. 29a and 29b, TMT 2900a/2900b (the only difference being TMT 2900a comprises smooth/rounded edges and TMT 2900b does not) again comprises a shaft 2990a/2990b that is coupled to a tissue modification tip (TMT) 2911a. As shown in FIG. 29b, instrument 2900b does, however, comprise smooth curves along the opposing sides of the device, including along tip 2911b. However, in this particular embodiment, the edges transitioning from the sides to the top and bottom surfaces are not smooth. Of course, they may be smooth in other embodiments, such as that of FIG. 29a. However, in both of embodiments 2900a and 2900b, all of the curves transitioning from the axis of the shaft (2990a/2990b) to the treatment tip (2911a/2911b) are smooth and therefore lack any sharp points or edges (even though the transitions between the surfaces defining these curves and the upper and lower surfaces in the embodiment of FIG. 29b are sharp/non-smooth). In these embodiments, to be more specific, the tissue treatment tip of both of these embodiments comprises an upper surface, a lower surface, and opposing side surfaces, wherein the opposing side surfaces comprise one or more bends, and wherein each of the one or more bends are smooth and lack any sharp points or edges. In some embodiments, of course, the cross-sectional shape of the shaft and/or tip may have other shapes, such as a circular shape. Tip 2911a/2911b, however, comprises a tip that extends away from the path of shaft 2990a/2990b to create a wider/larger treatment tip. However, as previously mentioned, in these embodiments, the treatment tip 2911a/2911b comprises cross-sectional dimensions that remain relatively small and does not branch to facilitate insertion into a relatively small entrance wound. In the depicted embodiments, these dimensions are the same as shaft 2990a/2990b, although it is conceivable that in alternative embodiments these dimensions may vary slightly from the shaft. Thus, tip 2911a/2911b comprises a non-branching, anfractuous tip comprising a first straight portion 2912a/2912b that extends at an obtuse angle relative to shaft 2990a/2990b, a curved portion 2913a/2913b, and a second straight portion 2914a/2914b that extends at a perpendicular, or at least substantially perpendicular, angle relative to shaft 2990a/2990b. Second straight portion 2914a/2914b comprises the treatment termini 2964. However, it is conceivable that, in alternative embodiments, other portions of tip 2911a/2911b may also comprise electrode treatment termini, another type of treatment termini, or another type of energy window and/or delivery means, such as an elongated bar that may be positioned on the upper and/or lower surfaces of one or more portions of the tip 2911a/2911b. By providing a non-branching, anfractuous tip comprising a relatively constant cross-sectional size that extends in this manner, a treatment width/size that is larger than the cross-sectional width/size of the shaft 2990a and entrance wound may be provided. Conductive projection 2993a/2993b serves to couple the conductive core or another energy delivery conduit of the device to an energy delivery system (not shown).

As previously mentioned, tip 2911a/2911b may comprise an energy window, which may comprise one or more termini 2964 that may be positioned to face upper and/or lower tissue planes that may have already been lysed/dissected. Although the termini 2964 or other energy window elements may terminate on one side of the TMT tip, in alternative embodiments, energy window elements 2964 may terminate on one or more sides/surfaces/portions of a TMT tip, including but not limited to the upper and lower sides/surfaces/portions of tip 2911b In alternative embodiments, a non-conductive cover and/or coating may be provided, which may comprise one or more windows that may allow for a conductive core or other conductive element to extend therethrough to provide for delivery of energy, electrosurgical or otherwise, therethrough.

In alternative embodiments, the various distal segments of the TMT may be positioned in different planes wherein the bends/curves of the tip may direct various segments into different treatment planes. This may be helpful in forcing, for example, treatment window/termini 2964 into a position to contact and/or deliver energy to target tissues in a more desirable fashion.

In some embodiments, TMT systems 2900a/b may be configured for use with bipolar electrosurgical energy rather than monopolar as suggested by the accompanying figures. For example, in some bipolar embodiments, every other termini 2946 may be oppositely charged from its adjacent (close neighbor) termini. This may allow flow of electricity between adjacent termini as opposed to channeling radiofrequency energy through the body to a more distant return zone.

In some embodiments, TMT instrument 2900a may be configured for use with microwave energy rather than monopolar energy as suggested by the accompanying figures. Microwave energy may be used to heat tissue and thus providing a suitable array of microwave emitters would allow for controlled tissue heating and remodeling. In some such embodiments, a suitable microwave generator may be positioned proximal to the tip using a shielded cable that is preferably an integral number of wavelengths in length. For example, National Electronics manufactures/distributes microwave sources. From said generator, a shielded cable, for example, a coaxial cable, may carry the energy to the energy window region of the TMT tip 2911a at which location the end or ends of the coaxial cable(s) may be exposed without insulation in order to act as antennae/emitters of microwave energy.

In some embodiments, TMT instrument 2900a may be configured for use with resistive heating elements rather than monopolar energy as suggested by the accompanying figures. Resistive heating may be used to heat tissue via a suitable array of surface mount resistors or small heating elements powered by an AC or DC current from a conductive conduit.

Instrument 2900a may comprise one or more sensor openings, which may serve as locations for various sensors including but not limited to temperature sensors, fiberoptics, positioning sensors, RFID sensors/tags, and the like. Such openings may be connected to one or more ducts that may pass through and exit on the proximal end of tip 2911a. Alternatively, sensors, including but not limited to sensors positioned in said sensor openings, may be configured to deliver data wirelessly. In some embodiments and implementations, sensors may be used to measure temperature during the instrument's forward and/or back stroke. In some embodiments, said measurement may be taken during an RF pulse or between RF pulses. In alternative embodiments, the sensor exposed at any sensor opening may be a fiberoptic that may sense tissue color and the presence of blood. In alternative embodiments, temperature sensors utilizing ultrasonic methods may be used.

In some embodiments, cameras or other real-time sensing devices may be incorporated into the instrument, such as positioned immediately proximal of the beads and/or treatment tip. Such sensing devices may be used, for example, to detect bleeding, velocity of the device through tissue, examine treated tissue, precisely view the target region, etc.

In alternative embodiments, the energy window may be configured to deliver various modalities of energy, including but not limited to, radiant heating, resistive heating, thermochromic, microwave, ultrasonic, electrosurgical, intense pulse light, LASER, or any of the other forms of treatment energy disclosed herein.

In the alternative embodiment depicted in FIG. 30, TMT instrument 3000 comprises TMT tip 3011 and shaft 3090. This embodiment is similar to the embodiment depicted in FIG. 29a, in that it comprises an angled tip 3011 coupled to shaft 3090 at bend 3012, and a non-branching, TMT tip 3011 with constant cross-sectional size/dimensions. However, TMT tip 3011 is continuously curved with a constant radius of curvature yielding a circular path that extends beyond the path of shaft 3090 in/on both directions/sides. In this embodiment, the pattern of termini 3064 differs from other embodiments. Conductive projection 3093 serves to couple the conductive core or another energy delivery conduit of the device to an energy delivery system (not shown).

In another alternative embodiment depicted in FIG. 31, TMT instrument 3100 comprises TMT tip 3111 and shaft 3190. This embodiment also comprises an angled tip 3111 coupled to shaft 3190 at bend 3112. Tip 3111 comprises an anfractuous, non-branching, TMT tip 3111 with constant cross-sectional size/dimensions. However, TMT tip 3111 comprises a pointed distal tip which is comprised of a plurality of straight portions and a plurality of curved/angled portions coupling the plurality of straight portions yielding termini 3164 positioned in the shape of a chevron. Conductive projection 3193 serves to couple the conductive core or another energy delivery conduit of the device to an energy delivery system (not shown).

In some embodiments, TMT shafts may vary in length from 1 cm to 40 cm preferably about 10 cm to 20 cm and the TMT tip size may vary from 5 mm to 30 mm, preferably 10 to 20 mm.

In alternative embodiments, TMT tips may be rigid and comprised of ceramic, glass, metal, and/or plastics. In alternative embodiments, the TMT shaft may be rigid, or semi-rigid, or even flexible, and may comprise metal and plastics. Having a TMT shaft that is semi-rigid and/or flexible may allow the surgeon to bend the device and thus alter the position of the treatment tip with respect to a relatively distant treatment zone as compared to the location of the entrance wound. For example, a surgeon may treat a portion of cellulite on the lower thigh while having the TMT enter the body in a relatively hidden underwear or bikini zone entrance incision; since the thigh may have an arc to its surface and if the treatment zone is wider than the path created from the entrance wound to the treatment zone, flexing the shaft with or without the aid of another external force may allow the treatment tip to encounter all desired areas.

In various electrosurgical embodiments, the shaft and/or contents within may be electrically conductive in order to transmit the electrosurgical energy from an electrosurgical generator to the TMT termini. The TMT tip may or may not be coupled and/or continuous with the TMT shaft However, in other embodiments, such as electrosurgical embodiments, the TMT tip and/or contents within may or may not be electrically conductive or insulated].

In some embodiments, an energy window and/or energy delivery termini may be positioned on the bottom surface of the tip, either in addition to or as an alternative to such positioning on the upper surface of the tip. However, in various implementations, a surgeon may simply invert the tip of a top-mounted energy window so that it points in the opposite direction (for example, away from the surface skin and toward the subcutaneous tissues. This inward/subcutaneous direction of energy may be useful in directing energy toward the subcutaneous deposits in cellulite and other cosmetic conditions.

FIG. 32 depicts an embodiment of a bipolar TMT device. TMT device 3200 may comprise a non-branching, anfractuous, treatment tip. Like TMT devices 2900a and 2900b, this TMT device may be inserted into relatively small entrance wounds in the skin or other organ systems and/or may be advanced through a tissue path preferably created by one of the lysing tips/devices disclosed herein. As previously mentioned, the depicted TMT device is also non-branching, which may also facilitate extension of the treatment device through an entrance wound of relatively small size.

Thus, the depicted bipolar TMT device 3200 may be inserted into the relatively small entrance wound, ultimately to be extended through the previously dissected tissue planes for treatment of adjacent tissue. The end of the tip may be inserted into/through the entrance wound. The tip may then be snaked at different angles if necessary, while being advanced into the entrance wound until the shaft portion reaches the entrance wound and/or the tip has been fully inserted into the patient's body. The bipolar TMT device, especially when used in skin, may be monitored by instrumentation including, but not limited to, external infrared camera, thermistor, thermocouple, ultrasonic methods, and the like.

The TMT device disclosed herein may comprise a device that may be plugged into an electrosurgical pencil and/or another suitable energy source or instrument and may therefore be part of an electrosurgical treatment system. Additional instrumentation that may couple with the TMT may include a grasping device.

Tip 3211 comprises a non-branching, anfractuous tip comprising a first distal straight portion 3214d that curves/bends at 3212b to become a relatively straight proximal portion 3214p that extends from curve 3212a to become or attach to shaft 3290. First distal straight portion 3214d is parallel to straight proximal portion 3214p. Both straight portions comprise treatment termini. More particularly, portion 3214p comprises treatment termini 3264p that may be of a first polarity and straight portion 3214d comprises termini 3264n of a second, opposite polarity. Electrical signals may travel through the tissue and/or ionic fluids between the oppositely charged termini, thus altering the tissues and/or fluids in between the opposing termini.

In alternative embodiments, one or more portions of the TMT tip may be positioned in a plane relative to the shaft wherein the bends/curves of the tip may direct various segments into different treatment planes. This may be helpful in forcing, for example, treatment window or termini 3264*n*/3264*p* into positions to contact and/or deliver energy to target tissues in a more desirable fashion.

FIGS. 33*a*-36*d* depict various different shapes of projecting electrode termini assemblies 3311 that may be used in connection with any of the TMT tips disclosed herein that may yield more beneficial treatment results by, for example, improving contact with adjacent tissue during treatment. Such termini shapes may be beneficial in that their surface projection may reduce the tendency for unwanted arcing and make electrical discharge more predictable and/or uniform. In FIGS. 33*a*-33*d*, base 3314 is relatively planar, preferably non-conductive, and may be continuous with other materials in the TMT tip. A nonconductive shell 3316, which may be conical in some embodiments, extends from the more planar base 3314 reaching an apex just slightly below conductive cylindrical termini core 3364. Conductive cylindrical termini core 3364 originates at conductive base 3393 from within a portion or chamber of the nonconductive shell 3316. In alternative embodiments, conductive termini core 3393 may terminate equal to or slightly above nonconductive shell 3316, which may be conical in some embodiments. A depression 3364*d* may be formed at the apex of conductive cylindrical termini core 3364, which depression 3364*d* may be slightly rounded or sharper edged depending upon a surgeons' desire for the tendency of electrical discharge. In some embodiments, conductive cylindrical termini core 3364 may be flat, domed, or pointed at its distal surface/eminence and/or may lack a depression/dell. In some embodiments, conductive termini core may be conical, cylindrical, dome-shaped, and/or may otherwise comprise a larger base portion tapering to a narrower tip. It is also contemplated that the various projecting electrode termini disclosed herein, including each of those depicted in FIGS. 33*a*-36*d*, may alternatively be used in connection with other tissue treatment/modification devices, such as tissue dissection and/or modification devices comprising lysing tips, beads, and the like.

FIGS. 34*a*-34*d* depict an alternative embodiment of a projecting electrode termini assembly 3411 comprising a cylindrical conductive termini core 3464 that define a hollow opening or hole 3464*h*, which opening/hole may have a depth that is between about 10% to 100% of the length of the distance from the top of conductive cylindrical termini core 3464 to conductive base 3493. In alternative embodiments, the opening/hole may further extend into base 3493 to various degrees. The embodiment depicted in FIGS. 34*a*-34*d* is similar in almost all other respects of the embodiment depicted in FIGS. 33*a*-33*d* with the exception of hole/opening 3464*h*. This hole may allow for greater electrical discharge and the ability to determine whether the device has been previously used. In alternative embodiments, the hole may be cylindrical, conical, v-shaped, or have any other shape as desired. As with nonconductive shell 3316, nonconductive shell 3416 extends from a non-conductive base 3414.

The alternative embodiment of a projecting electrode termini assembly 3511 depicted in FIGS. 35*a*-35*d* is similar in almost all other respects of the embodiment depicted in FIGS. 33*a*-33*d* with the exception that the center of the dome formed by termini core 3564, and is connected to conductive base 3593, defines a domed/projection 3564*n* in the center of the crater, which in the depicted embodiment forms an "island" of sorts. This shape may present for beneficial electrical discharge at not only the rim of the conductive termini core 3564 but at the domed island 3564*n* itself. In alternative embodiments, the level of the tip of the domed island 3564*n* may be above, level with, or below the outer rim of termini core 3564 and/or nonconductive conical shell 3516. As with termini 3316 and 3416, nonconductive shell 3516 extends from a non-conductive base 3514.

FIGS. 36*a*-36*d* illustrate yet another example of a projecting electrode termini assembly 3611 comprising a conical conductive termini core 3664 that has a conical hole/opening 3664*h*, which is shown extending down to conductive base 3693, but may extend only partially down this length in alternative embodiments and may, for example, terminate adjacent to non-conductive base 3614 rather than fully down to base 3693. In alternative embodiments, the hole may penetrate base 3693 to various degrees. The embodiment depicted in FIGS. 36*a*-36*d* is similar in almost all other respects of the embodiment depicted in FIGS. 34*a*-34*d* with nonconductive shell 3616 extending from non-conductive base 3614.

FIG. 37 depicts another example of a TMT instrument 3700 comprising a shaft 3790 terminating in a treatment tip 3711 comprising a treatment window defined by a plurality of energy emitting treatment termini 3764. Tip 3711 extends from shaft 3790 at bend 3712 and extends at a right angle relative to shaft 3790. Tip 3711 further comprises a non-branching treatment tip having a constant, or at least substantially constant, tip diameter, which, again, may allow for insertion into a relatively small entrance wound. In this embodiment, the tissue treatment tip comprises an upper surface, a lower surface, and opposing side surfaces, wherein the opposing side surface comprises a bend, and wherein the bend is smooth and lacks any sharp points or edges. In the depicted embodiment, the edges transitioning between the side surfaces and the upper and lower surfaces are also smooth and lacking in any sharp points/edges. However, as described above, alternative embodiments are contemplated in which these edges may be sharp.

FIG. 38 depicts yet another example of a TMT instrument 3800. Although the shape of instrument 3800, including tip 3811 of instrument 3800, is similar to that of instrument 3200, in which tip 3811 comprises a non-branching, anfractuous treatment tip that may be inserted into relatively small entrance wounds in the skin or other organ systems and/or may be advanced through a tissue path preferably created by one of the lysing tips/devices disclosed herein, unlike instrument 3200, tip 3811 comprises a treatment window on one of the two straight portions and a sensor window on the other.

More particularly, the proximal straight portion 3814*p*, which bends at bend 3812*a* from shaft 3890, comprises a treatment window defined by a plurality of treatment termini 3864 that curves/bends at U-turn bend 3812*b* to become a relatively straight distal portion 3814*d*. Distal straight portion 3814*d* comprises a sensor window 3898, which may comprise a temperature sensor in some embodiments. By positioning a sensor window on one arm/portion and a treatment window on the other, a surgeon may immediately sense a temperature of tissue after it is treated. It should be understood that the positioning of the treatment and sensor windows may be reversed in alternative embodiments. Thus, although the embodiment depicted in FIG. 38 may be configured to sense tissue temperature during a backstroke, by reversing the positioning of the treatment and sensor windows, tissue temperature may be sensed during a forward stroke. In still other embodiments, temperature sensors and tissue treatment elements may be provided on both arms of the device to allow for sensing of treated tissue in either direction.

Other embodiments of lysing tips 3933/3933' extending from a shaft 3990/3990' of an electrosurgical lysing instrument are depicted in FIGS. 39*a* and 39*b*, respectively. Lysing tip 3933 comprises a plurality of beads 3950 defining distal protrusions 3950*d*, which together define a single recession 3902 therebetween. A distal lysing segment 3961*d* is positioned within recession 3902 and, as previously described throughout this disclosure, is configured to deliver electrosurgical energy therefrom for treating tissue during a surgical procedure. Similarly, each of the beads 3950 further defines a proximal-facing protrusion 3950*p* on either side of shaft 3990. Proximal lysing segments 3961*p*, which may be defined by a single lysing member or separate lysing members, may extend from and/or be positioned within recessions defined on the proximal end of lysing tip 3933 between proximal protrusions 3950*p* and the adjacent portion of shaft 3990.

Beads 3950 of lysing tip 3933 differ from the beads of embodiments depicted in earlier figures in that beads 3950 comprise flattened upper and lower surfaces to form a plate-like bead structure. It should be understood that, whereas the depicted embodiment comprises planar upper and lower surfaces that are parallel to one another, other contemplated embodiments may comprise flattened upper and/or lower surfaces that are not strictly parallel to one another but should still be considered to comprise "flattened" surfaces. Similarly, in some embodiments, the upper and/or lower surfaces may be at least substantially flat. For example, there may be some bumps, curves, or the like while still forming surfaces that should be considered "at least substantially" flat or flattened for purposes of this disclosure.

Lysing tip 3933' is similar to lysing tip 3933 with the exception that lysing tip 3933' comprises faceted beads 3950'. More particularly, beads 3950' comprise facets 3975' on both the distal 3950*d'* and proximal 3950*p'* tips. Providing such facets 3975', although optional, may facilitate a concentration of pressure at certain angles, particularly more acute angles relative to the primary axis of motion and/or the shaft 3990', that may facilitate tissue dissection for certain applications.

In some embodiments, cameras or other real-time sensing devices may be incorporated into the instrument, such as positioned immediately proximal of the beads and/or treatment tip. Such sensing devices may be used, for example, to detect bleeding, velocity of the device through tissue, examine treated tissue, precisely view the target region, etc.

It will be understood by those having skill in the art that changes may be made to the details of the above-described embodiments without departing from the underlying principles presented herein. Any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined only by the following claims.

The invention claimed is:

1. A tissue modification instrument for delivery of tissue-modification energy during a surgical procedure, comprising:
    a shaft extending along an axis;
    a tissue treatment tip at a distal end of the shaft, the tissue treatment tip comprising a plurality of discrete energy delivery elements facing an upper tissue plane and/or a plurality of discrete energy delivery elements facing a lower tissue plane and configured to deliver pulsed tissue-modification energy towards the upper and/or lower tissue planes, wherein each of the energy delivery elements comprises either a conical frustum having a recessed apical cavity or a cylindrical frustum having a recessed apical cavity, wherein the tissue treatment tip comprises a non-branching tip that comprises one or more bends that extend the tissue treatment tip away from the axis and one or more bends that extend the tissue treatment tip towards the axis to define a tissue treatment region that is wider than a width of the shaft, and wherein the tissue treatment tip comprises a terminal end.

2. The tissue modification instrument of claim 1, wherein the tissue treatment tip comprises an anfractuous tip.

3. The tissue modification instrument of claim 1, wherein a cross-sectional size of the tissue treatment tip is at least substantially identical to a cross-sectional size of at least a portion of the shaft extending along the axis adjacent to the tissue treatment tip.

4. The tissue modification instrument of claim 3, wherein a cross-sectional size of the tissue treatment tip is at least substantially identical to a cross-sectional size of the shaft along an entire length of the shaft.

5. The tissue modification instrument of claim 1, wherein the one or more energy delivery elements comprises a plurality of discrete energy delivery termini.

6. The tissue modification instrument of claim 1, wherein the one or more energy delivery elements is configured to deliver at least one of electrosurgical, LASER, intense pulse light, resistive heat, radiant heat, thermochromic, ultrasound, and microwave.

7. The tissue modification instrument of claim 1, wherein the tissue treatment tip comprises an upper surface, a lower surface, and opposing side surfaces, wherein the opposing side surfaces comprise one or bends, and wherein each of the one or more bends are smooth and lack any sharp points or edges.

8. The tissue modification instrument of claim 7, wherein the tissue treatment tip defines an at least substantially circular shape extending from the shaft.

9. The tissue modification instrument of claim 7, wherein the tissue treatment tip defines a shape having three at least substantially straight, interconnected segments defined by the tissue treatment tip with an opening between the terminal end and the shaft.

10. The tissue modification instrument of claim 9, wherein a corner between two adjacent segments of the three segments forms a distal tip of the tissue modification instrument.

11. The tissue modification instrument of claim 1, wherein the tissue treatment tip comprises a first set of energy delivery elements of a first polarity and a second set of energy delivery elements of a second polarity.

12. The tissue modification instrument of claim 11, wherein the tissue treatment tip comprises a first arm and a second arm positioned opposite from the first arm, wherein the first set of energy delivery elements is positioned on the first arm, and wherein the second set of energy delivery elements is positioned on the second arm.

13. The tissue modification instrument of claim 1, wherein the tissue treatment tip comprises a first portion spaced apart from a second portion, wherein the first portion comprises a first set of energy delivery elements, and wherein the second portion comprises a temperature sensor configured to sense a temperature of tissue treated using the first set of energy delivery elements.

14. The tissue modification instrument of claim 13, wherein the first portion is positioned on a first arm of the tissue treatment tip, wherein the second portion is positioned on a second arm of the tissue treatment tip, and wherein the first arm is spaced apart from the second arm.

15. The tissue modification instrument of claim 1, wherein the terminal end is configured to be positioned through an entrance wound having an at least substantially identical length as a cross-sectional width of the terminal end.

16. The tissue modification instrument of claim 1, further comprising a space defined between the terminal end of the tissue treatment tip and a distal end of the shaft.

17. The tissue modification instrument of claim 1, wherein the tissue treatment tip comprises a cross-sectional perimeter that is at least substantially identical to a cross-sectional perimeter of the shaft.

18. The tissue modification instrument of claim 1, wherein the tissue treatment tip comprises:

a first bend that extends the tissue treatment tip away from the axis;

a second bend that extends the tissue treatment tip towards the axis; and a third bend that extends the tissue treatment tip away from the axis and rearward towards a proximal end of the tissue modification instrument to define a tissue treatment region that is wider than a width of the shaft.

\* \* \* \* \*